United States Patent
Yang et al.

(10) Patent No.: US 11,142,582 B2
(45) Date of Patent: Oct. 12, 2021

(54) ANTI-CD40 ANTIBODIES AND USES THEREOF

(71) Applicant: Eucure (Beijing) Biopharma Co., Ltd, Beijing (CN)

(72) Inventors: Yi Yang, Beijing (CN); Chunyan Dong, Beijing (CN); Fang Yang, Beijing (CN); Chengyuan Lu, Beijing (CN); Yuelei Shen, Beijing (CN); Jian Ni, Beijing (CN); Yanan Guo, Beijing (CN); Yunyun Chen, Beijing (CN); Jingshu Xie, Beijing (CN)

(73) Assignee: Eucure (Beijing) Biopharma Co., Ltd, Beijing (CN)

(*) Notice: Subject to any disclaimer, the term of this patent is extended or adjusted under 35 U.S.C. 154(b) by 0 days.

(21) Appl. No.: 17/149,209

(22) Filed: Jan. 14, 2021

(65) Prior Publication Data

US 2021/0155705 A1   May 27, 2021

Related U.S. Application Data

(63) Continuation of application No. PCT/CN2018/096494, filed on Jul. 20, 2018.

(51) Int. Cl.
| | |
|---|---|
| *A61P 35/00* | (2006.01) |
| *C07K 16/28* | (2006.01) |
| *A61K 47/68* | (2017.01) |
| *A61K 39/00* | (2006.01) |

(52) U.S. Cl.
CPC ...... *C07K 16/2878* (2013.01); *A61K 47/6803* (2017.08); *A61K 47/6849* (2017.08); *A61P 35/00* (2018.01); *A61K 2039/505* (2013.01); *C07K 2317/24* (2013.01); *C07K 2317/33* (2013.01); *C07K 2317/76* (2013.01); *C07K 2317/92* (2013.01); *C07K 2317/94* (2013.01)

(58) Field of Classification Search
CPC ............ C07K 16/2878; C07K 2317/33; C07K 2317/76; C07K 2317/92; C07K 2317/24; C07K 2317/94; A61K 47/6803; A61K 47/6849; A61K 2039/505; A61P 35/00
USPC .................................................... 424/173.1
See application file for complete search history.

(56) References Cited

U.S. PATENT DOCUMENTS

| | | | |
|---|---|---|---|
| 4,522,811 | A | 6/1985 | Eppstein et al. |
| 4,603,112 | A | 7/1986 | Paoletti et al. |
| 4,676,980 | A | 6/1987 | Segal et al. |
| 4,769,330 | A | 9/1988 | Paoletti et al. |
| 4,777,127 | A | 10/1988 | Suni et al. |
| 5,017,487 | A | 5/1991 | Stunnenberg et al. |

FOREIGN PATENT DOCUMENTS

| | | |
|---|---|---|
| EP | 0345242 | 12/1989 |
| GB | 2200651 | 8/1988 |
| WO | WO 89/01973 | 3/1989 |
| WO | WO 91/02805 | 3/1991 |
| WO | WO 96/27011 | 9/1996 |
| WO | WO 99/42075 | 8/1999 |
| WO | WO 2008/077546 | 7/2008 |

OTHER PUBLICATIONS

Rudikoff et al (Proc. Natl. Acad. Sci. USA, 79(6): 1979-1983, Mar. 1982).*
Colman P. M. (Research in Immunology, 145:33-36, 1994).*
PCT International Preliminary Report on Patentability in International Appln. No. PCT/CN2018/096494, dated Jan. 26, 2021, 4 pages.
PCT International Search Report and Written Opinion in International Appln. No. PCT/CN2018/096494, dated Feb. 21, 2019, 7 pages.
Abhinandan et al., "Analysis and improvements to Kabat and structurally correct numbering of antibody variable domains," Molecular immunology, 2008, 45:3832-3839.
Beatty, et al. "CD40 agonists alter tumor stroma and show efficacy against pancreatic carcinoma in mice and humans." Science 331. 6024 (2011): 1612-1616.
Brennan et al. "Preparation of bispecific antibodies by chemical recombination of monoclonal immunoglobulin G1 fragments," Science, 1985 229:81-83.
Chothia et al., "Canonical structures for the hypervariable regions of immunoglobulins," J. Mol. Biol., 1987, 196:901-917.
Chothia et al., "Conformations of immunoglobulin hypervariable regions," Nature, Dec. 1989, 342(6252):877-83.
Creelan, "Update on immune checkpoint inhibitors in lung cancer," Cancer Control, 2014, 21:80-89.
Fisher-Hoch et al., "Protection of rhesus monkeys from fatal Lassa fever by vaccination with a recombinant vaccinia virus containing the Lassa virus glycoprotein gene," Proc. Natl. Acad. Sci. USA, 1989, 86:317-321.
Guzman et al., "Efficient gene transfer into myocardium by direct injection of adenovirus vectors," Cir. Res., 1993, 73:1202-1207.
Guzman et al., "Efficient and selective adenovirus-mediated gene transfer into vascular neointima," Circulation, 1993, 88(6)2838-2848.
Irani, et al."Molecular properties of human IgG subclasses and their implications for designing 10 therapeutic monoclonal antibodies against infectious diseases." Molecular immunology, 2015, 67:171-182.
Jones et al., "Replacing the complementarity determining regions in a human antibody with those from a mouse," Nature, May 1986, 321:522-525.

(Continued)

*Primary Examiner* — Yan Xiao
(74) *Attorney, Agent, or Firm* — Fish & Richardson P.C.

(57) ABSTRACT

This disclosure relates to anti-CD40 (TNF Receptor Superfamily Member 5) antibodies, antigen-binding fragments, and the uses thereof.

14 Claims, 22 Drawing Sheets
Specification includes a Sequence Listing.

(56) References Cited

OTHER PUBLICATIONS

Kass-Eisler et al., "Quantitative determination of adenovirus-mediated gene delivery to rat cardiac myocytes in vitro and in vivo," Proc. Natl. Acad. Sci. USA, Dec. 1993, 90:11498-11502.

Kohler et al., "Continuous cultures of fused cells secreting antibody of predefined specificity," 1975, Nature 256:495-497.

Kolls et al., "Prolonged and effective blockade of tumor necrosis factor activity through adenovirus-mediated gene transfer," Proc. Natl. Acad. Sci.USA, 1994, 91:215-219.

Morea et al.,"Antibody structure, prediction and redesign," Biophys Chem., Oct. 1997, 68(1-3):9-16.

Ponomarenko et al., Antibody-protein interactions benchmark datasets and prediction tools evaluation, BMC Structural Biology, Oct. 2007 7:64.

Riechmann et al., "Reshaping human antibodies for therapy," Nature, Apr. 1988, 332:323-327.

Rosenfeld et al., "Adenovirus-mediated transfer of a recombinant alpha 1-antitrypsin gene to the lung epithelium in vivo," Apr. 1991, Science, 252:431-434.

Silva et al. "The S228P mutation prevents in vivo and in vitro IgG4 Fab-arm exchange as demonstrated using a combination of novel quantitative immunoassays and physiological matrix preparation." Journal of Biological Chemistry, 2015, 290(9):5462-5469.

Ulmer et al., "Heterologous protection against influenza by injection of DNA encoding a viral protein," Science, 1993 259:1745-1749.

Verhoeyen et al., "Reshaping human antobodies:grafting an antilysozyme activity," 1988, Science, 239:1534-1536.

Vidarsson, et al., "IgG subclasses and allotypes: from structure to effector function," Frontiers in immunology, Oct. 2014, 5:1-17.

Vonderheide et al., "Agonistic CD40 antibodies and cancer therapy," Clinical Cancer Research, 2013, 1035-1043.

Vonderheide, et al. "Clinical activity and immune modulation in cancer patients treated with CP-870,893, a novel CD40 agonist monoclonal antibody." Journal of Clinical Oncology, 2007, 25(7):876-883.

Wolff et al., "Monoclonal antibody homodimers:Ehanced antitumor activity in nude mice," Cancer Res., Jun. 1993, 53:2560-2565.

Wu et al., "An analysis of the sequences of the variable regions of bence jones proteins and myeloma light chains and their implications for antibody complementarity,", Journal of Experimental Medicine, 1970, 132(2)211-250.

\* cited by examiner

Kabat CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 03-7F10 or humanized 03-7F10 | DYYMY | 1 | YISYGGDSTFYPDTVRG | 2 | PAPSAHSYYLDY | 3 | RASQDISNYLN | 4 | YYTSRLHS | 5 | QQGKTLPFT | 6 |
| 06-6A7 or humanized 06-6A7 | SYYIY | 7 | GINPRNGGTNFNEKFKS | 8 | HGNGVY | 9 | RSSQSLLHSNGNTYLH | 10 | QVSNRFS | 11 | SQTTHVPWT | 12 |
| 07-4H6 or humanized 07-4H6 | SGYWN | 13 | FISYSGSTYYTPSLKS | 14 | FRRYDDGVDY | 15 | RASHEISGYLS | 16 | AASTLAS | 17 | LQYSSYPWT | 18 |

FIG. 16

Chothia CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 03-7F10 or humanized 03-7F10 | GFTFSDYYMY | 19 | SYGGDS | 20 | PAPSAHSYYLDY | 3 | RASQDISNYLN | 4 | YTSRLHS | 21 | QQGKTLPFT | 6 |
| 06-6A7 or humanized 06-6A7 | GYTFISYYIY | 22 | NPRNGG | 23 | HGNGVY | 9 | RSSQSLLHSNGNTYLH | 10 | QVSNRFS | 11 | SQTTHVPWT | 12 |
| 07-4H6 or humanized 07-4H6 | GDSVSSGYWN | 24 | SYSGS | 25 | FRRYDDGVDY | 15 | RASHEISGYLS | 16 | AASTLAS | 17 | LQYSSYPWT | 18 |

FIG. 17

| Protein | Amino acid sequence | SEQ ID NO: |
|---|---|---|
| Human CD40 (hCD40) NP_001241.1 | MVRLPLQCVLWGCLLTAVHPEPPTACREKQYLINSQCCSLCQPGQKLVSDCTEFTETECLPCGESEFL DTWNRETHCHQHKYCDPNLGLRVQQKGTSETDTICTCEEGWHCTSEACESCVLHRSCSPGFVKQIAT GVSDTICEPCPVGFFSNVSSAFEKCHPWTSCETKDLVVQQAGTNKTDVVCGPQDRLRALVVIPIFGI LFAILLVLVFIKKVAKKPTNKAPHPKQEPQEINFPDDLPGSNTAAPVQETLHGCQPVTQEDGKESRIS VQERQ | 26 |
| Mouse CD40 (mCD40) NP_035741.2 | MVSLPRLCALWGCLLTAVHLGQCVTCSDKQYLHDGQCCDLCQPGSRLTSHCTALEKTQCHPCDSGEFS AQWNREIRCHQHRHCEPNQGLRVKKEGTAESDTVCTCKEGQHCTSKDCEACAQHTPCIPGFGVMEMAT ETTDTVCHPCPVGFFSNQSSLFEKCYPWTSCEDKNLEVLQKGTSQTNVICGLKSRMRALLVIPVVMGI LITIFGVFLYIKKVVKKPKDNEILPPAARRQDPQEMEDYPGHNTAAPVQETLHGCQPVTQEDGKESRI SVQERQVTDSIALRPLV | 27 |
| Monkey CD40 (rmCD40) NP_001527291.1 | MVRLPLQCVL WGCLLTAVYP EPPTACREKQ YLINSQCCSL CQPGQKLVSD CTEFTETECL PCSESEFLDT WNRETRCHQH KYCDPNLGLR VQQKGTSETD TICTCEEGLH CMSESCESCV PHRSCLPGFG VKQIATGVSD TICEPCPVGF FSNVSSAFEK CRPWTSCETK DLVVQQAGTN KTDVVCGPQD RQRALVVIPI CLGILFVILL LVLVFIKKVA KKPNDKAPHP KQEPQEINFL DDLPGSNPAA PVQETLHGCQ PVTQEDGKES RISVQERQ | 28 |
| Chimeric CD40 (chiCD40) (Humanized CD40) | MVSLPRLCALWGCLLTAVHPEPPTACREKQYLINSQCCSLCQPGQKLVSDCTEFTETECLPCGESEFL DTWNRETHCHQHKYCDPNLGLRVQQKGTSETDTICTCEEGWHCTSEACESCVLHRSCSPGFVKQIAT GVSDTICEPCPVGFFSNVSSAFEKCHPWTSCETKDLVVQQAGTNKTDVVCGPQDRLRALLVIPVVMGI LITIFGVFLYIKKVVKKPKDNEILPPAARRQDPQEMEDYPGHNTAAPVQETLHGCQPVTQEDGKESRI SVQERQVTDSIALRPLV | 29 |

| Humanized antibody variable domains | Description | AMINO ACID SEQUENCE | SEQ ID NO: |
|---|---|---|---|
| Humanized heavy chain variable domain (H1) based on 7F10 | HuVHv1: humanization percentage 84.7%; Not top hit to human and *Macaca fascicularis* | EVQLVESGGGLVQPGGSLRLSCATSGFTFSDYYMYWVRQAPGK RLEWVAYISYGGDSTFYPDTVRGRFTISRDNAKNSLYLQMNSL RAEDTAVYYCARPAPSAHSYYLDYWGQGTLLTVSS | 30 |
| Humanized heavy chain variable domain (H2) based on 7F10 | HuVHv2: humanization percentage 82.7%; Not top hit to human and *Macaca fascicularis* | EVQLVESGGGLVQPGGSLRLSCATSGFTFSDYYMYWVRQAPGK RLEWVAYISYGGDSTFYPDTVRGRFTISRDNAKNSLYLQMSSL KAEDTAVYYCARPAPSAHSYYLDYWGQGTLLTVSS | 31 |
| Humanized heavy chain variable domain (H3) based on 7F10 | HuVHv3: humanization percentage 78.6%; Not top hit to human and *Macaca fascicularis* | EVKLVESGGGLVQPGGSLRLSCATSGFTFSDYYMYWVRQAPEK RLEWVAYISYGGDSTFYPDTVRGRFTISRDNAKNALYLQMSRL KAEDTAVYYCARPAPSAHSYYLDYWGQGTLLTVSS | 32 |
| Humanized light chain variable domain (K1) based on 7F10 | HuVLv1: humanization percentage 85.3%; top hit to human and *Macaca fascicularis* | DIQMTQSPSSLSASVGDRVTITCRASQDISNYLNWYQQKPGGA VKLLIYYTSRLHSGLPSRFSGSGSGTDFTFTISSLQPEDIATY YCQQGKTLPFTFASGTKLEIK | 33 |
| Humanized light chain variable domain (K2) based on 7F10 | HuVLv2: humanization percentage 84.2%; Not top hit to human and *Macaca fascicularis* | DIQMTQSPSSLSASVGDRVTITCRASQDISNYLNWYQQKPGGA VKLLIYYTSRLHSGLPSRFSGSGSGTDYTFTISSLQPEDIATY YCQQGKTLPFTFASGTKLEIK | 34 |
| Humanized light chain variable domain (K3) based on 7F10 | HuVLv3: humanization percentage 82.1%; Not top hit to human and *Macaca fascicularis* | DIQMTQSTSSLSASVGDRVTITCRASQDISNYLNWYQQKPGGA VKLLIYYTSRLHSGLPSRFSGSGSGTDYTLTISSLQQEDIATY YCQQGKTLPFTFASGTKLEIK | 35 |
| Humanized light chain variable domain (K4) based on 7F10 | HuVLv4: humanization percentage 80%; Not top hit to human and *Macaca fascicularis* | DIQMTQSTSSLSASVGDRVTITCRASQDISNYLNWYQQKPDGT VKLLIYYTSRLHSGLPSRFSGSGSGTDYTLTISSLQQEDIATY YCQQGKTLPFTFASGTKLEIK | 36 |

| Humanized antibody variable domains | Description | AMINO ACID SEQUENCE | SEQ ID NO: |
|---|---|---|---|
| Humanized heavy chain variable domain (H1) based on 6A7 | HuVHv1: humanization percentage 84.7%; top hit to human and *Macaca fascicularis* | QVQLVQSGAEVKKPGASVKVSCKASGYTFISYYIYWRQAPGQ GLEWMGGINPRNGGTNFNEKFKSRVTLTVDTSISTAYMELSRL RSEDTAVYYCARHGNGVYWGQGTTVTVSS | 37 |
| Humanized heavy chain variable domain (H2) based on 6A7 | HuVHv2: humanization percentage 82.7%; top hit to human and *Macaca fascicularis* | QVQLVQSGAEVKKPGASVKVSCKASGYTFISYYIYWRQAPGQ GLEWIGGINPRNGGTNFNEKFKSRATLTVDTSISTAYMELSRL RSEDTAVYYCARHGNGVYWGQGTTVTVSS | 38 |
| Humanized heavy chain variable domain (H3) based on 6A7 | HuVHv3: humanization percentage 81.6%; top hit to human and *Macaca fascicularis* | QVQLVQSGAEVKKPGASVKVSCKASGYTFISYYIYWRQAPGQ GLEWIGGINPRNGGTNFNEKFKSRATLTVDTSISTAYMELSRL RSEDTAVYYCTRHGNGVYWGQGTTVTVSS | 39 |
| Humanized heavy chain variable domain (H4) based on 6A7 | HuVHv4: humanization percentage 79.6%; top hit to human and *Macaca fascicularis* | QVQLVQSGAEVKKPGASVKLSCKASGYTFISYYIYWKQAPGQ GLEWIGGINPRNGGTNFNEKFKSRATLTVDTSISTAYMELSRL RSEDTAVYYCTRHGNGVYWGQGTTLTVSS | 40 |
| Humanized light chain variable domain (K1) based on 6A7 | HuVLv1: humanization percentage 91%; top hit to human and *Macaca fascicularis* | DVVMTQsPLSLPVtLGqpASISCRSSQSLLHSNGNTYLHWfqQ rPGQSPrHLIYQVSNRFSGVPDRFSGSGSGTDFTLKISRVEAE DvGVYyCSQTTHVPWTFGGGTKvEIK | 41 |
| Humanized light chain variable domain (K2) based on 6A7 | HuVLv2: humanization percentage 88%; Not top hit to human and *Macaca fascicularis* | DVVMTQSPLSLPVTLGQPASISCRSSQSLLHSNGNTYLHWYQQ RPGQSPNHLIYQVSNRFSGVPDRFSGSGSGTDFTLKISRVEAE DVGVYFCSQTTHVPWTFGGGTKVEIK | 42 |
| Humanized light chain variable domain (K3) based on 6A7 | HuVLv3: humanization percentage 87%; Not top hit to human and *Macaca fascicularis* | DVVMTQSPLSLPVTLGDPASISCRSSQSLLHSNGNTYLHWYQQ RPGQSPNHLIYQVSNRFSGVPDRFSGSGSGTDFTLKISRVEAE DVGVYFCSQTTHVPWTFGGGTKLEIK | 43 |

FIG. 20

| Humanized antibody variable domains | Description | AMINO ACID SEQUENCE | SEQ ID NO: |
|---|---|---|---|
| Humanized heavy chain variable domain (H1) based on 4H6 | HuVHv1: humanization percentage 88.9%; top hit to human and *Macaca fascicularis* | QVQLQESGPGLVKPSQTLSLTCTVSGDSVSSGYWNWIRKHPG KKLEWIGFISYSGSTYYTPSLKSRVTISRDTSKNQFSLKLSS VTAADTAVYYCARFRRYDDGVDYWGQGTLVTVSS | 44 |
| Humanized heavy chain variable domain (H2) based on 4H6 | HuVHv2: humanization percentage 87.9%; top hit to human and *Macaca fascicularis* | EVQLQESGPGLVKPSQTLSLTCTVSGDSVSSGYWNWIRKHPG KKLEWIGFISYSGSTYYTPSLKSRVTISRDTSKNQFSLKLSS VTAADTAVYYCARFRRYDDGVDYWGQGTLVTVSS | 45 |
| Humanized heavy chain variable domain (H3) based on 4H6 | HuVHv3: humanization percentage 83.8%; top hit to human and *Macaca fascicularis* | EVQLQESGPGLVKPSQTLSLTCTVSGDSVSSGYWNWIRKHPG KKLEYMGFISYSGSTYYTPSLKSRITISRDTSKNQFSLKLSS VTAADTAVYFCARFRRYDDGVDYWGQGTLVTVSS | 46 |
| Humanized heavy chain variable domain (H4) based on 4H6 | HuVHv4: humanization percentage 82.8%; top hit to human and *Macaca fascicularis* | EVQLQESGPGLVKPSQTLSLTCTVSGDSVSSGYWNWIRKFPG KKLEYMGFISYSGSTYYTPSLKSRITISRDTSKNQFSLKLSS VTAADTAVYFCARFRRYDDGVDYWGQGTLVTVSS | 47 |
| Humanized light chain variable domain (K1) based on 4H6 | HuVLv1: humanization percentage 87.4%; top hit to human and *Macaca fascicularis* | DIQMTQSPSamSASvGdRVtiTCRASHEISGYLSWfQQKPgG vIKRLINAASTLASGVPsRFSGSRSGtEftLTIsSLqpEDFA tYYCLQYSSYPWTFGGGTKLEIK | 48 |
| Humanized light chain variable domain (K2) based on 4H6 | HuVLv2: humanization percentage 84.2%; top hit to human and *Macaca fascicularis* | DIQMTQSPSAMSASVGDRVTITCRASHEISGYLSWIQQKPGG TIKRLINAASTLASGVPSRFSGSRSGTEFTLTISSLQPEDFA DYYCLQYSSYPWTFGGGTKLEIK | 49 |
| Humanized light chain variable domain (K3) based on 4H6 | HuVLv3: humanization percentage 83.2%; top hit to human and *Macaca fascicularis* | DIQMTQSPSAMSASVGDRVTITCRASHEISGYLSWIQQKPGG TIKRLINAASTLASGVPSRFSGSRSGTEYTLTISSLQPEDFA DYYCLQYSSYPWTFGGGTKLEIK | 50 |
| Humanized light chain variable domain (K4) based on 4H6 | HuVLv4: humanization percentage 82.1%; Not top hit to human and *Macaca fascicularis* | DIQMTQSPSAMSASVGDRVTLTCRASHEISGYLSWIQQKPGG TIKRLINAASTLASGVPSRFSGSRSGTEYTLTISSLQPEDFA DYYCLQYSSYPWTFGGGTKLEIK | 51 |

FIG. 21

03-7F10 ("7F10") Heavy chain variable region (SEQ ID NO:52)
EVKLVESGGGLVQPGGSLKLSCATSGFTFSDYMYMVWVRQTPEKRLEWVAYISYGGDSTFYPDTVRGRFTISRDNAKNALYLQMSRLKSEDTAVYYCAR
PAPSAHSYYLDYWGQGTTLTVSS 03-7F10 ("7F10") Light chain variable region (SEQ ID NO: 53)
DIQMTQTTSSLSASLGDRVTISCRASQDISNYLNWYQQKPDGTVKLLIYYTSRLHSGLPSRFSGSGSGTDYSLTISNLEQEDIATYYCQQGKTLPFTF
ASGTKLEIK 06-6A7 ("6A7") Heavy chain variable region (SEQ ID NO: 54)
QVQLQQPGAELVKPGASVKLSCKASGYTFISYYIYWVKQRPGQGLEWIGGINPRNGGTNFNEKFKSKATLTVDKSSSTAYMQLSSLTSEDSAVYYCTR
HGNGVYWGQGTTLTVSS 06-6A7 ("6A7") Light chain variable region (SEQ ID NO: 55)
DVVMTQTPLSLPVSLGDQASISCRSSQSLLHSNGNTYLHWYLQKPGQSPNHLIYQVSNRFSGVPDRFSGSGSGTDFTLKISRVEAEDLGVYFCSQTTH
VPWTFGGGTKLEIK 07-4H6 ("4H6") Heavy chain variable region (SEQ ID NO: 56)
EVKLQESGPSLVKPSQTLSLTCSVTGDSVSSGYWNWIRKFPGNKLEYMGFISYSGSTYYTPSLKSRISITRDTSKNQFYLQLNSVTTEDTATYFCARF
RRYDDGVDYWGQGTTLTVSS 07-4H6 ("4H6") Light chain variable region (SEQ ID NO: 57)
DIQMTQSPSSLSASLGERVSLTCRASHEISGYLSWIQQKPDGTIKRLINAASTLASGVPKRFSGSRSGSEYSLTINSLESEDFADYYCLQYSSYPWTF
GGGTKLEIK

FIG. 22

SEQUENCE LISTING

<160> NUMBER OF SEQ ID NOS: 57

<210> SEQ ID NO 1
<211> LENGTH: 5
<212> TYPE: PRT
<213> ORGANISM: Artificial Sequence
<220> FEATURE:
<223> OTHER INFORMATION: CDR sequence

<400> SEQUENCE: 1

Asp Tyr Tyr Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: CDR sequence

```
<400> SEQUENCE: 2

Tyr Ile Ser Tyr Gly Gly Asp Ser Thr Phe Tyr Pro Asp Thr Val Arg
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: CDR sequence

<400> SEQUENCE: 3

Pro Ala Pro Ser Ala His Ser Tyr Tyr Leu Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDR sequence

<400> SEQUENCE: 4

Arg Ala Ser Gln Asp Ile Ser Asn Tyr Leu Asn
1               5                   10

<210> SEQ ID NO 5
<211> LENGTH: 8
<212> TYPE: PRT
<213> ORGANISM: Artificial Sequence
<220> FEATURE:
<223> OTHER INFORMATION: CDR sequence

<400> SEQUENCE: 5

Tyr Tyr Thr Ser Arg Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR sequence

<400> SEQUENCE: 6

Gln Gln Gly Lys Thr Leu Pro Phe Thr
1               5

<210> SEQ ID NO 7
<211> LENGTH: 5
<212> TYPE: PRT
<213> ORGANISM: Artificial Sequence
<220> FEATURE:
<223> OTHER INFORMATION: CDR sequence

<400> SEQUENCE: 7

Ser Tyr Tyr Ile Tyr
1               5

<210> SEQ ID NO 8
<211> LENGTH: 17
<212> TYPE: PRT
<213> ORGANISM: Artificial Sequence
<220> FEATURE:
```

```
<223> OTHER INFORMATION: CDR sequence

<400> SEQUENCE: 8

Gly Ile Asn Pro Arg Asn Gly Gly Thr Asn Phe Asn Glu Lys Phe Lys
1               5                  10                  15
Ser

<210> SEQ ID NO 9
<211> LENGTH: 6
<212> TYPE: PRT
<213> ORGANISM: Artificial Sequence
<220> FEATURE:
<223> OTHER INFORMATION: CDR sequence

<400> SEQUENCE: 9

His Gly Asn Gly Val Tyr
1               5

<210> SEQ ID NO 10
<211> LENGTH: 16
<212> TYPE: PRT
<213> ORGANISM: Artificial Sequence
<220> FEATURE:
<223> OTHER INFORMATION: CDR sequence

<400> SEQUENCE: 10

Arg Ser Ser Gln Ser Leu Leu His Ser Asn Gly Asn Thr Tyr Leu His
1               5                  10                  15

<210> SEQ ID NO 11
<211> LENGTH: 7
<212> TYPE: PRT
<213> ORGANISM: Artificial Sequence
<220> FEATURE:
<223> OTHER INFORMATION: CDR sequence

<400> SEQUENCE: 11

Gln Val Ser Asn Arg Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: CDR sequence

<400> SEQUENCE: 12

Ser Gln Thr Thr His Val Pro Trp Thr
1               5

<210> SEQ ID NO 13
<211> LENGTH: 5
<212> TYPE: PRT
<213> ORGANISM: Artificial Sequence
<220> FEATURE:
<223> OTHER INFORMATION: CDR sequence

<400> SEQUENCE: 13

Ser Gly Tyr Trp Asn
1               5

<210> SEQ ID NO 14
<211> LENGTH: 16
<212> TYPE: PRT
<213> ORGANISM: Artificial Sequence
```

```
<220> FEATURE:
<223> OTHER INFORMATION: CDR sequence

<400> SEQUENCE: 14

Phe Ile Ser Tyr Ser Gly Ser Thr Tyr Tyr Thr Pro Ser Leu Lys Ser
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: CDR sequence

<400> SEQUENCE: 15

Phe Arg Arg Tyr Asp Asp Gly Val Asp Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: CDR sequence

<400> SEQUENCE: 16

Arg Ala Ser His Glu Ile Ser Gly Tyr Leu Ser
1               5                   10

<210> SEQ ID NO 17
<211> LENGTH: 7
<212> TYPE: PRT
<213> ORGANISM: Artificial Sequence
<220> FEATURE:
<223> OTHER INFORMATION: CDR sequence

<400> SEQUENCE: 17

Ala Ala Ser Thr Leu Ala Ser
1               5

<210> SEQ ID NO 18
<211> LENGTH: 9
<212> TYPE: PRT
<213> ORGANISM: Artificial Sequence
<220> FEATURE:
<223> OTHER INFORMATION: CDR sequence

<400> SEQUENCE: 18

Leu Gln Tyr Ser Ser Tyr Pro Trp Thr
1               5

<210> SEQ ID NO 19
<211> LENGTH: 10
<212> TYPE: PRT
<213> ORGANISM: Artificial Sequence
<220> FEATURE:
<223> OTHER INFORMATION: CDR sequence

<400> SEQUENCE: 19

Gly Phe Thr Phe Ser Asp Tyr Tyr Met Tyr
1               5                   10

<210> SEQ ID NO 20
<211> LENGTH: 6
<212> TYPE: PRT
<213> ORGANISM: Artificial Sequence
<220> FEATURE:
```

```
<223> OTHER INFORMATION: CDR sequence

<400> SEQUENCE: 20

Ser Tyr Gly Gly Asp Ser
1               5

<210> SEQ ID NO 21
<211> LENGTH: 7
<212> TYPE: PRT
<213> ORGANISM: Artificial Sequence
<220> FEATURE:
<223> OTHER INFORMATION: CDR sequence

<400> SEQUENCE: 21

Tyr Thr Ser Arg Leu His Ser
1               5

<210> SEQ ID NO 22
<211> LENGTH: 10
<212> TYPE: PRT
<213> ORGANISM: Artificial Sequence
<220> FEATURE:
<223> OTHER INFORMATION: CDR sequence

<400> SEQUENCE: 22

Gly Tyr Thr Phe Ile Ser Tyr Tyr Ile Tyr
1               5                   10

<210> SEQ ID NO 23
<211> LENGTH: 6
<212> TYPE: PRT
<213> ORGANISM: Artificial Sequence
<220> FEATURE:
<223> OTHER INFORMATION: CDR sequence

<400> SEQUENCE: 23

Asn Pro Arg Asn Gly Gly
1               5

<210> SEQ ID NO 24
<211> LENGTH: 10
<212> TYPE: PRT
<213> ORGANISM: Artificial Sequence
<220> FEATURE:
<223> OTHER INFORMATION: CDR sequence

<400> SEQUENCE: 24

Gly Asp Ser Val Ser Ser Gly Tyr Trp Asn
1               5                   10

<210> SEQ ID NO 25
<211> LENGTH: 5
<212> TYPE: PRT
<213> ORGANISM: Artificial Sequence
<220> FEATURE:
<223> OTHER INFORMATION: CDR sequence

<400> SEQUENCE: 25

Ser Tyr Ser Gly Ser
1               5

<210> SEQ ID NO 26
<211> LENGTH: 277
<212> TYPE: PRT
<213> ORGANISM: human

<400> SEQUENCE: 26
```

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
            245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 27
<211> LENGTH: 289
<212> TYPE: PRT
<213> ORGANISM: Mouse

<400> SEQUENCE: 27

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
            35                  40                  45

Ser His Cys Thr Ala Leu Glu Lys Thr Gln Cys His Pro Cys Asp Ser
50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
```

```
            85                  90                  95
Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
            115                 120                 125

Phe Gly Val Met Glu Met Ala Thr Glu Thr Thr Asp Thr Val Cys His
            130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val Ile Pro Val Val Met Gly Ile Leu Ile Thr Ile
            195                 200                 205

Phe Gly Val Phe Leu Tyr Ile Lys Lys Val Val Lys Lys Pro Lys Asp
            210                 215                 220

Asn Glu Ile Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln Val Thr Asp Ser Ile Ala Leu Arg Pro Leu
            275                 280                 285

Val

<210> SEQ ID NO 28
<211> LENGTH: 278
<212> TYPE: PRT
<213> ORGANISM: Monkey

<400> SEQUENCE: 28

Met Val Arg Leu Pro Leu Gln Cys Val Leu Trp Gly Cys Leu Leu Thr
1               5                   10                  15

Ala Val Tyr Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Ser Glu
        50                  55                  60

Ser Glu Phe Leu Asp Thr Trp Asn Arg Glu Thr Arg Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Leu His Cys Met
            100                 105                 110

Ser Glu Ser Cys Glu Ser Cys Val Pro His Arg Ser Cys Leu Pro Gly
            115                 120                 125

Phe Gly Val Lys Gln Ile Ala Thr Gly Val Ser Asp Thr Ile Cys Glu
            130                 135                 140

Pro Cys Pro Val Gly Phe Phe Ser Asn Val Ser Ser Ala Phe Glu Lys
145                 150                 155                 160

Cys Arg Pro Trp Thr Ser Cys Glu Thr Lys Asp Leu Val Val Gln Gln
```

```
                    165                 170                 175
Ala Gly Thr Asn Lys Thr Asp Val Val Cys Gly Pro Gln Asp Arg Gln
                180                 185                 190

Arg Ala Leu Val Val Ile Pro Ile Cys Leu Gly Ile Leu Phe Val Ile
            195                 200                 205

Leu Leu Leu Val Leu Val Phe Ile Lys Lys Val Ala Lys Lys Pro Asn
        210                 215                 220

Asp Lys Ala Pro His Pro Lys Gln Glu Pro Gln Glu Ile Asn Phe Leu
225                 230                 235                 240

Asp Asp Leu Pro Gly Ser Asn Pro Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln
        275

<210> SEQ ID NO 29
<211> LENGTH: 289
<212> TYPE: PRT
<213> ORGANISM: Artificial Sequence
<220> FEATURE:
<223> OTHER INFORMATION: Humanized CD40

<400> SEQUENCE: 29

Met Val Ser Leu Pro Arg Leu Cys Ala Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Leu Val Ile Pro Val Val Met Gly Ile Leu Ile Thr Ile
        195                 200                 205

Phe Gly Val Phe Leu Tyr Ile Lys Lys Val Lys Lys Pro Lys Asp
    210                 215                 220

Asn Glu Ile Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
```

```
                245                 250                 255
His Gly Cys Gln Pro Val Thr Gln Glu Asp Gly Lys Glu Ser Arg Ile
            260                 265                 270

Ser Val Gln Glu Arg Gln Val Thr Asp Ser Ile Ala Leu Arg Pro Leu
        275                 280                 285

Val

<210> SEQ ID NO 30
<211> LENGTH: 121
<212> TYPE: PRT
<213> ORGANISM: Artificial Sequence
<220> FEATURE:
<223> OTHER INFORMATION: Heavy chain variable region based on 7F10

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Tyr Met Tyr Trp Val Arg Gln Ala Pro Gly Lys Arg Leu Glu Trp Val
        35                  40                  45

Ala Tyr Ile Ser Tyr Gly Gly Asp Ser Thr Phe Tyr Pro Asp Thr Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Ala Pro Ser Ala His Ser Tyr Tyr Leu Asp Tyr Trp Gly
            100                 105                 110

Gln Gly Thr Leu Leu Thr Val Ser Ser
        115                 120

<210> SEQ ID NO 31
<211> LENGTH: 121
<212> TYPE: PRT
<213> ORGANISM: Artificial Sequence
<220> FEATURE:
<223> OTHER INFORMATION: Heavy chain variable region based on 7F10

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Tyr Met Tyr Trp Val Arg Gln Ala Pro Gly Lys Arg Leu Glu Trp Val
        35                  40                  45

Ala Tyr Ile Ser Tyr Gly Gly Asp Ser Thr Phe Tyr Pro Asp Thr Val
    50                  55                  60

Arg Gly Arg Phe Thr Ile Ser Arg Asp Asn Ala Lys Asn Ser Leu Tyr
65                  70                  75                  80

Leu Gln Met Ser Ser Leu Lys Ala Glu Asp Thr Ala Val Tyr Tyr Cys
                85                  90                  95

Ala Arg Pro Ala Pro Ser Ala His Ser Tyr Tyr Leu Asp Tyr Trp Gly
            100                 105                 110

Gln Gly Thr Leu Leu Thr Val Ser Ser
        115                 120
```

```
<210> SEQ ID NO 32
<211> LENGTH: 121
<212> TYPE: PRT
<213> ORGANISM: Artificial Sequence
<220> FEATURE:
<223> OTHER INFORMATION: Heavy chain variable region based on 7F10

<400> SEQUENCE: 32

Glu Val Lys Leu Val Glu Ser Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Tyr Met Tyr Trp Val Arg Gln Ala Pro Glu Lys Arg Leu Glu Trp Val
        35                  40                  45

Ala Tyr Ile Ser Tyr Gly Gly Asp Ser Thr Phe Tyr Pro Asp Thr Val
    50                  55                  60

Arg Gly Arg Phe Thr Ile Ser Arg Asp Asn Ala Lys Asn Ala Leu Tyr
65                  70                  75                  80

Leu Gln Met Ser Arg Leu Lys Ala Glu Asp Thr Ala Val Tyr Tyr Cys
                85                  90                  95

Ala Arg Pro Ala Pro Ser Ala His Ser Tyr Tyr Leu Asp Tyr Trp Gly
            100                 105                 110

Gln Gly Thr Thr Leu Thr Val Ser Ser
        115                 120

<210> SEQ ID NO 33
<211> LENGTH: 107
<212> TYPE: PRT
<213> ORGANISM: Artificial Sequence
<220> FEATURE:
<223> OTHER INFORMATION: Light chain variable region based on 7F10

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Ala Val Lys Leu Leu Ile
        35                  40                  45

Tyr Tyr Thr Ser Arg Leu His Ser Gly Leu Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Lys Thr Leu Pro Phe
                85                  90                  95

Thr Phe Ala Ser Gly Thr Lys Leu Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: Light chain variable region based on 7F10

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30
```

```
Leu Asn Trp Tyr Gln Gln Lys Pro Gly Gly Ala Val Lys Leu Leu Ile
            35                  40                  45

Tyr Tyr Thr Ser Arg Leu His Ser Gly Leu Pro Ser Arg Phe Ser Gly
 50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Gly Lys Thr Leu Pro Phe
                 85                  90                  95

Thr Phe Ala Ser Gly Thr Lys Leu Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: Light chain variable region based on 7F10

<400> SEQUENCE: 35

Asp Ile Gln Met Thr Gln Ser Thr Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Gly Ala Val Lys Leu Leu Ile
            35                  40                  45

Tyr Tyr Thr Ser Arg Leu His Ser Gly Leu Pro Ser Arg Phe Ser Gly
 50                  55                  60

Ser Gly Ser Gly Thr Asp Tyr Thr Leu Thr Ile Ser Ser Leu Gln Gln
 65                  70                  75                  80

Glu Asp Ile Ala Thr Tyr Tyr Cys Gln Gln Gly Lys Thr Leu Pro Phe
                 85                  90                  95

Thr Phe Ala Ser Gly Thr Lys Leu Glu Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: Light chain variable region based on 7F10

<400> SEQUENCE: 36

Asp Ile Gln Met Thr Gln Ser Thr Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Leu Pro Ser Arg Phe Ser Gly
 50                  55                  60

Ser Gly Ser Gly Thr Asp Tyr Thr Leu Thr Ile Ser Ser Leu Gln Gln
 65                  70                  75                  80

Glu Asp Ile Ala Thr Tyr Tyr Cys Gln Gln Gly Lys Thr Leu Pro Phe
                 85                  90                  95

Thr Phe Ala Ser Gly Thr Lys Leu Glu Ile Lys
            100                 105
```

<210> SEQ ID NO 37
<211> LENGTH: 115
<212> TYPE: PRT
<213> ORGANISM: Artificial Sequence
<220> FEATURE:
<223> OTHER INFORMATION: Heavy chain variable region based on 6A7

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Tyr Ile Tyr Trp Val Arg Gln Ala Pro Gly Gln Gly Leu Glu Trp Met
        35                  40                  45

Gly Gly Ile Asn Pro Arg Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg His Gly Asn Gly Val Tyr Trp Gly Gln Gly Thr Thr Val Thr
            100                 105                 110

Val Ser Ser
        115
```

<210> SEQ ID NO 38
<211> LENGTH: 115
<212> TYPE: PRT
<213> ORGANISM: Artificial Sequence
<220> FEATURE:
<223> OTHER INFORMATION: Heavy chain variable region based on 6A7

<400> SEQUENCE: 38

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Tyr Ile Tyr Trp Val Arg Gln Ala Pro Gly Gln Gly Leu Glu Trp Ile
        35                  40                  45

Gly Gly Ile Asn Pro Arg Asn Gly Gly Thr Asn Phe Asn Glu Lys Phe
    50                  55                  60

Lys Ser Arg Ala Thr Leu Thr Val Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg His Gly Asn Gly Val Tyr Trp Gly Gln Gly Thr Thr Val Thr
            100                 105                 110

Val Ser Ser
        115
```

<210> SEQ ID NO 39
<211> LENGTH: 115
<212> TYPE: PRT
<213> ORGANISM: Artificial Sequence
<220> FEATURE:
<223> OTHER INFORMATION: Heavy chain variable region based on 6A7

<400> SEQUENCE: 39

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Ile Ser Tyr
            20                  25                  30

Tyr Ile Tyr Trp Val Arg Gln Ala Pro Gly Gln Gly Leu Glu Trp Ile
            35                  40                  45

Gly Gly Ile Asn Pro Arg Asn Gly Gly Thr Asn Phe Asn Glu Lys Phe
 50                  55                  60

Lys Ser Arg Ala Thr Leu Thr Val Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Thr Arg His Gly Asn Gly Val Tyr Trp Gly Gln Gly Thr Thr Val Thr
                100                 105                 110

Val Ser Ser
        115

<210> SEQ ID NO 40
<211> LENGTH: 115
<212> TYPE: PRT
<213> ORGANISM: Artificial Sequence
<220> FEATURE:
<223> OTHER INFORMATION: Heavy chain variable region based on 6A7

<400> SEQUENCE: 40

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ile Ser Tyr
            20                  25                  30

Tyr Ile Tyr Trp Val Lys Gln Ala Pro Gly Gln Gly Leu Glu Trp Ile
            35                  40                  45

Gly Gly Ile Asn Pro Arg Asn Gly Gly Thr Asn Phe Asn Glu Lys Phe
 50                  55                  60

Lys Ser Arg Ala Thr Leu Thr Val Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Thr Arg His Gly Asn Gly Val Tyr Trp Gly Gln Gly Thr Thr Leu Thr
                100                 105                 110

Val Ser Ser
        115

<210> SEQ ID NO 41
<211> LENGTH: 112
<212> TYPE: PRT
<213> ORGANISM: Artificial Sequence
<220> FEATURE:
<223> OTHER INFORMATION: Light chain variable region based on 6A7

<400> SEQUENCE: 41

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Asn Gly Asn Thr Tyr Leu His Trp Phe Gln Gln Arg Pro Gly Gln Ser
            35                  40                  45

Pro Arg His Leu Ile Tyr Gln Val Ser Asn Arg Phe Ser Gly Val Pro
 50                  55                  60

Asp Arg Phe Ser Gly Ser Gly Ser Gly Thr Asp Phe Thr Leu Lys Ile
```

```
                    65                  70                  75                  80
Ser Arg Val Glu Ala Glu Asp Val Gly Val Tyr Tyr Cys Ser Gln Thr
                            85                  90                  95

Thr His Val Pro Trp Thr Phe Gly Gly Gly Thr Lys Val Glu Ile Lys
                100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Light chain variable region based on 6A7

<400> SEQUENCE: 42

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Leu His Ser
            20                  25                  30

Asn Gly Asn Thr Tyr Leu His Trp Tyr Gln Gln Arg Pro Gly Gln Ser
        35                  40                  45

Pro Asn His Leu Ile Tyr Gln Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                    85                  90                  95

Thr His Val Pro Trp Thr Phe Gly Gly Gly Thr Lys Val Glu Ile Lys
                100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Light chain variable region based on 6A7

<400> SEQUENCE: 43

Asp Val Val Met Thr Gln Ser Pro Leu Ser Leu Pro Val Thr Leu Gly
1               5                   10                  15

Asp Pro Ala Ser Ile Ser Cys Arg Ser Gln Ser Leu Leu His Ser
            20                  25                  30

Asn Gly Asn Thr Tyr Leu His Trp Tyr Gln Gln Arg Pro Gly Gln Ser
        35                  40                  45

Pro Asn His Leu Ile Tyr Gln Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                    85                  90                  95

Thr His Val Pro Trp Thr Phe Gly Gly Gly Thr Lys Leu Glu Ile Lys
                100                 105                 110

<210> SEQ ID NO 44
<211> LENGTH: 118
<212> TYPE: PRT
<213> ORGANISM: Artificial Sequence
<220> FEATURE:
<223> OTHER INFORMATION: Heavy chain variable region based on 4H6

<400> SEQUENCE: 44
```

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Val Ser Ser Gly
            20                  25                  30

Tyr Trp Asn Trp Ile Arg Lys His Pro Gly Lys Lys Leu Glu Trp Ile
            35                  40                  45

Gly Phe Ile Ser Tyr Ser Gly Ser Thr Tyr Tyr Thr Pro Ser Leu Lys
50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Phe Arg Arg Tyr Asp Asp Gly Val Asp Tyr Trp Gly Gln Gly Thr
                100                 105                 110

Leu Val Thr Val Ser Ser
            115

<210> SEQ ID NO 45
<211> LENGTH: 118
<212> TYPE: PRT
<213> ORGANISM: Artificial Sequence
<220> FEATURE:
<223> OTHER INFORMATION: Heavy chain variable region based on 4H6

<400> SEQUENCE: 45

Glu Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Val Ser Ser Gly
            20                  25                  30

Tyr Trp Asn Trp Ile Arg Lys His Pro Gly Lys Lys Leu Glu Trp Ile
            35                  40                  45

Gly Phe Ile Ser Tyr Ser Gly Ser Thr Tyr Tyr Thr Pro Ser Leu Lys
50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Phe Arg Arg Tyr Asp Asp Gly Val Asp Tyr Trp Gly Gln Gly Thr
                100                 105                 110

Leu Val Thr Val Ser Ser
            115

<210> SEQ ID NO 46
<211> LENGTH: 118
<212> TYPE: PRT
<213> ORGANISM: Artificial Sequence
<220> FEATURE:
<223> OTHER INFORMATION: Heavy chain variable region based on 4H6

<400> SEQUENCE: 46

Glu Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Val Ser Ser Gly
            20                  25                  30

Tyr Trp Asn Trp Ile Arg Lys His Pro Gly Lys Lys Leu Glu Tyr Met
            35                  40                  45

Gly Phe Ile Ser Tyr Ser Gly Ser Thr Tyr Tyr Thr Pro Ser Leu Lys
```

```
                  50                  55                  60
Ser Arg Ile Thr Ile Ser Arg Asp Thr Ser Lys Asn Gln Phe Ser Leu
 65                  70                  75                  80

Lys Leu Ser Ser Val Thr Ala Ala Asp Thr Ala Val Tyr Phe Cys Ala
                 85                  90                  95

Arg Phe Arg Arg Tyr Asp Asp Gly Val Asp Tyr Trp Gly Gln Gly Thr
                100                 105                 110

Leu Val Thr Val Ser Ser
            115

<210> SEQ ID NO 47
<211> LENGTH: 118
<212> TYPE: PRT
<213> ORGANISM: Artificial Sequence
<220> FEATURE:
<223> OTHER INFORMATION: Heavy chain variable region based on 4H6

<400> SEQUENCE: 47

Glu Val Gln Leu Gln Glu Ser Gly Pro Gly Leu Val Lys Pro Ser Gln
 1               5                  10                  15

Thr Leu Ser Leu Thr Cys Thr Val Ser Gly Asp Ser Val Ser Ser Gly
                 20                  25                  30

Tyr Trp Asn Trp Ile Arg Lys Phe Pro Gly Lys Lys Leu Glu Tyr Met
             35                  40                  45

Gly Phe Ile Ser Tyr Ser Gly Ser Thr Tyr Tyr Thr Pro Ser Leu Lys
         50                  55                  60

Ser Arg Ile Thr Ile Ser Arg Asp Thr Ser Lys Asn Gln Phe Ser Leu
 65                  70                  75                  80

Lys Leu Ser Ser Val Thr Ala Ala Asp Thr Ala Val Tyr Phe Cys Ala
                 85                  90                  95

Arg Phe Arg Arg Tyr Asp Asp Gly Val Asp Tyr Trp Gly Gln Gly Thr
                100                 105                 110

Leu Val Thr Val Ser Ser
            115

<210> SEQ ID NO 48
<211> LENGTH: 107
<212> TYPE: PRT
<213> ORGANISM: Artificial Sequence
<220> FEATURE:
<223> OTHER INFORMATION: Light chain variable region based on 4H6

<400> SEQUENCE: 48

Asp Ile Gln Met Thr Gln Ser Pro Ser Ala Met Ser Ala Ser Val Gly
 1               5                  10                  15

Asp Arg Val Thr Ile Thr Cys Arg Ala Ser His Glu Ile Ser Gly Tyr
                 20                  25                  30

Leu Ser Trp Phe Gln Gln Lys Pro Gly Gly Val Ile Lys Arg Leu Ile
             35                  40                  45

Asn Ala Ala Ser Thr Leu Ala Ser Gly Val Pro Ser Arg Phe Ser Gly
         50                  55                  60

Ser Arg Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Ser Ser Tyr Pro Trp
                 85                  90                  95

Thr Phe Gly Gly Gly Thr Lys Leu Glu Ile Lys
                100                 105
```

```
<210> SEQ ID NO 49
<211> LENGTH: 107
<212> TYPE: PRT
<213> ORGANISM: Artificial Sequence
<220> FEATURE:
<223> OTHER INFORMATION: Light chain variable region based on 4H6

<400> SEQUENCE: 49

Asp Ile Gln Met Thr Gln Ser Pro Ser Ala Met Ser Ala Ser Val Gly
1               5                   10                  15

Asp Arg Val Thr Ile Thr Cys Arg Ala Ser His Glu Ile Ser Gly Tyr
            20                  25                  30

Leu Ser Trp Ile Gln Gln Lys Pro Gly Gly Thr Ile Lys Arg Leu Ile
        35                  40                  45

Asn Ala Ala Ser Thr Leu Ala Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Asp Tyr Tyr Cys Leu Gln Tyr Ser Ser Tyr Pro Trp
                85                  90                  95

Thr Phe Gly Gly Gly Thr Lys Leu Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: Light chain variable region based on 4H6

<400> SEQUENCE: 50

Asp Ile Gln Met Thr Gln Ser Pro Ser Ala Met Ser Ala Ser Val Gly
1               5                   10                  15

Asp Arg Val Thr Ile Thr Cys Arg Ala Ser His Glu Ile Ser Gly Tyr
            20                  25                  30

Leu Ser Trp Ile Gln Gln Lys Pro Gly Gly Thr Ile Lys Arg Leu Ile
        35                  40                  45

Asn Ala Ala Ser Thr Leu Ala Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Asp Tyr Tyr Cys Leu Gln Tyr Ser Ser Tyr Pro Trp
                85                  90                  95

Thr Phe Gly Gly Gly Thr Lys Leu Glu Ile Lys
            100                 105

<210> SEQ ID NO 51
<211> LENGTH: 107
<212> TYPE: PRT
<213> ORGANISM: Artificial Sequence
<220> FEATURE:
<223> OTHER INFORMATION: Light chain variable region based on 4H6

<400> SEQUENCE: 51

Asp Ile Gln Met Thr Gln Ser Pro Ser Ala Met Ser Ala Ser Val Gly
1               5                   10                  15

Asp Arg Val Thr Leu Thr Cys Arg Ala Ser His Glu Ile Ser Gly Tyr
            20                  25                  30

Leu Ser Trp Ile Gln Gln Lys Pro Gly Gly Thr Ile Lys Arg Leu Ile
```

```
                 35                  40                  45
Asn Ala Ala Ser Thr Leu Ala Ser Gly Val Pro Ser Arg Phe Ser Gly
 50                  55                  60
Ser Arg Ser Gly Thr Glu Tyr Thr Leu Thr Ile Ser Ser Leu Gln Pro
65                  70                  75                  80
Glu Asp Phe Ala Asp Tyr Tyr Cys Leu Gln Tyr Ser Ser Tyr Pro Trp
                 85                  90                  95
Thr Phe Gly Gly Gly Thr Lys Leu Glu Ile Lys
            100                 105
```

<210> SEQ ID NO 52
<211> LENGTH: 121
<212> TYPE: PRT
<213> ORGANISM: Mus musculus

<400> SEQUENCE: 52

```
Glu Val Lys Leu Val Glu Ser Gly Gly Gly Leu Val Gln Pro Gly Gly
1               5                  10                  15
Ser Leu Lys Leu Ser Cys Ala Thr Ser Gly Phe Thr Phe Ser Asp Tyr
                 20                  25                  30
Tyr Met Tyr Trp Val Arg Gln Thr Pro Glu Lys Arg Leu Glu Trp Val
                 35                  40                  45
Ala Tyr Ile Ser Tyr Gly Gly Asp Ser Thr Phe Tyr Pro Asp Thr Val
 50                  55                  60
Arg Gly Arg Phe Thr Ile Ser Arg Asp Asn Ala Lys Asn Ala Leu Tyr
65                  70                  75                  80
Leu Gln Met Ser Arg Leu Lys Ser Glu Asp Thr Ala Val Tyr Tyr Cys
                 85                  90                  95
Ala Arg Pro Ala Pro Ser Ala His Ser Tyr Tyr Leu Asp Tyr Trp Gly
            100                 105                 110
Gln Gly Thr Thr Leu Thr Val Ser Ser
            115                 120
```

<210> SEQ ID NO 53
<211> LENGTH: 107
<212> TYPE: PRT
<213> ORGANISM: Mus musculus

<400> SEQUENCE: 53

```
Asp Ile Gln Met Thr Gln Thr Thr Ser Ser Leu Ser Ala Ser Leu Gly
1               5                  10                  15
Asp Arg Val Thr Ile Ser Cys Arg Ala Ser Gln Asp Ile Ser Asn Tyr
                 20                  25                  30
Leu Asn Trp Tyr Gln Gln Lys Pro Asp Gly Thr Val Lys Leu Leu Ile
                 35                  40                  45
Tyr Tyr Thr Ser Arg Leu His Ser Gly Leu Pro Ser Arg Phe Ser Gly
 50                  55                  60
Ser Gly Ser Gly Thr Asp Tyr Ser Leu Thr Ile Ser Asn Leu Glu Gln
65                  70                  75                  80
Glu Asp Ile Ala Thr Tyr Tyr Cys Gln Gln Gly Lys Thr Leu Pro Phe
                 85                  90                  95
Thr Phe Ala Ser Gly Thr Lys Leu Glu Ile Lys
            100                 105
```

<210> SEQ ID NO 54
<211> LENGTH: 115
<212> TYPE: PRT

<213> ORGANISM: Mus musculus

<400> SEQUENCE: 54

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Tyr Ile Tyr Trp Val Lys Gln Arg Pro Gly Gln Gly Leu Glu Trp Ile
        35                  40                  45

Gly Gly Ile Asn Pro Arg Asn Gly Gly Thr Asn Phe Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg His Gly Asn Gly Val Tyr Trp Gly Gln Gly Thr Thr Leu Thr
            100                 105                 110

Val Ser Ser
        115

<210> SEQ ID NO 55
<211> LENGTH: 112
<212> TYPE: PRT
<213> ORGANISM: Mus musculus

<400> SEQUENCE: 55

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Asn His Leu Ile Tyr Gln Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Trp Thr Phe Gly Gly Gly Thr Lys Leu Glu Ile Lys
            100                 105                 110

<210> SEQ ID NO 56
<211> LENGTH: 118
<212> TYPE: PRT
<213> ORGANISM: Mus musculus

<400> SEQUENCE: 56

Glu Val Lys Leu Gln Glu Ser Gly Pro Ser Leu Val Lys Pro Ser Gln
1               5                   10                  15

Thr Leu Ser Leu Thr Cys Ser Val Thr Gly Asp Ser Val Ser Ser Gly
            20                  25                  30

Tyr Trp Asn Trp Ile Arg Lys Phe Pro Gly Asn Lys Leu Glu Tyr Met
        35                  40                  45

Gly Phe Ile Ser Tyr Ser Gly Ser Thr Tyr Tyr Thr Pro Ser Leu Lys
    50                  55                  60

Ser Arg Ile Ser Ile Thr Arg Asp Thr Ser Lys Asn Gln Phe Tyr Leu
65                  70                  75                  80

```
Gln Leu Asn Ser Val Thr Thr Glu Asp Thr Ala Thr Tyr Phe Cys Ala
                85                  90                  95

Arg Phe Arg Arg Tyr Asp Asp Gly Val Asp Tyr Trp Gly Gln Gly Thr
            100                 105                 110

Thr Leu Thr Val Ser Ser
        115

<210> SEQ ID NO 57
<211> LENGTH: 107
<212> TYPE: PRT
<213> ORGANISM: Mus musculus

<400> SEQUENCE: 57

Asp Ile Gln Met Thr Gln Ser Pro Ser Ser Leu Ser Ala Ser Leu Gly
1               5                   10                  15

Glu Arg Val Ser Leu Thr Cys Arg Ala Ser His Glu Ile Ser Gly Tyr
            20                  25                  30

Leu Ser Trp Ile Gln Gln Lys Pro Asp Gly Thr Ile Lys Arg Leu Ile
        35                  40                  45

Asn Ala Ala Ser Thr Leu Ala Ser Gly Val Pro Lys Arg Phe Ser Gly
    50                  55                  60

Ser Arg Ser Gly Ser Glu Tyr Ser Leu Thr Ile Asn Ser Leu Glu Ser
65                  70                  75                  80

Glu Asp Phe Ala Asp Tyr Tyr Cys Leu Gln Tyr Ser Ser Tyr Pro Trp
                85                  90                  95

Thr Phe Gly Gly Gly Thr Lys Leu Glu Ile Lys
            100                 105
```

ANTI-CD40 ANTIBODIES AND USES THEREOF

CLAIM OF PRIORITY

This application is a continuation application of and claims priority to International Application No. PCT/CN2018/096494, filed Jul. 20, 2018. The entire contents of the foregoing are incorporated herein by reference.

TECHNICAL FIELD

This disclosure relates to anti-CD40 (TNF Receptor Superfamily Member 5) antibodies and uses thereof.

BACKGROUND

Cancer is currently one of the diseases that have the highest human mortality. According to the World Health Organization statistical data, in 2012, the number of global cancer incidence and death cases reached 14 million and 8.2 million, respectively. In China, the newly diagnosed cancer cases are 3.07 million, and the death toll is 2.2 million.

Recent clinical and commercial success of anticancer antibodies has created great interest in antibody-based therapeutics. There is a need to develop anti-cancer antibodies for use in various antibody-based therapeutics to treat cancers.

SUMMARY

This disclosure relates to anti-CD40 antibodies, antigen-binding fragment thereof, and the uses thereof.

In one aspect, the disclosure relates to an antibody or antigen-binding fragment thereof that binds to CD40 (TNF Receptor Superfamily Member 5) comprising: a heavy chain variable region (VH) comprising complementarity determining regions (CDRs) 1, 2, and 3, wherein the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence; and a light chain variable region (VL) comprising CDRs 1, 2, and 3, wherein the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence, wherein the selected VH CDRs 1, 2, and 3 amino acid sequences and the selected VL CDRs, 1, 2, and 3 amino acid sequences are one of the following:

(1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively;

(2) the selected VH CDRs 1, 2, 3 amino acid sequences are set forth in SEQ ID NOs: 7, 8, 9, respectively, and the selected VL CDRs 1, 2, 3 amino acid sequences are set forth in SEQ ID NOs: 10, 11, 12, respectively;

(3) the selected VH CDRs 1, 2, 3 amino acid sequences are set forth in SEQ ID NOs: 13, 14, 15, respectively, and the selected VL CDRs 1, 2, 3 amino acid sequences are set forth in SEQ ID NOs: 16, 17, 18, respectively.

In some embodiments, the VH comprises CDRs 1, 2, 3 with the amino acid sequences set forth in SEQ ID NOs: 1, 2, and 3 respectively, and the VL comprises CDRs 1, 2, 3 with the amino acid sequences set forth in SEQ ID NOs: 4, 5, and 6, respectively.

In some embodiments, the VH comprises CDRs 1, 2, 3 with the amino acid sequences set forth in SEQ ID NOs: 7, 8, and 9, respectively, and the VL comprises CDRs 1, 2, 3 with the amino acid sequences set forth in SEQ ID NOs: 10, 11, and 12, respectively.

In some embodiments, the VH comprises CDRs 1, 2, 3 with the amino acid sequences set forth in SEQ ID NOs: 13, 14, 15, respectively, and the VL comprises CDRs 1, 2, 3 with the amino acid sequences set forth in SEQ ID NOs: 16, 17, and 18, respectively.

In some embodiments, the antibody or antigen-binding fragment specifically binds to human CD40. In some embodiments, the antibody or antigen-binding fragment is a humanized antibody or antigen-binding fragment thereof. In some embodiments, the antibody or antigen-binding fragment is a single-chain variable fragment (scFV).

In another aspect, the disclosure relates to a nucleic acid comprising a polynucleotide encoding a polypeptide comprising:

(1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 1, 2, and 3, respectively, and wherein the VH, when paired with a light chain variable region (VL) comprising the amino acid sequence set forth in SEQ ID NO: 33, 34, 35, 36, or 53 binds to CD40;

(2) an immunoglobulin light chain or a fragment thereof comprising a VL comprising CDRs 1, 2, and 3 comprising the amino acid sequences set forth in SEQ ID NOs: 4, 5, and 6, respectively, and wherein the VL, when paired with a VH comprising the amino acid sequence set forth in SEQ ID NO: 30, 31, 32, or 52 binds to CD40;

(3) an immunoglobulin heavy chain or a fragment thereof comprising a heavy chain variable region (VH) comprising CDRs 1, 2, and 3 comprising the amino acid sequences set forth in SEQ ID NOs: 7, 8, and 9, respectively, and wherein the VH, when paired with a light chain variable region (VL) comprising the amino acid sequence set forth in SEQ ID NO: 41, 42, 43, or 55 binds to CD40;

(4) an immunoglobulin light chain or a fragment thereof comprising a VL comprising CDRs 1, 2, and 3 comprising the amino acid sequences set forth in SEQ ID NOs: 10, 11, and 12, respectively, and wherein the VL, when paired with a VH comprising the amino acid sequence set forth in SEQ ID NO: 37, 38, 39, 40, or 54 binds to CD40;

(5) an immunoglobulin heavy chain or a fragment thereof comprising a heavy chain variable region (VH) comprising CDRs 1, 2, and 3 comprising the amino acid sequences set forth in SEQ ID NOs: 13, 14, 15, respectively, and wherein the VH, when paired with a light chain variable region (VL) comprising the amino acid sequence set forth in SEQ ID NO: 48, 49, 50, 51, or 57 binds to CD40;

(6) an immunoglobulin light chain or a fragment thereof comprising a VL comprising CDRs 1, 2, and 3 comprising the amino acid sequences set forth in SEQ ID NOs: 16, 17, and 18, respectively, and wherein the VL, when paired with a VH comprising the amino acid sequence set forth in SEQ ID NO: 44, 45, 46, 47, or 56 binds to CD40.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 1, 2, and 3, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 4, 5, and 6, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 7, 8, and 9, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 10, 11, and 12, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 13, 14, and 15, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 16, 17, and 18, respectively.

In some embodiments, the VH when paired with a VL specifically binds to human CD40, or the VL when paired with a VH specifically binds to human CD40.

In some embodiments, the immunoglobulin heavy chain or the fragment thereof is a humanized immunoglobulin heavy chain or a fragment thereof, and the immunoglobulin light chain or the fragment thereof is a humanized immunoglobulin light chain or a fragment thereof.

In some embodiments, the nucleic acid encodes a single-chain variable fragment (scFv). In some embodiments, the nucleic acid is cDNA.

In one aspect, the disclosure relates to a vector comprising one or more of the nucleic acids as described herein. In some embodiments, the vector encodes the VL region and the VH region that together bind to CD40.

In one aspect, the disclosure provides a pair of vectors, wherein each vector comprises one of the nucleic acids as described herein, wherein together the pair of vectors encodes the VL region and the VH region that together bind to CD40.

In another aspect, the disclosure relates to a cell comprising the vector as described herein, or the pair of vectors as described herein. In some embodiments, the cell is a CHO cell.

In one aspect, the disclosure also provides a cell comprising one or more of the nucleic acids as described herein.

In another aspect, the disclosure provides a cell comprising two of the nucleic acids as described herein. In some embodiments, the two nucleic acids together encode the VL region and the VH region that together bind to CD40.

In another aspect, the disclosure relates to methods of producing an antibody or an antigen-binding fragment thereof. The methods include the steps of
(a) culturing the cell as described herein under conditions sufficient for the cell to produce the antibody or the antigen-binding fragment; and
(b) collecting the antibody or the antigen-binding fragment produced by the cell.

In one aspect, the disclosure relates to an antibody or antigen-binding fragment thereof that binds to CD40 comprising a heavy chain variable region (VH) comprising an amino acid sequence that is at least 90% identical to a selected VH sequence, and a light chain variable region (VL) comprising an amino acid sequence that is at least 90% identical to a selected VL sequence, wherein the selected VH sequence and the selected VL sequence are one of the following:
(1) the selected VH sequence is SEQ ID NO: 30, 31, 32, or 52, and the selected VL sequence is SEQ ID NO: 33, 34, 35, 36, or 53;
(2) the selected VH sequence is SEQ ID NO: 37, 38, 39, 40, or 54, and the selected VL sequence is SEQ ID NO: 41, 42, 43, or 55;
(3) the selected VH sequence is SEQ ID NO: 44, 45, 46, 47, or 56, and the selected VL sequence is SEQ ID NO: 48, 49, 50, 51, or 57.

In some embodiments, the VH comprises the sequence of SEQ ID NO: 40 and the VL comprises the sequence of SEQ ID NO: 42.

In some embodiments, the VH comprises the sequence of SEQ ID NO: 39 and the VL comprises the sequence of SEQ ID NO: 43.

In some embodiments, the antibody or antigen-binding fragment specifically binds to human CD40.

In some embodiments, the antibody or antigen-binding fragment is a humanized antibody or antigen-binding fragment thereof. In some embodiments, the antibody or antigen-binding fragment is a single-chain variable fragment (scFV).

In one aspect, the disclosure relates to an antibody-drug conjugate comprising the antibody or antigen-binding fragment thereof as described herein covalently bound to a therapeutic agent. In some embodiments, the therapeutic agent is a cytotoxic or cytostatic agent.

In another aspect, the disclosure relates to methods of treating a subject having cancer. The methods include the steps of administering a therapeutically effective amount of a composition comprising the antibody or antigen-binding fragment thereof as described herein, or the antibody-drug conjugate as described herein, to the subject.

In some embodiments, the subject has a solid tumor (e.g., advanced solid tumor). In some embodiments, the cancer is unresectable melanoma or metastatic melanoma. In some embodiments, the cancer is non-small cell lung cancer (NSCLC), squamous cell carcinoma of the head and neck (SCCHN), head and neck cancer, renal cell carcinoma (RCC), melanoma, bladder cancer, gastric cancer, urothelial cancer, Merkel-cell carcinoma, triple-negative breast cancer (TNBC), or colorectal carcinoma.

In some embodiments, the cancer is melanoma, pancreatic carcinoma, mesothelioma, or a hematological malignancy (e.g., Non-Hodgkin's lymphoma, lymphoma, or chronic lymphocytic leukemia).

In one aspect, the disclosure relates to methods of decreasing the rate of tumor growth. The methods include the steps of contacting a tumor cell with an effective amount of a composition comprising an antibody or antigen-binding fragment thereof as described herein, or the antibody-drug conjugate as described herein.

In another aspect, the disclosure relates methods of killing a tumor cell. The methods include the steps of contacting a tumor cell with an effective amount of a composition comprising the antibody or antigen-binding fragment thereof as described herein, or the antibody-drug conjugate as described herein.

In one aspect, the disclosure provides a pharmaceutical composition comprising the antibody or antigen-binding fragment thereof as described herein, and a pharmaceutically acceptable carrier.

In another aspect, the disclosure also provides a pharmaceutical composition comprising the antibody drug conjugate as described herein, and a pharmaceutically acceptable carrier.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, and cancer of the small intestine. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knock-out of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

As used herein, the term "antibody" refers to any antigen-binding molecule that contains at least one (e.g., one, two, three, four, five, or six) complementary determining region (CDR) (e.g., any of the three CDRs from an immunoglobulin light chain or any of the three CDRs from an immunoglobulin heavy chain) and is capable of specifically binding to an epitope. Non-limiting examples of antibodies include: monoclonal antibodies, polyclonal antibodies, multi-specific antibodies (e.g., bi-specific antibodies), single-chain antibodies, chimeric antibodies, human antibodies, and humanized antibodies. In some embodiments, an antibody can contain an Fc region of a human antibody. The term antibody also includes derivatives, e.g., bi-specific antibodies, single-chain antibodies, diabodies, linear antibodies, and multi-specific antibodies formed from antibody fragments.

As used herein, the term "antigen-binding fragment" refers to a portion of a full-length antibody, wherein the portion of the antibody is capable of specifically binding to an antigen. In some embodiments, the antigen-binding fragment contains at least one variable domain (e.g., a variable domain of a heavy chain or a variable domain of light chain). Non-limiting examples of antibody fragments include, e.g., Fab, Fab', F(ab')$_2$, and Fv fragments.

As used herein, the term "human antibody" refers to an antibody that is encoded by an endogenous nucleic acid (e.g., rearranged human immunoglobulin heavy or light chain locus) present in a human. In some embodiments, a human antibody is collected from a human or produced in a human cell culture (e.g., human hybridoma cells). In some embodiments, a human antibody is produced in a non-human cell (e.g., a mouse or hamster cell line). In some embodiments, a human antibody is produced in a bacterial or yeast cell. In some embodiments, a human antibody is produced in a transgenic non-human animal (e.g., a bovine) containing an unrearranged or rearranged human immunoglobulin locus (e.g., heavy or light chain human immunoglobulin locus).

As used herein, the term "chimeric antibody" refers to an antibody that contains a sequence present in at least two different antibodies (e.g., antibodies from two different mammalian species such as a human and a mouse antibody). A non-limiting example of a chimeric antibody is an antibody containing the variable domain sequences (e.g., all or part of a light chain and/or heavy chain variable domain sequence) of a non-human (e.g., mouse) antibody and the constant domains of a human antibody. Additional examples of chimeric antibodies are described herein and are known in the art.

As used herein, the term "humanized antibody" refers to a non-human antibody which contains minimal sequence derived from a non-human (e.g., mouse) immunoglobulin and contains sequences derived from a human immunoglobulin. In non-limiting examples, humanized antibodies are human antibodies (recipient antibody) in which hypervariable (e.g., CDR) region residues of the recipient antibody are replaced by hypervariable (e.g., CDR) region residues from a non-human antibody (e.g., a donor antibody), e.g., a mouse, rat, or rabbit antibody, having the desired specificity, affinity, and capacity. In some embodiments, the Fv framework residues of the human immunoglobulin are replaced by corresponding non-human (e.g., mouse) immunoglobulin residues. In some embodiments, humanized antibodies may contain residues which are not found in the recipient antibody or in the donor antibody. These modifications can be made to further refine antibody performance. In some embodiments, the humanized antibody contains substantially all of at least one, and typically two, variable domains, in which all or substantially all of the hypervariable loops (CDRs) correspond to those of a non-human (e.g., mouse) immunoglobulin and all or substantially all of the framework regions are those of a human immunoglobulin. The humanized antibody can also contain at least a portion of an immunoglobulin constant region (Fc), typically, that of a human immunoglobulin. Humanized antibodies can be produced using molecular biology methods known in the art. Non-limiting examples of methods for generating humanized antibodies are described herein.

As used herein, the term "single-chain antibody" refers to a single polypeptide that contains at least two immunoglobulin variable domains (e.g., a variable domain of a mammalian immunoglobulin heavy chain or light chain) that is capable of specifically binding to an antigen. Non-limiting examples of single-chain antibodies are described herein.

As used herein, the term "multimeric antibody" refers to an antibody that contains four or more (e.g., six, eight, or ten) immunoglobulin variable domains. In some embodiments, the multimeric antibody is able to crosslink one target molecule (e.g., CD40) to at least one second target molecule (e.g., CTLA-4) on the surface of a mammalian cell (e.g., a human T-cell).

As used herein, the terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, when referring to an antibody, the phrases "specifically binding" and "specifically binds" mean that the antibody interacts with its target molecule (e.g., CD40) preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody. For example, an antibody that specifically binds to a CD40 molecule may be referred to as a CD40-specific antibody or an anti-CD40 antibody.

As used herein, the terms "polypeptide," "peptide," and "protein" are used interchangeably to refer to polymers of amino acids of any length of at least two amino acids.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 16 lists CDR sequences of mouse anti-hCD40 antibodies (03-7F10, 06-6A7, and 07-4H6) and CDR sequences of humanized anti-hCD40 antibodies thereof as defined by Kabat numbering.

FIG. 17 lists CDR sequences of mouse anti-hCD40 antibodies (03-7F10, 06-6A7, and 07-4H6) and CDR sequences of humanized anti-hCD40 antibodies thereof as defined by Chothia numbering.

FIG. 18 lists amino acid sequences of human CD40 (hCD40), mouse CD40 (mCD40), monkey CD40 (rmCD40), and chimeric CD40 (chiCD40).

FIG. 19 lists amino acid sequences of heavy chain variable regions and light chain variable regions of humanized anti-hCD40 antibodies based on 7F10.

FIG. 20 lists amino acid sequences of heavy chain variable regions and light chain variable regions of humanized anti-hCD40 antibodies based on 6A7.

FIG. 21 lists amino acid sequences of heavy chain variable regions and light chain variable regions of humanized anti-hCD40 antibodies based on 4H6.

FIG. 22 lists the amino acid sequence of the heavy chain variable regions and light chain variable regions of mouse anti-hCD40 antibodies 03-7F10, 06-6A7, and 07-4H6.

STATEMENT REGARDING SEQUENCE LISTING

Figure 1:
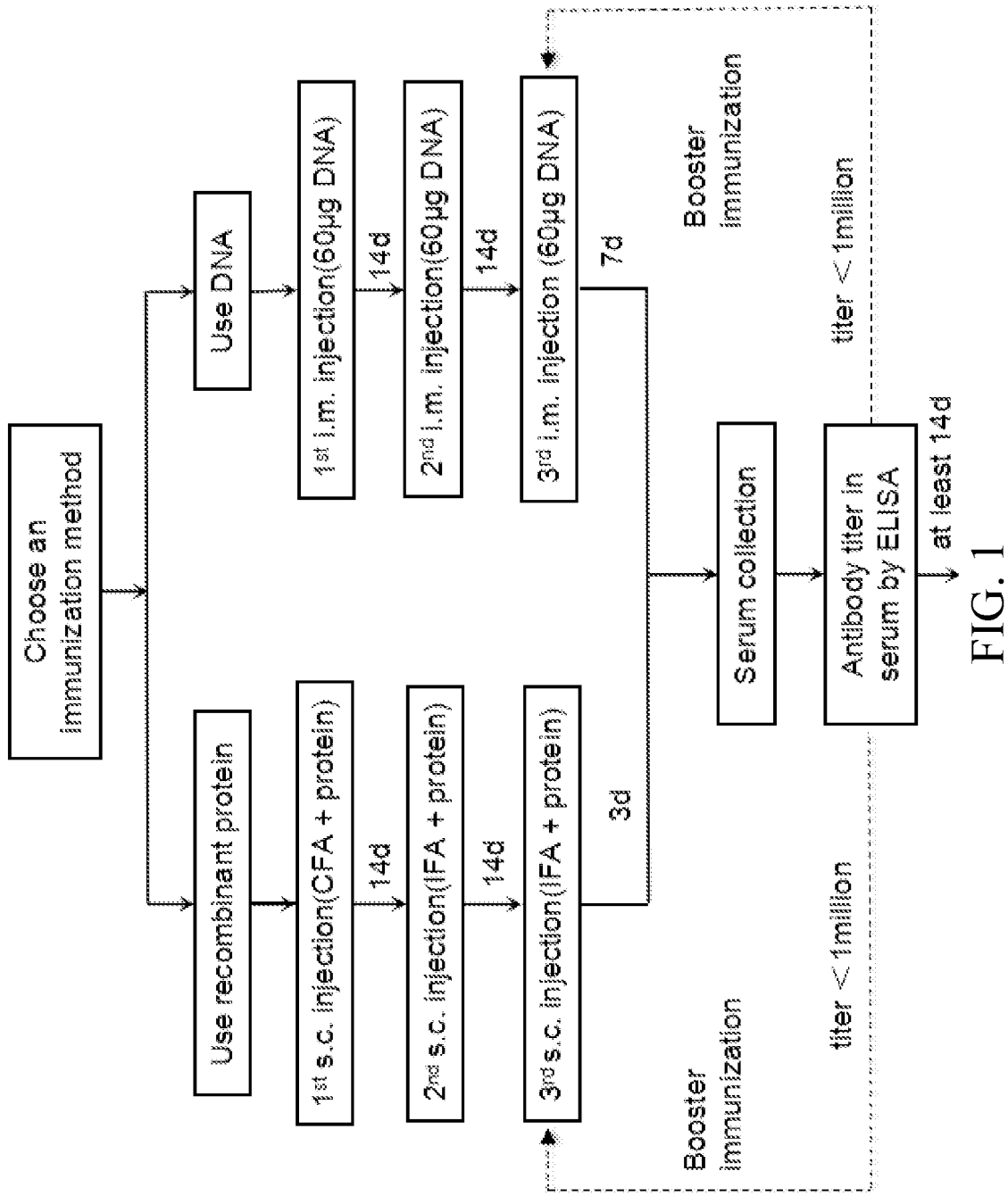
FIG. 1 is a flow chart showing the first part of an exemplary protocol of making anti-hCD40 antibodies.

The Sequence Listing associated with this application is provided in text form in lieu of a paper copy, and is hereby incorporated by reference into the specification. The name of the text file containing the Sequence Listing is Sequence-Listing.txt. The text file is 44.3 KB, and was created and submitted electronically via EFS-Web on Feb. 8, 2021.

DETAILED DESCRIPTION

The present disclosure provides examples of antibodies, antigen-binding fragment thereof, that bind to CD40 (TNF Receptor Superfamily Member 5).

CD40 and Cancer

The immune system can differentiate between normal cells in the body and those it sees as "foreign," which allows the immune system to attack the foreign cells while leaving the normal cells alone. This mechanism sometimes involves proteins called immune checkpoints. Immune checkpoints are molecules in the immune system that either turn up a signal (co-stimulatory molecules) or turn down a signal.

Checkpoint inhibitors can prevent the immune system from attacking normal tissue and thereby preventing autoimmune diseases. Many tumor cells also express checkpoint inhibitors. These tumor cells escape immune surveillance by co-opting certain immune-checkpoint pathways, particularly in T cells that are specific for tumor antigens (Creelan, Benjamin C. "Update on immune checkpoint inhibitors in lung cancer." Cancer Control 21.1 (2014): 80-89). Because many immune checkpoints are initiated by ligand-receptor interactions, they can be readily blocked by antibodies against the ligands and/or their receptors.

CD40 (also known as Tumor Necrosis Factor Receptor Superfamily Member 5 or TNFRSF5) is a tumor necrosis factor receptor superfamily member expressed on antigen presenting cells (APC) such as dendritic cells (DC), macrophages, B cells, and monocytes as well as many non-immune cells and a wide range of tumors. Interaction with its trimeric ligand CD154 (also known as CD40 ligand or CD40L) on activated T helper cells results in APC activation, leading to the induction of adaptive immunity.

Physiologically, signaling via CD40 on APC is thought to represent a major component of T cell help and mediates in large part the capacity of helper T cells to license APC. Ligation of CD40 on DC, for example, induces increased surface expression of costimulatory and MHC molecules, production of proinflammatory cytokines, and enhanced T cell triggering. CD40 ligation on resting B cells increases antigen-presenting function and proliferation.

In pre-clinical models, rat anti-mouse CD40 mAb show remarkable therapeutic activity in the treatment of CD40+ B-cell lymphomas (with 80-100% of mice cured and immune to re-challenge in a CD8 T-cell dependent manner) and are also effective in various CD40-negative tumors. These mAb are able to clear bulk tumors from mice with near terminal disease. CD40 mAb have been investigated in clinical trials and are used for treating melanoma, pancreatic carcinoma, mesothelioma, hematological malignancies, especially Non-Hodgkin's lymphoma, lymphoma, chronic lymphocytic leukemia, and advanced solid tumors.

Therapeutic anti-CD40 antibodies show diverse activities ranging from strong agonism to antagonism. Currently there is no satisfactory explanation for this heterogeneity. The primary mechanistic rationale invoked for agonistic CD40 mAb is to activate host APC in order to induce clinically meaningful anti-tumor T-cell responses in patients. These include T cell-independent but macrophage-dependent triggering of tumor regression. CD40-activated macrophages can become tumoricidal, and least in pancreatic cancer, may also facilitate the depletion of tumor stroma which induces tumor collapse in vivo. Importantly, these mechanisms do not require expression of CD40 by the tumor, which has justified inclusion of patients with a broad range of tumors in many of the clinical trials. Insofar as these strategies aim to activate DC, macrophages, or both, the goal is not necessarily for the CD40 mAb to kill the cell it binds to, for example, via complement mediated cytotoxicity (CMC) or antibody dependent cellular cytoxicity (ADCC). Thus, by design, the strong agonistic antibody does not mediate CMC or ADCC.

In contrast, other human CD40 mAb can mediate CMC and ADCC against CD40+ tumors, such as nearly all B cell malignancies, a fraction of melanomas, and certain carcinomas. Finally, there is some evidence that ligation of CD40 on tumor cells promotes apoptosis and that this can be accomplished without engaging any immune effector pathway. This has been shown for CD40+ B cell malignancies and certain solid tumors such as CD40+ carcinomas and melanomas.

A detailed description of CD40 and its function can be found, e.g., in Vonderheide et al., "Agonistic CD40 antibodies and cancer therapy." (2013): 1035-1043; Beatty, et al. "CD40 agonists alter tumor stroma and show efficacy against pancreatic carcinoma in mice and humans." Science 331.6024 (2011): 1612-1616; Vonderheide, et al. "Clinical activity and immune modulation in cancer patients treated with CP-870,893, a novel CD40 agonist monoclonal antibody." Journal of Clinical Oncology 25.7 (2007): 876-883; each of which is incorporated by reference in its entirety.

The present disclosure provides several anti-CD40 antibodies, antigen-binding fragments thereof, and methods of using these anti-CD40 antibodies and antigen-binding fragments to inhibit tumor growth and to treat cancers.

Antibodies and Antigen Binding Fragments

The present disclosure provides anti-CD40 antibodies and antigen-binding fragments thereof. In general, antibodies (also called immunoglobulins) are made up of two classes of polypeptide chains, light chains and heavy chains. A non-limiting antibody of the present disclosure can be an intact, four immunoglobulin chain antibody comprising two heavy chains and two light chains. The heavy chain of the antibody can be of any isotype including IgM, IgG, IgE, IgA, or IgD or sub-isotype including IgG1, IgG2, IgG2a, IgG2b, IgG3, IgG4, IgE1, IgE2, etc. The light chain can be a kappa light chain or a lambda light chain. An antibody can comprise two identical copies of a light chain and two identical copies of a heavy chain. The heavy chains, which each contain one variable domain (or variable region, VH) and multiple constant domains (or constant regions), bind to one another via disulfide bonding within their constant domains to form the "stem" of the antibody. The light chains, which each contain one variable domain (or variable region, VL) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the principle antigen binding surface of the antibody. The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007); each of which is incorporated herein by reference in its entirety. Unless specifically indicated in the present disclosure, Kabat numbering is used in the present disclosure as a default.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, camelid). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain. In some embodiments, the chimeric antigen receptor also comprises intracellular signaling domains from various costimulatory protein receptors (e.g., CD28, 41BB, ICOS). In some embodiments, the chimeric antigen receptor comprises multiple signaling domains, e.g., CD3z-CD28-41BB or CD3z-CD28-OX40, to increase potency. Thus, in one aspect, the disclosure further provides cells (e.g., T cells) that express the chimeric antigen receptors as described herein.

In some embodiments, the scFV has one heavy chain variable domain, and one light chain variable domain. In some embodiments, the scFV has two heavy chain variable domains, and two light chain variable domains.

Anti-CD40 Antibodies and Antigen-Binding Fragments

The disclosure provides antibodies and antigen-binding fragments thereof that specifically bind to CD40. The antibodies and antigen-binding fragments described herein are capable of binding to CD40. These antibodies can be agonists or antagonists. In some embodiments, these antibodies can promote CD40 signaling pathway thus increase immune response. In some embodiments, these antibodies can initiate CMC or ADCC.

The disclosure provides e.g., mouse anti-CD40 antibodies 03-7F10 ("7F10"), 06-6A7 ("6A7"), and 07-4H6 ("4H6"), the chimeric antibodies thereof, and the humanized antibodies thereof (e.g., some of the antibodies as shown in Table 1).

The CDR sequences for 7F10, and 7F10 derived antibodies (e.g., humanized antibodies) include CDRs of the heavy chain variable domain, SEQ ID NOs: 1-3, and CDRs of the light chain variable domain, SEQ ID NOs: 4-6 as defined by Kabat numbering. The CDRs can also be defined by Chothia system. Under the Chothia numbering, the CDR sequences of the heavy chain variable domain are set forth in SEQ ID NOs: 19, 20, 3 and CDR sequences of the light chain variable domain are set forth in SEQ ID NOs: 4, 21, 6.

Similarly, the CDR sequences for 6A7, and 6A7 derived antibodies include CDRs of the heavy chain variable domain, SEQ ID NOs: 7-9, and CDRs of the light chain variable domain, SEQ ID NOs: 10-12, as defined by Kabat numbering. Under Chothia numbering, the CDR sequences of the heavy chain variable domain are set forth in SEQ ID NOs: 22, 23, 9, and CDRs of the light chain variable domain are set forth in SEQ ID NOs: 10-12.

The CDR sequences for 4H6, and 4H6 derived antibodies include CDRs of the heavy chain variable domain, SEQ ID NOs: 13, 14, 15, and CDRs of the light chain variable domain, SEQ ID NOs: 16, 17, 18, as defined by Kabat numbering. Under Chothia numbering, the CDR sequences of the heavy chain variable domain are set forth in SEQ ID NOs: 24, 25, 15, and CDRs of the light chain variable domain are set forth in SEQ ID NOs: 16, 17, 18.

The amino acid sequences for heavy chain variable regions and light variable regions of the humanized antibodies are also provided. As there are different ways to humanize a mouse antibody (e.g., a sequence can be modified with different amino acid substitutions), the heavy chain and the light chain of an antibody can have more than one version of humanized sequences. The amino acid sequences for the heavy chain variable regions of humanized 7F10 antibody are set forth in SEQ ID NOs: 30-32. The amino acid sequences for the light chain variable regions of humanized 7F10 antibody are set forth in SEQ ID NOs: 33-36. Any of these heavy chain variable region sequences (SEQ ID NO: 30-32) can be paired with any of these light chain variable region sequences (SEQ ID NO: 33-36).

Similarly, the amino acid sequences for the heavy chain variable region of humanized 6A7 antibody are set forth in SEQ ID NOs: 37-40. The amino acid sequences for the light chain variable region of humanized 6A7 antibody are set forth in SEQ ID NOs: 41-43. Any of these heavy chain variable region sequences (SEQ ID NO: 37-40) can be paired with any of these light chain variable region sequences (SEQ ID NO: 41-43).

The amino acid sequences for the heavy chain variable region of humanized 4H6 antibody are set forth in SEQ ID NOs: 44-47. The amino acid sequences for the light chain variable region of humanized 4H6 antibody are set forth in SEQ ID NOs: 48-51. Any of these heavy chain variable region sequences (SEQ ID NO: 44-47) can be paired with any of these light chain variable region sequences (SEQ ID NO: 48-51).

Some chimeric and humanized antibodies based on 7F10, 6A7, and 4H6 are shown in Table 1 and Table 4.

TABLE 1

| Type | Antibody name | VH SEQ ID NO: | VL SEQ ID NO: | Constant regions |
| --- | --- | --- | --- | --- |
| Chimeric antibody based on 6A7 | 6A7-mHvKv-IgG1 | 54 | 55 | Human IgG1 |
| | 6A7-mHvKv-IgG2 | 54 | 55 | Human IgG2 |
| | 6A7-mHvKv-IgG4 | 54 | 55 | Human IgG4 |
| | 6A7-mHvKv-IgG1-N297A | 54 | 55 | Human IgG1 with N297A mutation |
| | 6A7-mHvKv-IgG1-LALA | 54 | 55 | Human IgG1 with LALA mutation |
| Humanized antibodies based on 6A7 | 6A7-H1K1-IgG4 | 37 | 41 | Human IgG4 |
| | 6A7-H2K1-IgG4 | 38 | 41 | Human IgG4 |
| | 6A7-H3K1-IgG4 | 39 | 41 | Human IgG4 |
| | 6A7-H4K1-IgG4 | 40 | 41 | Human IgG4 |
| | 6A7-H1K2-IgG4 | 37 | 42 | Human IgG4 |
| | 6A7-H2K2-IgG4 | 38 | 42 | Human IgG4 |
| | 6A7-H3K2-IgG4 | 39 | 42 | Human IgG4 |
| | 6A7-H4K2-IgG2 | 40 | 42 | Human IgG2 |
| | 6A7-H4K2-IgG4 | 40 | 42 | Human IgG4 |
| | 6A7-H1K3-IgG4 | 37 | 43 | Human IgG4 |
| | 6A7-H2K3-IgG4 | 38 | 43 | Human IgG4 |
| | 6A7-H3K3-IgG2 | 39 | 43 | Human IgG2 |
| | 6A7-H3K3-IgG4 | 39 | 43 | Human IgG4 |
| | 6A7-H4K3-IgG4 | 40 | 43 | Human IgG4 |
| Chimeric antibody | 4H6-mHvKv-IgG1 | 56 | 57 | Human IgG1 |

TABLE 1-continued

| Type | Antibody name | VH SEQ ID NO: | VL SEQ ID NO: | Constant regions |
| --- | --- | --- | --- | --- |
| based on 4H6 | | | | |
| Humanized antibodies based on 4H6 | 4H6-H1K1-IgG4 | 44 | 48 | Human IgG4 |
| | 4H6-H2K1-IgG4 | 45 | 48 | Human IgG4 |
| | 4H6-H3K1-IgG4 | 46 | 48 | Human IgG4 |
| | 4H6-H4K1-IgG4 | 47 | 48 | Human IgG4 |
| | 4H6-H1K2-IgG4 | 44 | 49 | Human IgG4 |
| | 4H6-H2K2-IgG4 | 45 | 49 | Human IgG4 |
| | 4H6-H3K2-IgG4 | 46 | 49 | Human IgG4 |
| | 4H6-H4K2-IgG4 | 47 | 49 | Human IgG4 |
| | 4H6-H1K3-IgG4 | 44 | 50 | Human IgG4 |
| | 4H6-H2K3-IgG4 | 45 | 50 | Human IgG4 |
| | 4H6-H3K3-IgG4 | 46 | 50 | Human IgG4 |
| | 4H6-H4K3-IgG4 | 47 | 50 | Human IgG4 |
| | 4H6-H1K4-IgG4 | 44 | 51 | Human IgG4 |
| | 4H6-H2K4-IgG4 | 45 | 51 | Human IgG4 |
| | 4H6-H3K4-IgG4 | 46 | 51 | Human IgG4 |
| | 4H6-H4K4-IgG4 | 47 | 51 | Human IgG4 |
| Chimeric antibody based on 7F10 | 7F10-mHvKv-IgG1-N297A | 52 | 53 | Human IgG1 with N297A mutation |
| Humanized antibodies based on 7F10 | 7F10-H1K1-IgG4 | 30 | 33 | Human IgG4 |
| | 7F10-H1K2-IgG4 | 30 | 34 | Human IgG4 |
| | 7F10-H1K3-IgG4 | 30 | 35 | Human IgG4 |
| | 7F10-H1K4-IgG4 | 30 | 36 | Human IgG4 |
| | 7F10-H2K1-IgG4 | 31 | 33 | Human IgG4 |
| | 7F10-H2K2-IgG4 | 31 | 34 | Human IgG4 |
| | 7F10-H2K3-IgG4 | 31 | 35 | Human IgG4 |
| | 7F10-H2K4-IgG4 | 31 | 36 | Human IgG4 |
| | 7F10-H3K1-IgG4 | 32 | 33 | Human IgG4 |
| | 7F10-H3K2-IgG4 | 32 | 34 | Human IgG4 |
| | 7F10-H3K3-IgG4 | 32 | 35 | Human IgG4 |
| | 7F10-H3K4-IgG4 | 32 | 36 | Human IgG4 |

Humanization percentage means the percentage identity of the heavy chain or light chain variable region sequence as compared to human antibody sequences in International Immunogenetics Information System (IMGT) database. The top hit means that the heavy chain or light chain variable region sequence is closer to a particular species than to other species. For example, top hit to human means that the sequence is closer to human than to other species. Top hit to human and *Macaca fascicularis* means that the sequence has the same percentage identity to the human sequence and the *Macaca fascicularis* sequence, and these percentages identities are highest as compared to the sequences of other species. In some embodiments, humanization percentage is greater than 80%, 81%, 82%, 83%, 84%, 85%, 86%, 87%, 88%, 89%, 90%, 91%, 92%, 93%, 94%, or 95%. A detailed description regarding how to determine humanization percentage and how to determine top hits is known in the art, and is described, e.g., in Jones, et al. "The INNs and outs of antibody nonproprietary names." MAbs. Vol. 8. No. 1. Taylor & Francis, 2016, which is incorporated herein by reference in its entirety. A high humanization percentage often has various advantages, e.g., more safe and more effective in humans, more likely to be tolerated by a human subject, and/or less likely to have side effects.

Furthermore, in some embodiments, the antibodies or antigen-binding fragments thereof described herein can also contain one, two, or three heavy chain variable region CDRs selected from the group of SEQ ID NOs: 1-3, SEQ ID NOs: 7-9, SEQ ID NOs: 13-15, SEQ ID NOs: 19, 20, 3, SEQ ID NOs: 22, 23, 9, and SEQ ID NOs: 24, 25, 15; and/or one, two, or three light chain variable region CDRs selected from the group of SEQ ID NOs: 4-6, SEQ ID Nos: 10-12, SEQ ID NOs: 16-18, and SEQ ID Nos: 4, 21, 6.

In some embodiments, the antibodies can have a heavy chain variable region (VH) comprising complementarity determining regions (CDRs) 1, 2, 3, wherein the CDR1 region comprises or consists of an amino acid sequence that is at least 80%, 85%, 90%, or 95% identical to a selected VH CDR1 amino acid sequence, the CDR2 region comprises or consists of an amino acid sequence that is at least 80%, 85%, 90%, or 95% identical to a selected VH CDR2 amino acid sequence, and the CDR3 region comprises or consists of an amino acid sequence that is at least 80%, 85%, 90%, or 95% identical to a selected VH CDR3 amino acid sequence, and a light chain variable region (VL) comprising CDRs 1, 2, 3, wherein the CDR1 region comprises or consists of an amino acid sequence that is at least 80%, 85%, 90%, or 95% identical to a selected VL CDR1 amino acid sequence, the CDR2 region comprises or consists of an amino acid sequence that is at least 80%, 85%, 90%, or 95% identical to a selected VL CDR2 amino acid sequence, and the CDR3 region comprises or consists of an amino acid sequence that is at least 80%, 85%, 90%, or 95% identical to a selected VL CDR3 amino acid sequence. The selected VH CDRs 1, 2, 3 amino acid sequences and the selected VL CDRs, 1, 2, 3 amino acid sequences are shown in FIG. 16 (Kabat CDR) and FIG. 17 (Chothia CDR).

In some embodiments, the antibody or an antigen-binding fragment described herein can contain a heavy chain variable domain containing one, two, or three of the CDRs of SEQ ID NO: 1 with zero, one or two amino acid insertions, deletions, or substitutions; SEQ ID NO: 2 with zero, one or two amino acid insertions, deletions, or substitutions; SEQ ID NO: 3 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 7 with zero, one or two amino acid insertions, deletions, or substitutions; SEQ ID NO: 8 with zero, one or two amino acid insertions, deletions, or substitutions; SEQ ID NO: 9 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 13 with zero, one or two amino acid insertions, deletions, or substitutions; SEQ ID NO: 14 with zero, one or two amino acid insertions, deletions, or substitutions; SEQ ID NO: 15 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 19 with zero, one or two amino acid insertions, deletions, or substitutions; SEQ ID NO: 20 with zero, one or two amino acid insertions, deletions, or substitutions; SEQ ID NO: 3 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 22 with zero, one or two amino acid insertions, deletions, or substitutions; SEQ ID NO: 23 with zero, one or two amino acid insertions, deletions, or substitutions; SEQ ID NO: 9 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 24 with zero, one or two amino acid insertions, deletions, or substitutions; SEQ ID NO: 25 with zero, one or two amino acid insertions, deletions, or substitutions; SEQ ID NO: 15 with zero, one or two amino acid insertions, deletions, or substitutions.

In some embodiments, the antibody or an antigen-binding fragment described herein can contain a light chain variable domain containing one, two, or three of the CDRs of SEQ ID NO: 4 with zero, one or two amino acid insertions, deletions, or substitutions; SEQ ID NO: 5 with zero, one or two amino acid insertions, deletions, or substitutions; SEQ ID NO: 6 with zero, one or two amino acid insertions, deletions, or substitutions.

In some embodiments, the antibody or an antigen-binding fragment described herein can contain a light chain variable domain containing one, two, or three of the CDRs of SEQ ID NO: 10 with zero, one or two amino acid insertions, deletions, or substitutions; SEQ ID NO: 11 with zero, one or two amino acid insertions, deletions, or substitutions; SEQ ID NO: 12 with zero, one or two amino acid insertions, deletions, or substitutions.

In some embodiments, the antibody or an antigen-binding fragment described herein can contain a light chain variable domain containing one, two, or three of the CDRs of SEQ ID NO: 16 with zero, one or two amino acid insertions, deletions, or substitutions; SEQ ID NO: 17 with zero, one or two amino acid insertions, deletions, or substitutions; SEQ ID NO: 18 with zero, one or two amino acid insertions, deletions, or substitutions.

In some embodiments, the antibody or an antigen-binding fragment described herein can contain a light chain variable domain containing one, two, or three of the CDRs of SEQ ID NO: 4 with zero, one or two amino acid insertions, deletions, or substitutions; SEQ ID NO: 21 with zero, one or two amino acid insertions, deletions, or substitutions; SEQ ID NO: 6 with zero, one or two amino acid insertions, deletions, or substitutions.

The insertions, deletions, and substitutions can be within the CDR sequence, or at one or both terminal ends of the CDR sequence.

The disclosure also provides antibodies or antigen-binding fragments thereof that bind to CD40. The antibodies or antigen-binding fragments thereof contain a heavy chain variable region (VH) comprising or consisting of an amino acid sequence that is at least 80%, 85%, 90%, or 95% identical to a selected VH sequence, and a light chain variable region (VL) comprising or consisting of an amino acid sequence that is at least 80%, 85%, 90%, or 95% identical to a selected VL sequence. In some embodiments, the selected VH sequence is SEQ ID NO: 30, 31, 32, or 52, and the selected VL sequence is SEQ ID NO: 33, 34, 35, 36, or 53. In some embodiments, the selected VH sequence is SEQ ID NO: 37, 38, 39, 40, or 54 and the selected VL sequence is SEQ ID NO: 41, 42, 43, or 55. In some embodiments, the selected VH sequence is SEQ ID NO: 44, 45, 46, 47, or 56, and the selected VL sequence is SEQ ID NO: 48, 49, 50, 51, or 57.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The disclosure also provides nucleic acid comprising a polynucleotide encoding a polypeptide comprising an immunoglobulin heavy chain or an immunoglobulin light chain. The immunoglobulin heavy chain or immunoglobulin light chain comprises CDRs as shown in FIG. 16 or FIG. 17, or have sequences as shown in FIGS. 19-22. When the polypeptides are paired with corresponding polypeptide (e.g., a corresponding heavy chain variable region or a corresponding light chain variable region), the paired polypeptides bind to CD40 (e.g., human CD40).

The anti-CD40 antibodies and antigen-binding fragments can also be antibody variants (including derivatives and conjugates) of antibodies or antibody fragments and multi-specific (e.g., bi-specific) antibodies or antibody fragments. Additional antibodies provided herein are polyclonal, monoclonal, multi-specific (multimeric, e.g., bi-specific), human antibodies, chimeric antibodies (e.g., human-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), class (e.g., IgG1, IgG2, IgG3, IgG4, IgA1, and IgA2), or subclass. In some embodiments, the antibody or antigen-binding fragment thereof is an IgG antibody or antigen-binding fragment thereof.

Fragments of antibodies are suitable for use in the methods provided so long as they retain the desired affinity and specificity of the full-length antibody. Thus, a fragment of an antibody that binds to CD40 will retain an ability to bind to CD40. An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site.

Single-chain Fv or (scFv) antibody fragments comprise the VH and VL domains (or regions) of antibody, wherein these domains are present in a single polypeptide chain. Generally, the scFv polypeptide further comprises a polypeptide linker between the VH and VL domains, which enables the scFv to form the desired structure for antigen binding.

The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

Diabodies are small antibody fragments with two antigen-binding sites, which fragments comprise a VH connected to a VL in the same polypeptide chain (VH and VL). By using a linker that is too short to allow pairing between the two domains on the same chain, the domains are forced to pair with the complementary domains of another chain and create two antigen-binding sites.

Linear antibodies comprise a pair of tandem Fd segments (VH-CH1-VH-CH1) which, together with complementary light chain polypeptides, form a pair of antigen binding regions. Linear antibodies can be bispecific or monospecific.

Antibodies and antibody fragments of the present disclosure can be modified in the Fc region to provide desired effector functions or serum half-life.

Multimerization of antibodies may be accomplished through natural aggregation of antibodies or through chemical or recombinant linking techniques known in the art. For example, some percentage of purified antibody preparations (e.g., purified IgG$_1$ molecules) spontaneously form protein aggregates containing antibody homodimers and other higher-order antibody multimers.

Alternatively, antibody homodimers may be formed through chemical linkage techniques known in the art. For example, heterobifunctional crosslinking agents including, but not limited to SMCC (succinimidyl 4-(maleimidomethyl)cyclohexane-1-carboxylate) and SATA (N-succinimidyl S-acethylthio-acetate) can be used to form antibody multimers. An exemplary protocol for the formation of antibody homodimers is described in Ghetie et al. (*Proc. Natl. Acad. Sci. U.S.A.* 94: 7509-7514, 1997). Antibody homodimers can be converted to Fab'2 homodimers through digestion with pepsin. Another way to form antibody homodimers is through the use of the autophilic T15 peptide described in Zhao et al. (*J. Immunol.* 25:396-404, 2002).

In some embodiments, the multi-specific antibody is a bi-specific antibody. Bi-specific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety.

Bi-specific antibodies include cross-linked or "heteroconjugate" antibodies. For example, one of the antibodies in the heteroconjugate can be coupled to avidin and the other to biotin. Heteroconjugate antibodies can also be made using any convenient cross-linking methods. Suitable cross-linking agents and cross-linking techniques are well known in the art and are disclosed in U.S. Pat. No. 4,676,980, which is incorporated herein by reference in its entirety.

Methods for generating bi-specific antibodies from antibody fragments are also known in the art. For example, bi-specific antibodies can be prepared using chemical linkage. Brennan et al. (Science 229:81, 1985) describes a procedure where intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab' TNB derivatives is then reconverted to the Fab' thiol by reduction with mercaptoethylamine, and is mixed with an equimolar amount of another Fab' TNB derivative to form the bi-specific antibody.

Any of the antibodies or antigen-binding fragments described herein may be conjugated to a stabilizing molecule (e.g., a molecule that increases the half-life of the antibody or antigen-binding fragment thereof in a subject or in solution). Non-limiting examples of stabilizing molecules include: a polymer (e.g., a polyethylene glycol) or a protein (e.g., serum albumin, such as human serum albumin). The conjugation of a stabilizing molecule can increase the half-life or extend the biological activity of an antibody or an antigen-binding fragment in vitro (e.g., in tissue culture or when stored as a pharmaceutical composition) or in vivo (e.g., in a human).

In some embodiments, the antibodies or antigen-binding fragments described herein can be conjugated to a therapeutic agent. The antibody-drug conjugate comprising the antibody or antigen-binding fragment thereof can covalently or non-covalently bind to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

Antibody Characteristics

The antibodies or antigen-binding fragments thereof described herein can block the binding between CD40 and CD40 ligands (e.g., CD154).

The antibodies or antigen-binding fragments thereof as described herein can be CD40 agonist or antagonist. In some embodiments, by binding to CD40, the antibody can inhibit CD40 signaling pathway. In some embodiments, the antibody can upregulate immune response or downregulate immune response.

In some embodiments, the antibodies or antigen-binding fragments thereof as described herein can increase immune response, activity or number of immune cells (e.g., T cells, CD8+ T cells, CD4+ T cells, macrophages, antigen presenting cells) by at least 10%, 20%, 30%, 40%, 50%, 60%, 70%, 80%, 90%, 100%, 2 folds, 3 folds, 5 folds, 10 folds, or 20 folds. In some embodiments, the antibodies or antigen-binding fragments thereof as described herein can decrease the activity or number of immune cells (e.g., T cells, CD8+ T cells, CD4+ T cells, macrophages, antigen presenting cells) by at least 10%, 20%, 30%, 40%, 50%, 60%, 70%, 80%, 90%, 100%, 2 folds, 3 folds, 5 folds, 10 folds, or 20 folds.

In some implementations, the antibody (or antigen-binding fragments thereof) specifically binds to CD40 (e.g., human CD40, monkey CD40 (e.g., rhesus macaques, *Macaca fascicularis*), mouse CD40, and/or chimeric CD40) with a dissociation rate (koff) of less than 0.1 s$^{-1}$, less than 0.01 s$^{-1}$, less than 0.001 s$^{-1}$, less than 0.0001 s$^{-1}$, or less than 0.00001 s$^{-1}$. In some embodiments, the dissociation rate (koff) is greater than 0.01 s$^{-1}$, greater than 0.001 s$^{-1}$, greater than 0.0001 s$^{-1}$, greater than 0.00001 s$^{-1}$, or greater than 0.000001 s$^{-1}$.

In some embodiments, kinetic association rates (kon) is greater than $1\times10^2$/Ms, greater than $1\times10^3$/Ms, greater than $1\times10^4$/Ms, greater than $1\times10^5$/Ms, or greater than $1\times10^6$/Ms. In some embodiments, kinetic association rates (kon) is less than $1\times10^5$/Ms, less than $1\times10^6$/Ms, or less than $1\times10^7$/Ms.

Affinities can be deduced from the quotient of the kinetic rate constants (KD=koff/kon). In some embodiments, KD is less than $1\times10^{-6}$ M, less than $1\times10^{-7}$ M, less than $1\times10^{-8}$ M, less than $1\times10^{-9}$ M, or less than $1\times10^{-10}$ M. In some embodiments, the KD is less than 50 nM, 30 nM, 20 nM, 15 nM, 10 nM, 9 nM, 8 nM, 7 nM, 6 nM, 5 nM, 4 nM, 3 nM, 2 nM, or 1 nM. In some embodiments, KD is greater than $1\times10^{-7}$M, greater than $1\times10^{-8}$M, greater than $1\times10^{-9}$M, greater than $1\times10^{-10}$ M, greater than $1\times10^{11}$ M, or greater than $1\times10^{-12}$ M. In some embodiments, the antibody binds to human CD40 with KD less than or equal to about 6 nM.

General techniques for measuring the affinity of an antibody for an antigen include, e.g., ELISA, RIA, and surface plasmon resonance (SPR). In some embodiments, the antibody binds to human CD40 (SEQ ID NO: 26), monkey CD40 (e.g., rhesus macaque CD40, SEQ ID NO: 28), chimeric CD40 (SEQ ID NO: 29), and/or mouse CD40 (SEQ ID NO: 27). In some embodiments, the antibody does not bind to human CD40 (SEQ ID NO: 26), monkey CD40 (e.g., rhesus macaque CD40, SEQ ID NO: 28; cynomolgus CD40), chimeric CD40 (SEQ ID NO: 29); and/or mouse CD40 (SEQ ID NO: 27).

In some embodiments, thermal stabilities are determined. The antibodies or antigen binding fragments as described herein can have a Tm greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, Tm is less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibody has a tumor growth inhibition percentage (TGI %) that is greater than 10%, 20%, 30%, 40%, 50%, 60%, 70%, 80%, 90%, 100%, 110%, 120%, 130%, 140%, 150%, 160%, 170%, 180%, 190%, or 200%. In some embodiments, the antibody has a tumor growth inhibition percentage that is less than 60%, 70%, 80%, 90%, 100%, 110%, 120%, 130%, 140%, 150%, 160%, 170%, 180%, 190%, or 200%. The TGI % can be determined, e.g., at 3, 4, 5, 6, 7, 8, 9, 10, 11, 12, 13, 14, 15, 16, 17, 18, 19, 20, 21, 22, 23, 24, 25, 26, 27, 28, 29, or 30 days after the treatment starts, or 1, 2, 3, 4, 5, 6, 7, 8, 9, 10, 11, or 12 months after the treatment starts. As used herein, the tumor growth inhibition percentage (TGI %) is calculated using the following formula:

$$TGI\ (\%)=[1-(Ti-T0)/(Vi-V0)]\times 100$$

Ti is the average tumor volume in the treatment group on day i. T0 is the average tumor volume in the treatment group on day zero. Vi is the average tumor volume in the control group on day i. V0 is the average tumor volume in the control group on day zero.

In some embodiments, the antibodies or antigen-binding fragments thereof as described herein are CD40 antagonist. In some embodiments, the antibodies or antigen binding fragments decrease CD40 signal transduction in a target cell that expresses CD40.

In some embodiments, the antibodies or antigen binding fragments can enhance APC (e.g., DC cell) function, for example, inducing surface expression of costimulatory and MHC molecules, inducing production of proinflammatory cytokines, and/or enhancing T cell triggering function.

In some embodiments, the antibodies or antigen binding fragments can bind to tumor cells that express CD40. In some embodiments, the antibodies or antigen binding fragments can induce complement mediated cytotoxicity (CMC) and/or antibody dependent cellular cytoxicity (ADCC), and kill the tumor cell.

In some embodiments, the antibodies or antigen binding fragments have a functional Fc region. In some embodiments, effector function of a functional Fc region is antibody-dependent cell-mediated cytotoxicity (ADCC). In some embodiments, effector function of a functional Fc region is phagocytosis. In some embodiments, effector function of a functional Fc region is ADCC and phagocytosis.

In some embodiments, the antibodies or antigen binding fragments can induce complement mediated cytotoxicity (CMC).

In some embodiments, the Fc region is human IgG1, human IgG2, human IgG3, or human IgG4.

In some embodiments, the antibodies or antigen binding fragments do not have a functional Fc region. For example, the antibodies or antigen binding fragments are Fab, Fab', F(ab')2, and Fv fragments. In some embodiments, the Fc region has LALA mutations (L234A and L235A mutations in EU numbering), or LALA-PG mutations (L234A, L235A, P329G mutations in EU numbering).

Methods of Making Anti-CD40 Antibodies

An isolated fragment of human CD40 can be used as an immunogen to generate antibodies using standard techniques for polyclonal and monoclonal antibody preparation. Polyclonal antibodies can be raised in animals by multiple injections (e.g., subcutaneous or intraperitoneal injections) of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence of CD40 and encompasses an epitope of the protein such that an antibody raised against the peptide forms a specific immune complex with the protein. As described above, the full length sequence of human CD40 is known in the art (SEQ ID NO: 26).

An immunogen typically is used to prepare antibodies by immunizing a suitable subject (e.g., human or transgenic animal expressing at least one human immunoglobulin locus). An appropriate immunogenic preparation can contain, for example, a recombinantly-expressed or a chemically-synthesized polypeptide (e.g., a fragment of human CD40). The preparation can further include an adjuvant, such as Freund's complete or incomplete adjuvant, or a similar immunostimulatory agent.

Polyclonal antibodies can be prepared as described above by immunizing a suitable subject with a CD40 polypeptide, or an antigenic peptide thereof (e.g., part of CD40) as an immunogen. The antibody titer in the immunized subject can be monitored over time by standard techniques, such as with an enzyme-linked immunosorbent assay (ELISA) using the immobilized CD40 polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, N.Y.). Hybridoma cells producing a monoclonal antibody are detected by screening the hybridoma culture supernatants for antibodies that bind the polypeptide or epitope of interest, e.g., using a standard ELISA assay.

Variants of the antibodies or antigen-binding fragments described herein can be prepared by introducing appropriate nucleotide changes into the DNA encoding a human, humanized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein, e.g., CD40. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human antibodies.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs.

A humanized antibody, typically has a human framework (FR) grafted with non-human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed by e.g., substituting rodent CDRs or CDR sequences for the corresponding sequences of a human antibody. These methods are described in e.g., Jones et al., Nature, 321:522-525 (1986);

Riechmann et al., Nature, 332:323-327 (1988); Verhoeyen et al., Science, 239:1534-1536 (1988); each of which is incorporated by reference herein in its entirety. Accordingly, "humanized" antibodies are chimeric antibodies wherein substantially less than an intact human V domain has been substituted by the corresponding sequence from a non-human species. In practice, humanized antibodies are typically mouse antibodies in which some CDR residues and some FR residues are substituted by residues from analogous sites in human antibodies.

The choice of human VH and VL domains to be used in making the humanized antibodies is very important for reducing immunogenicity. According to the so-called "best-fit" method, the sequence of the V domain of a mouse antibody is screened against the entire library of known human-domain sequences. The human sequence which is closest to that of the mouse is then accepted as the human FR for the humanized antibody (Sims et al., J. Immunol., 151:2296 (1993); Chothia et al., J. Mol. Biol., 196:901 (1987)).

It is further important that antibodies be humanized with retention of high specificity and affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Ordinarily, amino acid sequence variants of the human, humanized, or chimeric anti-CD40 antibody will contain an amino acid sequence having at least 75%, 80%, 85%, 90%, 95%, 96%, 97%, 98%, or 99% percent identity with a sequence present in the light or heavy chain of the original antibody.

Identity or homology with respect to an original sequence is usually the percentage of amino acid residues present within the candidate sequence that are identical with a sequence present within the human, humanized, or chimeric anti-CD40 antibody or fragment, after aligning the sequences and introducing gaps, if necessary, to achieve the maximum percent sequence identity, and not considering any conservative substitutions as part of the sequence identity.

Additional modifications to the anti-CD40 antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al. (*Cancer Res.* 53:2560-2565, 1993). Alternatively, an antibody can be engineered which has dual Fc regions (see, for example, Stevenson et al., *Anti-Cancer Drug Design* 3:219-230, 1989).

In some embodiments, a covalent modification can be made to the anti-CD40 antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues; or position 314 in Kabat numbering); however, Asn297 may also be located about ±3 amino acids upstream or downstream of position 297, i.e., between positions 294 and 300, due to minor sequence variations in antibodies. Such fucosylation variants may have improved ADCC function. In some embodiments, to reduce glycan heterogeneity, the Fc region of the antibody can be further engineered to replace the Asparagine at position 297 with Alanine (N297A).

In some embodiments, to facilitate production efficiency by avoiding Fab-arm exchange, the Fc region of the antibodies was further engineered to replace the serine at position 228 (EU numbering) of IgG4 with proline (S228P). A detailed description regarding S228 mutation is described, e.g., in Silva et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469, which is incorporated by reference in its entirety.

Recombinant Vectors

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant antibody polypeptides or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some implementations, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. In the latter case, viral propagation generally will occur only in complementing virus packaging cells. Suitable systems are disclosed, for example, in Fisher-Hoch et al., 1989, Proc. Natl. Acad. Sci. USA 86:317-321; Flexner et al., 1989, Ann. N.Y. Acad Sci. 569:86-103; Flexner et al., 1990, Vaccine, 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques, 6:616-627, 1988; Rosenfeld et al., 1991, Science, 252:431-434; Kolls et al., 1994, Proc. Natl. Acad. Sci. USA, 91:215-219; Kass-Eisler et al., 1993, Proc. Natl. Acad. Sci. USA, 90:11498-11502; Guzman et al., 1993, Circulation, 88:2838-2848; and Guzman et al., 1993, Cir. Res., 73:1202-1207. Techniques for incorporating DNA into such expression systems are well known to those of ordinary skill in the art. The DNA may also be "naked," as described, for example, in Ulmer et al., 1993, Science, 259:1745-1749, and Cohen, 1993, Science, 259:1691-1692. The uptake of naked DNA may be increased by coating the DNA onto biodegradable beads that are efficiently transported into the cells.

For expression, the DNA insert comprising an antibody-encoding or polypeptide-encoding polynucleotide disclosed herein can be operatively linked to an appropriate promoter (e.g., a heterologous promoter), such as the phage lambda PL promoter, the E. coli lac, trp and tac promoters, the SV40 early and late promoters and promoters of retroviral LTRs, to name a few. Other suitable promoters are known to the skilled artisan. The expression constructs can further contain sites for transcription initiation, termination and, in the transcribed region, a ribosome binding site for translation. The coding portion of the mature transcripts expressed by the constructs may include a translation initiating at the beginning and a termination codon (UAA, UGA, or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces, and Salmonella typhimurium cells; fungal cells, such as yeast cells; insect cells such as Drosophila S2 and Spodoptera Sf9 cells; animal cells such as CHO, COS, Bowes melanoma, and HK 293 cells; and plant cells. Appropriate culture mediums and conditions for the host cells described herein are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWL-NEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use include the E. coli lad and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast Saccharomyces cerevisiae, a number of vectors containing constitutive or inducible promoters such as alpha factor, alcohol oxidase, and PGH may be used. For reviews, see Ausubel et al. (1989) Current Protocols in Molecular Biology, John Wiley & Sons, New York, N.Y, and Grant et al., Methods Enzymol., 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986), which is incorporated herein by reference in its entirety.

Transcription of DNA encoding an antibody of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide (e.g., antibody) can be expressed in a modified form, such as a fusion protein (e.g., a GST-fusion) or with a histidine-tag, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art.

Methods of Treatment

The antibodies or antigen-binding fragments thereof of the present disclosure can be used for various therapeutic purposes.

In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In one aspect, the disclosure features methods that include administering a therapeutically effective amount of an antibody or antigen-binding fragment thereof disclosed herein to a subject in need thereof (e.g., a subject having, or identified or diagnosed as having, a cancer), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the subject has Hodgkin's lymphoma. In some embodiments, the subject has triple-negative breast cancer (TNBC), gastric cancer, urothelial cancer, Merkel-cell carcinoma, or head and neck cancer. In some embodiments, the cancer is melanoma, pancreatic carcinoma, mesothelioma, hematological malignancies, especially Non-Hodgkin's lymphoma, lymphoma, chronic lymphocytic leukemia, or advanced solid tumors.

In some embodiments, the compositions and methods disclosed herein can be used for treatment of patients at risk for a cancer. Patients with cancer can be identified with various methods known in the art.

In one aspect, the disclosure provides methods for treating, preventing, or reducing the risk of developing disorders associated with an abnormal or unwanted immune response, e.g., an autoimmune disorder, e.g., by affecting the functional properties of the APC cells (e.g., by blocking the interaction between CD40 and CD40L). These autoimmune disorders include, but are not limited to, Alopecia areata, lupus, ankylosing spondylitis, Meniere's disease, antiphospholipid syndrome, mixed connective tissue disease, autoimmune Addison's disease, multiple sclerosis, autoimmune hemolytic anemia, myasthenia gravis, autoimmune hepatitis, pemphigus vulgaris, Behcet's disease, pernicious anemia, bullous pemphigoid, polyarthritis nodosa, cardiomyopathy, polychondritis, celiac sprue-dermatitis, polyglandular syndromes, chronic fatigue syndrome (CFIDS), polymyalgia rheumatica, chronic inflammatory demyelinating, polymyositis and dermatomyositis, chronic inflammatory polyneuropathy, primary agammaglobulinemia, Churg-Strauss syndrome, primary biliary cirrhosis, cicatricial pemphigoid, psoriasis, CREST syndrome, Raynaud's phenomenon, cold agglutinin disease, Reiter's syndrome, Crohn's disease, Rheumatic fever, discoid lupus, rheumatoid arthritis, Cryoglobulinemia sarcoidosis, fibromyalgia, scleroderma, Grave's disease, Sjógren's syndrome, Guillain-Barre, stiff-man syndrome, Hashimoto's thyroiditis, Takayasu arteritis, idiopathic pulmonary fibrosis, temporal arteritis/giant cell arteritis, idiopathic thrombocytopenia purpura (ITP), ulcerative colitis, IgA nephropathy, uveitis, diabetes (e.g., Type I), vasculitis, lichen planus, and vitiligo. The anti-CD40 antibodies or antigen-binding fragments thereof can also be administered to a subject to treat, prevent, or reduce the risk of developing disorders associated with an abnormal or unwanted immune response associated with cell, tissue or organ transplantation, e.g., renal, hepatic, and cardiac transplantation, e.g., graft versus host disease (GVHD), or to prevent allograft rejection. In some embodiments, the subject has Crohn's disease, ulcerative colitis or type 1 diabetes.

As used herein, by an "effective amount" is meant an amount or dosage sufficient to effect beneficial or desired results including halting, slowing, retarding, or inhibiting progression of a disease, e.g., an autoimmune disease or a cancer. An effective amount will vary depending upon, e.g., an age and a body weight of a subject to which the antibody, antigen binding fragment, antibody-encoding polynucleotide, vector comprising the polynucleotide, and/or compositions thereof is to be administered, a severity of symptoms and a route of administration, and thus administration can be determined on an individual basis.

An effective amount can be administered in one or more administrations. By way of example, an effective amount of an antibody or an antigen binding fragment is an amount sufficient to ameliorate, stop, stabilize, reverse, inhibit, slow and/or delay progression of an autoimmune disease or a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount of an antibody or antigen binding fragment may vary, depending on, inter alia, patient history as well as other factors such as the type (and/or dosage) of antibody used.

Effective amounts and schedules for administering the antibodies, antibody-encoding polynucleotides, and/or compositions disclosed herein may be determined empirically, and making such determinations is within the skill in the art. Those skilled in the art will understand that the dosage that must be administered will vary depending on, for example, the mammal that will receive the antibodies, antibody-encoding polynucleotides, and/or compositions disclosed herein, the route of administration, the particular type of antibodies, antibody-encoding polynucleotides, antigen binding fragments, and/or compositions disclosed herein used and other drugs being administered to the mammal. Guidance in selecting appropriate doses for antibody or antigen binding fragment can be found in the literature on therapeutic uses of antibodies and antigen binding fragments, e.g., Handbook of Monoclonal Antibodies, Ferrone et al., eds., Noges Publications, Park Ridge, N.J., 1985, ch. 22 and pp. 303-357; Smith et al., Antibodies in Human Diagnosis and Therapy, Haber et al., eds., Raven Press, New York, 1977, pp. 365-389.

A typical daily dosage of an effective amount of an antibody is 0.01 mg/kg to 100 mg/kg. In some embodiments, the dosage can be less than 100 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage can be greater than 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.1 mg/kg, 0.05 mg/kg, or 0.01 mg/kg. In some embodiments, the dosage is about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg.

In any of the methods described herein, the at least one antibody, antigen-binding fragment thereof, or pharmaceutical composition (e.g., any of the antibodies, antigen-binding fragments, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different antibodies and/or antigen-binding fragments are administered in the same composition (e.g., a liquid composition). In some embodiments, at least one antibody or antigen-binding fragment and at least one additional therapeutic agent are administered in the same composition (e.g., a liquid composition). In some embodiments, the at least one antibody or antigen-binding fragment and the at least one additional therapeutic agent are administered in two different compositions (e.g., a liquid composition containing at least one antibody or antigen-binding fragment and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to, or after administering the at least one antibody, antigen-binding antibody fragment, or pharmaceutical composition (e.g., any of the antibodies, antigen-binding antibody fragments, or pharmaceutical compositions described herein). In some embodiments, the one or more additional therapeutic agents and the at least one antibody, antigen-binding antibody fragment, or pharmaceutical composition (e.g., any of the antibodies, antigen-binding antibody fragments, or pharmaceutical compositions described herein) are administered to the subject such that there is an overlap in the bioactive period of the one or more additional therapeutic agents and the at least one antibody or antigen-binding fragment (e.g., any of the antibodies or antigen-binding fragments described herein) in the subject.

In some embodiments, the subject can be administered the at least one antibody, antigen-binding antibody fragment, or pharmaceutical composition (e.g., any of the antibodies, antigen-binding antibody fragments, or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years). A skilled medical professional may determine the length of the treatment period using any of the methods described herein for diagnosing or following the effectiveness of treatment (e.g., the observation of at least one symptom of cancer). As described herein, a skilled medical professional can also change the identity and number (e.g., increase or decrease) of antibodies or antigen-binding antibody fragments (and/or one or more additional therapeutic agents) administered to the subject and can also adjust (e.g., increase or decrease) the dosage or frequency of administration of at least one antibody or antigen-binding antibody fragment (and/or one or more additional therapeutic agents) to the subject based on an assessment of the effectiveness of the treatment (e.g., using any of the methods described herein and known in the art).

In some embodiments, one or more additional therapeutic agents can be administered to the subject. The additional therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1) (IDO1) (e.g., epacadostat).

In some embodiments, the additional therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the additional therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the additional therapeutic agent is an anti-OX40 antibody, an anti-PD-1 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody.

Pharmaceutical Compositions and Routes of Administration

Also provided herein are pharmaceutical compositions that contain at least one (e.g., one, two, three, or four) of the antibodies or antigen-binding fragments described herein. Two or more (e.g., two, three, or four) of any of the antibodies or antigen-binding fragments described herein can be present in a pharmaceutical composition in any combination. The pharmaceutical compositions may be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfate, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the antibody or antigen-binding fragment thereof can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions containing one or more of any of the antibodies or antigen-binding fragments described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a human). A therapeutically effective amount of the one or more (e.g., one, two, three, or four) antibodies or antigen-binding fragments thereof (e.g., any of the antibodies or antibody fragments described herein) will be an amount that treats the disease in a subject (e.g., kills cancer cells) in a subject (e.g., a human subject identified as having cancer), or a subject identified as being at risk of developing the disease (e.g., a subject who has previously developed cancer but now has been cured), decreases the severity, frequency, and/or duration of one or more symptoms of a disease in a subject (e.g., a human). The effectiveness and dosing of any of the antibodies or antigen-binding fragments described herein can be determined by a health care professional or veterinary professional using methods known in the art, as well as by the observation of one or more symptoms of disease in a subject (e.g., a human). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the antibodies or antigen-binding fragments described herein per kilogram of the subject's weight (e.g., about 1 µg/kg to about 500 mg/kg; about 100 µg/kg to about 500 mg/kg; about 100 µg/kg to about 50 mg/kg; about 10 µg/kg to about 5 mg/kg; about 10 µg/kg to about 0.5 mg/kg; or about 1 µg/kg to about 50 µg/kg). While these doses cover a broad range, one of ordinary skill in the art will understand that therapeutic agents, including antibodies and antigen-binding fragments thereof, vary in their potency, and effective amounts can be determined by methods known in the art. Typically, relatively low doses are administered at first, and the attending health care professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the antibody or antibody fragment in vivo.

The pharmaceutical compositions can be included in a container, pack, or dispenser together with instructions for administration. The disclosure also provides methods of manufacturing the antibodies or antigen binding fragments thereof for various uses as described herein.

EXAMPLES

The invention is further described in the following examples, which do not limit the scope of the invention described in the claims.

Example 1. Generating Mouse Anti-hCD40 Antibodies

Figure 2:
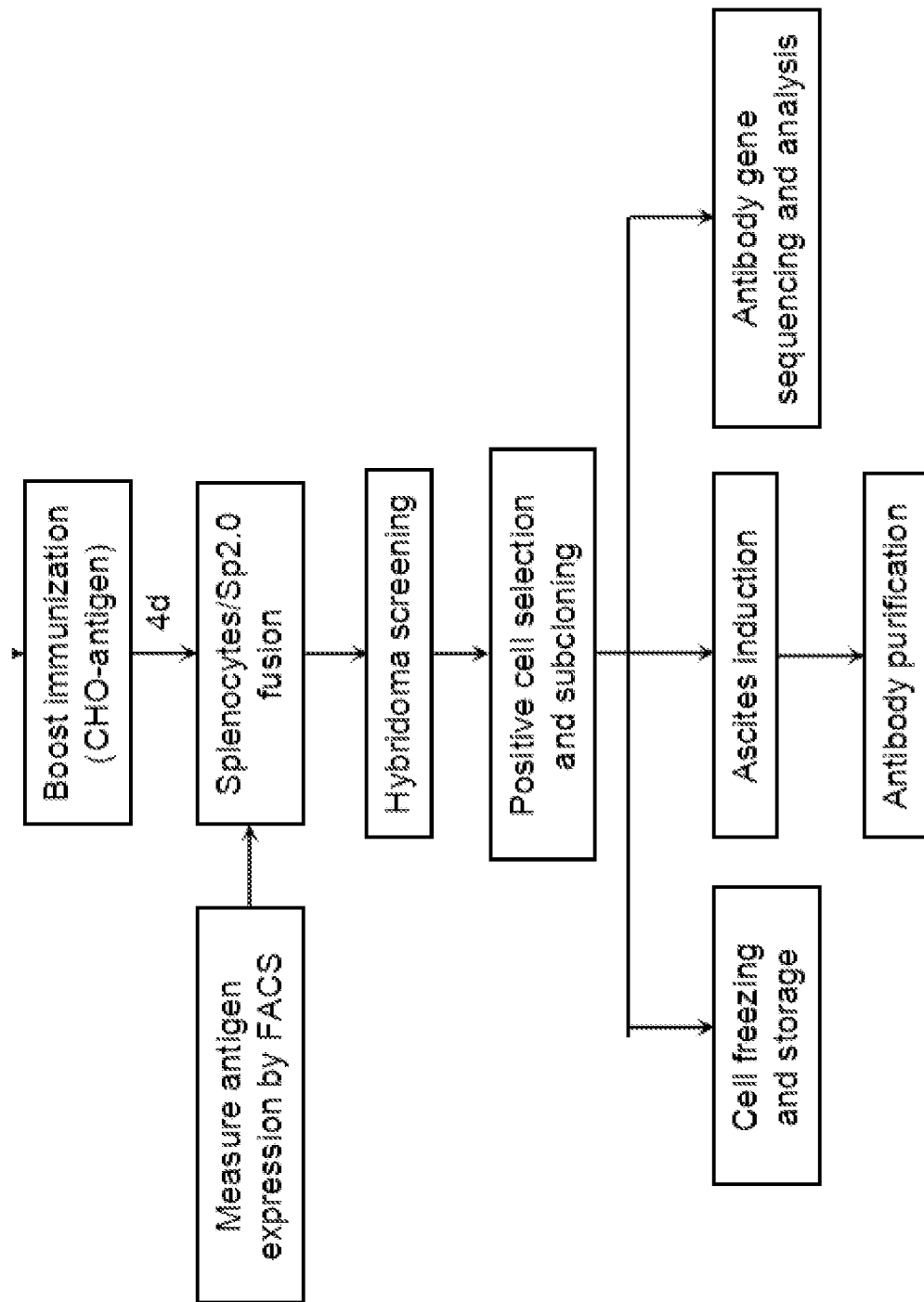
FIG. 2 is a flow chart showing the second part of an exemplary protocol of making anti-hCD40 antibodies.

To generate mouse antibodies against human CD40 (hCD40; SEQ ID NO: 26), 6-8 weeks old female BALB/c mice were immunized with human CD40. Anti-hCD40 antibodies were collected by the methods as described below and shown in FIG. 1 and FIG. 2.

Immunization of Mice 6-8 weeks old female BALB/c mice were immunized with His-tagged human CD40 proteins at 20 µg/mouse at a concentration of 100 µg/ml. The His-tagged human CD40 proteins were emulsified with adjuvant and injected at four positions on the back of the mice. For the first subcutaneous (s.c.) injection, the diluted antigen was emulsified with Complete Freund's Adjuvant (CFA) in equal volume. In the following subcutaneous injections, the protein was emulsified with Incomplete Freund's Adjuvant (IFA) in equal volume. Three days after the third injection or the booster immunization, blood (serum) was collected and analyzed for antibody titer using ELISA.

In another experiment, 6-8 weeks old female BALB/c mice were immunized by injecting the expression plasmid encoding human CD40 into the mice. The plasmids encoding the antigen were injected into the tibialis anterior muscle (intramuscular injection; i.m. injection) of the mice by using gene guns at the concentration of 1000 µg/ul at 60 µg per mouse. At least four injections were performed with at least 14 days between two injections. Blood (serum) was collected seven days after the last immunization and the serum was tested for antibody titer by ELISA.

Procedures to enhance immunization were also performed at least fourteen days after the previous immunization (either by injecting the plasmid or by injecting the proteins). CHO cells that express CD40 antigen on the surface were intravenously injected into the mice through tail veins. Spleen was then collected four days after the injection.

Fusion of SP2/0 Cells and Spleen Cells

Spleen tissues were grinded. Spleen cells were first selected by CD3c Microbeads and Anti-Mouse IgM Microbeads, and then fused with SP2/0 cells. The cells were then plated in 96-well plates with hypoxanthine-aminopterin-thymidine (HAT) medium.

Primary Screening of Hybridoma

Primary screening of the hybridoma supernatant in the 96-well plates was performed using Fluorescence-Activated Cell Sorting (FACS) pursuant to standard procedures. Chinese hamster ovary (CHO) cells were added to 96-well plates ($2 \times 10^4$ cells per well) before the screening. 50 µl of supernatant was used. The antibodies that were used in experiments were (1) Fluorescein (FITC)-conjugated AffiniPure $F(ab)_2$ Fragment Goat Anti-Mouse IgG, Fcγ Fragment Specific, and (2) Alexa Fluor® 647-conjugated AffiniPure $F(ab)_2$ Fragment Goat Anti-Human IgG, Fcγ Fragment Specific.

Sub-Cloning

Sub-cloning was performed using ClonePix2. In short, the positive wells identified during the primary screening were transferred to semisolid medium, and IgG positive clones were identified and tested. FITC anti-mouse IgG Fc antibody was used.

Ascites Fluid Antibodies $1 \times 10^6$ positive hybridoma cells were injected intraperitoneally to B-NDG™ mice (Beijing Biocytogen, Beijing, China; Cat #B-CM-002). Monoclonal antibodies were produced by growing hybridoma cells within the peritoneal cavity of the mouse. The hybridoma cells multiplied and produced ascites fluid in the abdomens of the mice. The fluid contained a high concentration of antibody which can be harvested for later use.

Purification of Antibodies

Antibodies in ascites fluid were purified using GE AKTA protein chromatography (GE Healthcare, Chicago, Ill., United States). 03-7F10 ("7F10"), 06-6A7 ("6A7"), 07-4H6 ("4H6"), 03-9D7 ("9D7"), 03-2A7 ("2A7"), and 03-9E11 ("9E11") were among the mouse antibodies produced by the methods described above.

The VH, VL and CDR regions of the antibodies were determined. The heavy chain CDR1, CDR2, CDR3, and light chain CDR1, CDR2, and CDR3 amino acid sequences of 7F10 are shown in SEQ ID NOs: 1-6 (Kabat numbering) or SEQ ID NOs: 19, 20, 3, 4, 21, 6 (Chothia numbering).

The heavy chain CDR1, CDR2, CDR3, and light chain CDR1, CDR2, and CDR3 amino acid sequences of 6A7 are shown in SEQ ID NOs: 7-12 (Kabat numbering) or SEQ ID NOs: 22, 23, 9, 10, 11, 12 (Chothia numbering).

The heavy chain CDR1, CDR2, CDR3, and light chain CDR1, CDR2, and CDR3 amino acid sequences of 4H6 are shown in SEQ ID NOs: 13-18 (Kabat numbering) or SEQ ID NOs: 24, 25, 15, 16, 17, 18 (Chothia numbering).

Example 2. Humanization of the Mice Antibodies

The starting point for humanization was the mouse antibodies (e.g., 7F10, 6A7, and 4H6). The amino acid sequences for the heavy chain variable region and the light chain variable region of these mouse antibodies were determined.

Three humanized heavy chain variable region variants (SEQ ID NOs: 30-32) and four humanized light chain variable region variants (SEQ ID NOs: 33-36) for 7F10 were constructed, containing different modifications or substitutions.

Four humanized heavy chain variable region variants (SEQ ID NOs: 37-40) and three humanized light chain variable region variants (SEQ ID NOs: 41-43) for 6A7 were constructed, containing different modifications or substitutions.

Four humanized heavy chain variable region variants (SEQ ID NOs: 44-47) and four humanized light chain variable region variants (SEQ ID NOs: 48-51) for 4H6 were constructed, containing different modifications or substitutions.

These humanized heavy chain variable region variants can be combined with any of the light chain variable region variants based on the same mouse antibody. For example, 6A7-H4 (SEQ ID NO: 40) can be combined with any humanized light chain variable region variant based on the same mouse antibody 6A7 (e.g., 6A7-K2 (SEQ ID NO: 42)), and the antibody is labeled accordingly (e.g., 6A7-H4K2).

Example 3. In Vitro Testing of the Mouse Anti-hCD40 Antibodies: Blocking the Binding of Human CD40 (hCD40) and Human CD40 Ligand (hCD40L)

Blocking assays were performed to determine whether the anti-hCD40 antibodies can block the binding between hCD40 and its ligand hCD40L.

The anti-hCD40 antibodies were collected from mouse ascites fluid and purified by chromatography. 25 µl CHO cells transiently transfected with human CD40 were added to each well in a plate. The purified antibodies were titrated to final concentrations of 50, 5, 0.5, 0.05, and 0.005 µg/ml. The titrated antibodies were added to each well at 25 µl per well at 4° C. and incubated for 30 minutes.

hCD40 ligand-hFc was expressed by H293T cells. 50 µl of hCD40L-hFc was added to each well (1:500). The cells with hCD40L-hFc and the antibodies were incubated at 4° C. for 15 minutes.

After being washed with phosphate-buffered saline (PBS) twice, 50 µl of PE labeled anti-mouse IgG Fc antibody (anti-mIgG Fc-PE) at 1:500 dilution and FITC-labeled anti-human IgG Fc antibody (anti-hIgG Fc-FITC) at 1:100 dilution were added into each well, and incubated for 30 minutes at 4° C., followed by PBS wash. The signals for FITC and PE were determined by flow cytometry.

Figure 3:
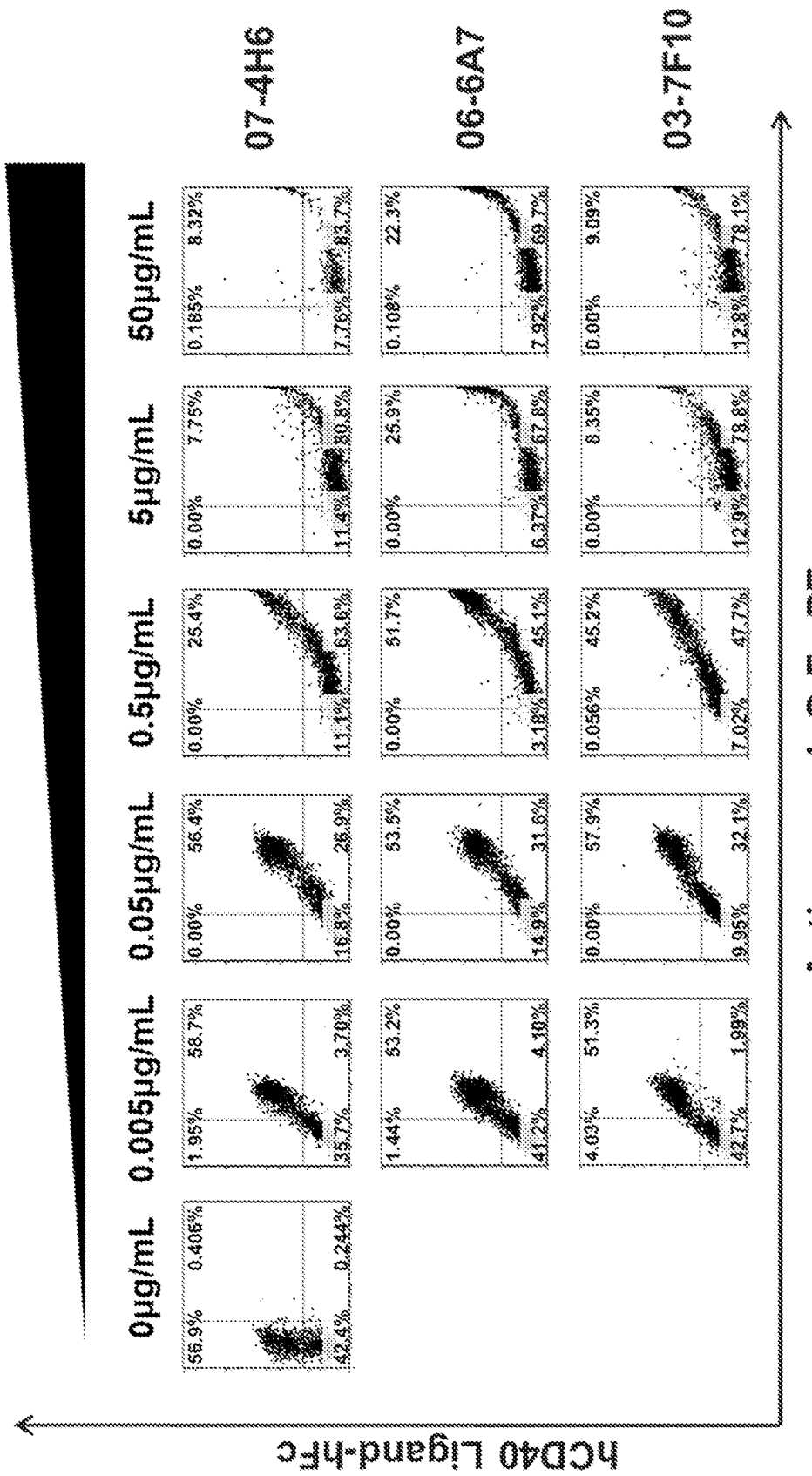
FIG. 3 is a set of flow cytometry graphs showing that the anti-hCD40 antibodies block the binding between hCD40 and hCD40 ligand.

As shown in FIG. 3, when the concentration of the mouse anti-hCD40 antibodies 03-7F10, 06-6A7, and 07-4H6 increased, the signal for cells binging to hCD40L decreased (y axis), while the signal for cells binding to the mouse anti-hCD40 antibodies increased, suggesting that the binding between human CD40 and human CD40L was blocked by the anti-hCD40 antibodies.

Example 4. Cross-Reactivity of Anti-hCD40 Antibodies Against Monkey, Mouse, and Human-Mouse Chimeric CD40

In each experiment, the CHO cells were transfected with mouse CD40 (mCD40, SEQ ID NO: 27), monkey (rhesus macaque) CD40 (rmCD40, SEQ ID NO: 28), or chimeric (mouse and human) CD40 (chiCD40, SEQ ID NO: 29). 25 µl CHO cells were added to each well. 25 µl purified anti-hCD40 antibodies (1 µg/ml) (7F10, 6A7, or 4H6) were added to each well and were incubated at 4° C. for 30 minutes.

After being washed with PBS (1200 rmp, 5 min) twice, 50 µl of FITC labeled anti-mouse IgG Fc antibody (anti-mIgG Fc-FITC) was added into each well 1:100 dilution, followed by incubated at 4° C. for 30 minutes, and then PBS wash (1200 rmp, 5 min). The signals for FITC were detected by flow cytometry.

Figure 4:
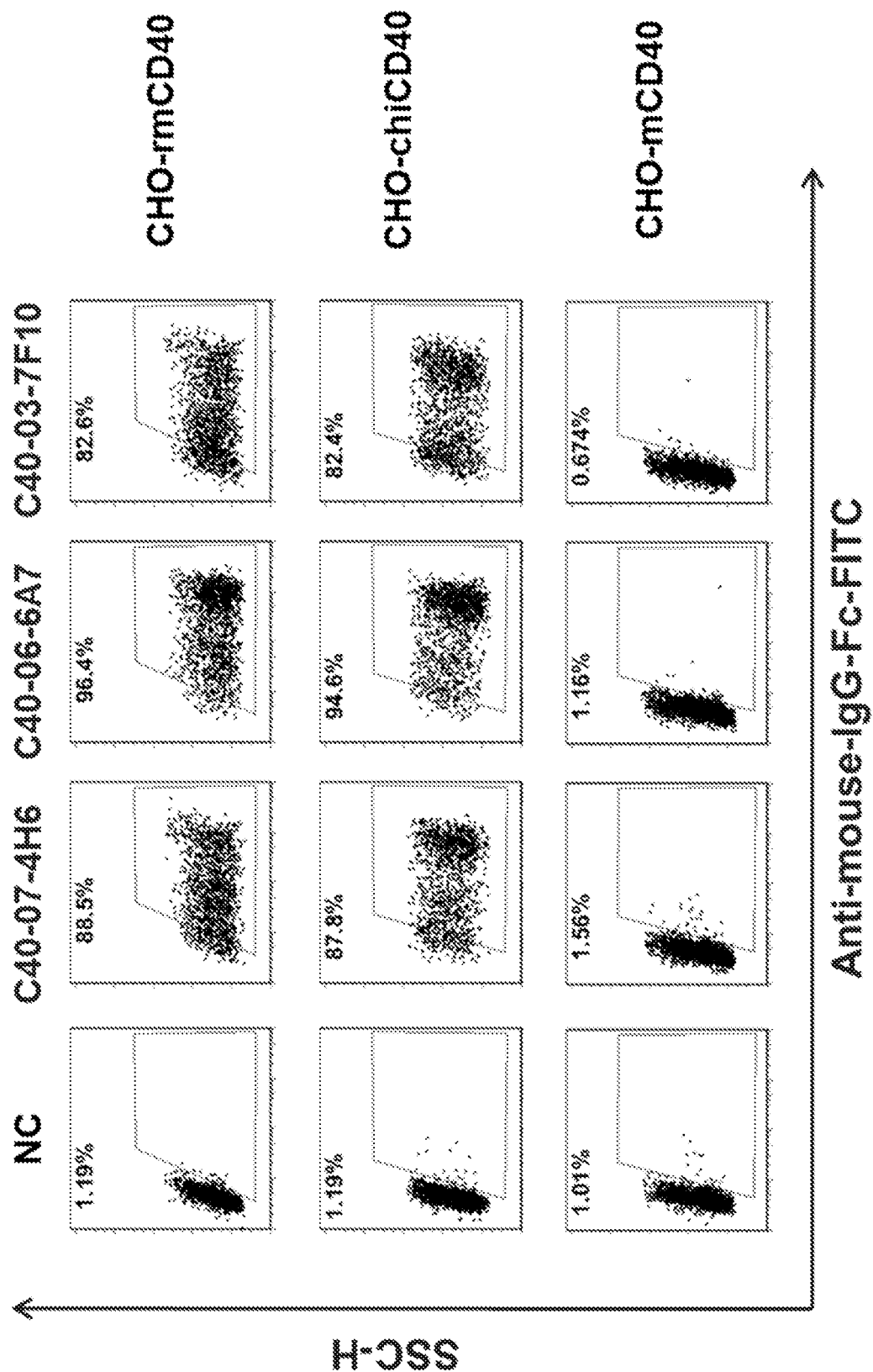
FIG. 4 is a set of graphs showing flow cytometry results of analyzing the anti-hCD40 antibodies' cross-reactivity with monkey CD40 (rmCD40), mouse CD40 (mCD40), and human-mouse chimeric CD40 (chiCD40). NC stands for negative control.

As shown in FIG. 4, 7F10, 6A7, and 4H6 did not cross react with mouse CD40, but had strong cross reactivity with rmCD40 and chimeric CD40. In FIG. 4, NC stands for negative control.

Example 5. Binding Affinity of Anti-hCD40 Antibodies

The binding affinity of the anti-hCD40 antibodies were measured using surface plasmon resonance (SPR) using Biacore (Biacore, INC, Piscataway N.J.) T200 biosensor equipped with pre-immobilized Protein A sensor chips.

Figure 5:
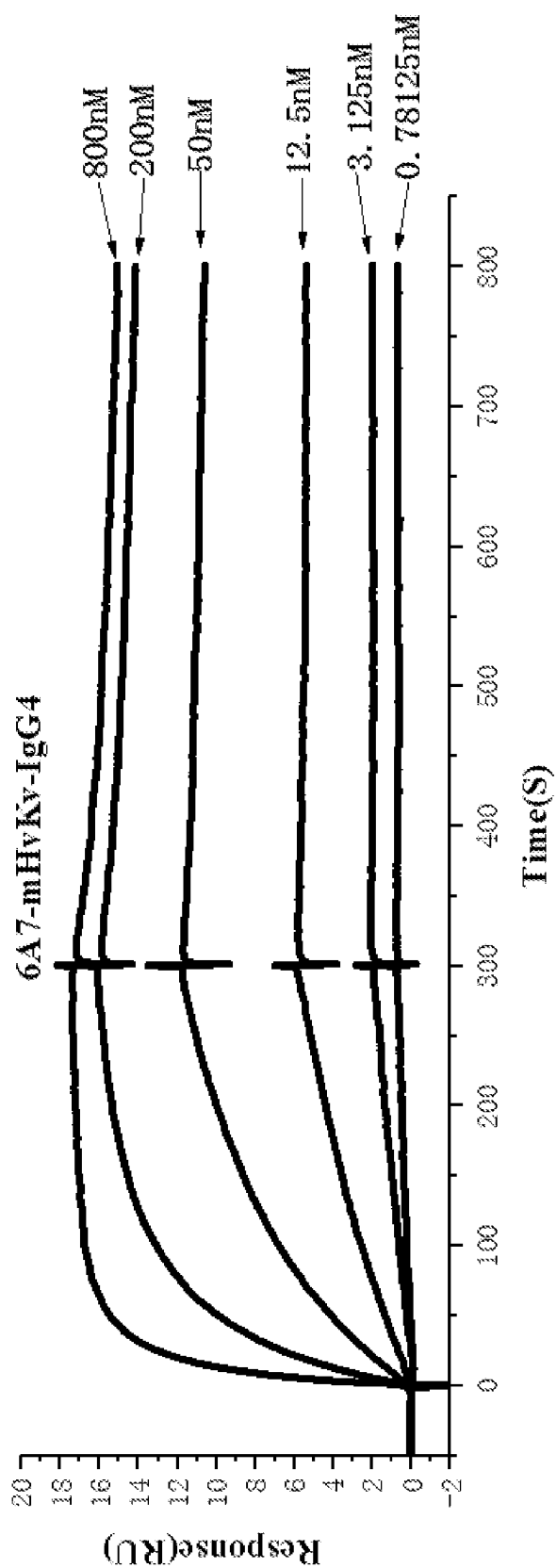
FIG. 5 is a graph showing the results of surface plasma resonance (SPR) using the chimeric anti-hCD40 antibody 6A7-mHvKv-IgG4 and human CD40.

Anti-hCD40 antibodies were collected by transfecting CHO—S cells and then purified. The antibodies (1 µg/mL) were injected into Biacore T200 biosensor at 10 µL/min for about 24-33 seconds to achieve to a desired protein density (about 44-57 response units (RU)). Histidine-tagged human CD40 proteins (hCD40-His) at the concentration of 800, 200, 50, 12.5, 3.125, 0.78125 nM were then injected at 30 µL/min for 300 seconds. Dissociation was monitored for 300 seconds. The chip was regenerated after the last injection of each titration with Glycine (pH 2.0, 30 µL/min for 12 seconds). The result for 6A7-mHvKv-IgG4 is shown in FIG. 5.

Kinetic association rates (kon) and dissociation rates (koff) were obtained simultaneously by fitting the data globally to a 1:1 Langmuir binding model (Karlsson, R. Roos, H. Fagerstam, L. Petersson, B., 1994. Methods Enzymology 6. 99-110) using Biacore T200 Evaluation Software 3.0. Affinities were deduced from the quotient of the kinetic rate constants (KD=koff/kon).

Figure 6:
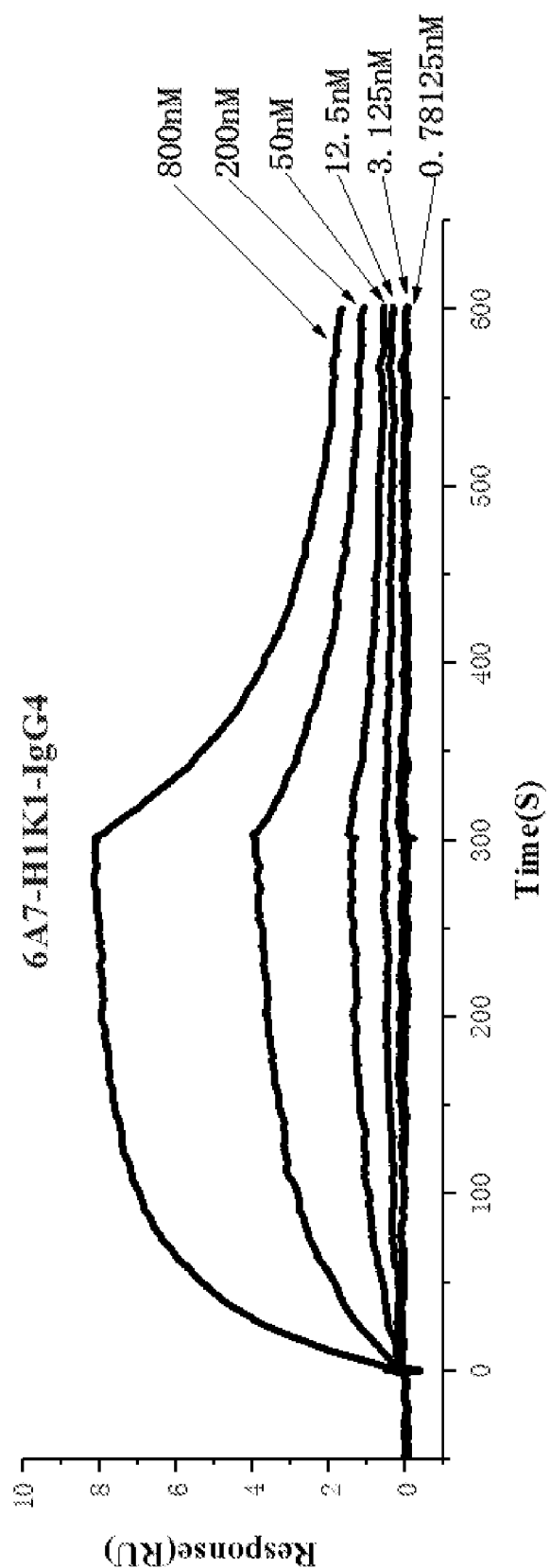
FIG. 6 is a graph showing the results of surface plasma resonance (SPR) using the humanized anti-hCD40 antibody 6A7-H1K1-IgG4 and human CD40.

As a person of ordinary skill in the art would understand, the same method with appropriate adjustments for parameters (e.g., antibody concentration) was performed for each tested antibody. For example, the graph showing the results of 6A7-H1K1-IgG4 is shown in FIG. 6. The results for the tested antibodies are summarized in the table below. The result for Dacetuzumab is also included for comparison purpose.

TABLE 2

| Anti-hCD40 antibodies | Association rate kon (1/Ms) | Dissociation rate koff (1/s) | Affinity KD (M) |
| --- | --- | --- | --- |
| Dacetuzumab | 4.17E+05 | 8.33E-03 | 2.00E-08 |
| 6A7-mHvKv-IgG4 | 9.94E+04 | 2.59E-04 | 2.60E-09 |
| 6A7-H1K1-IgG4 | 2.04E+04 | 5.71E-03 | 2.80E-07 |
| 6A7-H2K1-IgG4 | 2.37E+04 | 7.08E-03 | 2.98E-07 |
| 6A7-H3K1-IgG4 | 2.76E+04 | 5.74E-04 | 2.08E-08 |
| 6A7-H4K1-IgG4 | 2.39E+04 | 5.72E-04 | 2.39E-08 |
| 6A7-H1K2-IgG4 | 2.06E+04 | 3.86E-03 | 1.87E-07 |
| 6A7-H2K2-IgG4 | 2.63E+04 | 4.96E-03 | 1.89E-07 |
| 6A7-H3K2-IgG4 | 6.46E+04 | 3.71E-04 | 5.74E-09 |
| 6A7-H4K2-IgG4 | 1.05E+05 | 3.22E-04 | 3.06E-09 |
| 6A7-H1K3-IgG4 | 2.87E+04 | 3.90E-03 | 1.36E-07 |
| 6A7-H2K3-IgG4 | 4.53E+04 | 5.05E-03 | 1.11E-07 |
| 6A7-H3K3-IgG4 | 1.23E+05 | 3.56E-04 | 2.90E-09 |
| 6A7-H4K3-IgG4 | 1.07E+05 | 3.73E-04 | 3.49E-09 |
| 4H6-mHvKv-IgG1 | 5.612E+5 | 2.050E-02 | 3.652E-8 |
| 4H6-H1K1-IgG4 | 2.167E+04 | L673E-01 | 7.723E-06 |
| 4H6-H2K1-IgG4 | 5.074E+05 | 2.269E-01 | 4.472E-07 |
| 4H6-H3K1-IgG4 | 8.270E+05 | 3.420E-02 | 4.130E-07 |
| 4H6-H4K1-IgG4 | 1.850E+05 | 2.690E-02 | 1.450E-07 |
| 4H6-H1K2-IgG4 | 3.856E+05 | 6.319E-02 | 1.639E-07 |
| 4H6-H2K2-IgG4 | 4.138E+05 | 5.700E-02 | 1.378E-07 |
| 4H6-H3K2-IgG4 | 4.014E+05 | 2.152E-02 | 5.361E-08 |
| 4H6-H4K2-IgG4 | 3.918E+05 | 1.907E-02 | 4.866E-08 |
| 4H6-H1K3-IgG4 | 2.420E+05 | 5.540E-02 | 2.290E-07 |
| 4H6-H2K3-IgG4 | 2.600E+05 | 6.590E-02 | 2.530E-07 |
| 4H6-H3K3-IgG4 | 3.120E+05 | 2.860E-02 | 9.160E-08 |
| 4H6-H4K3-IgG4 | 3.266E+05 | 2.574E-02 | 7.881E-08 |
| 4H6-H1K4-IgG4 | 1.490E+05 | 6.950E-02 | 4.650E-07 |
| 4H6-H2K4-IgG4 | 1.960E+05 | 7.420E-02 | 3.780E-07 |
| 4H6-H3K4-IgG4 | 2.980E+05 | 2.820E-02 | 9.480E-08 |
| 4H6-H4K4-IgG4 | 3.125E+05 | 2.778E-02 | 8.891E-08 |
| 7F10-mHvKv-IgG1-N297A | 1.504E+05 | 2.924E-02 | 1.944E-07 |
| 7F10-H1K1-IgG4 | 1.769E+05 | 5.144E-02 | 2.908E-07 |
| 7F10-H1K2-IgG4 | 8.277E+04 | 4.915E-02 | 5.938E-07 |
| 7F10-H1K3-IgG4 | 7.312E+04 | 3.913E-02 | 5.351E-07 |
| 7F10-H1K4-IgG4 | 1.153E+05 | 3.208E-02 | 2.782E-07 |
| 7F10-H2K1-IgG4 | 1.205E+05 | 6.505E-02 | 5.397E-07 |
| 7F10-H2K2-IgG4 | 1.056E+05 | 5.337E-02 | 5.053E-07 |
| 7F10-H2K3-IgG4 | 1.720E+05 | 3.126E-02 | 1.817E-07 |
| 7F10-H2K4-IgG4 | 1.880E+05 | 3.801E-02 | 2.021E-07 |
| 7F10-H3K1-IgG4 | 1.320E+05 | 5.679E-02 | 4.302E-07 |
| 7F10-H3K2-IgG4 | 1.266E+05 | 4.817E-02 | 3.805E-07 |
| 7F10-H3K3-IgG4 | 1.320E+05 | 3.137E-02 | 2.376E-07 |
| 7F10-H3K4-IgG4 | 1.487E+05 | 2.737E-02 | 1.841E-07 |

Among these tested antibodies, 6A7-mHvKv-IgG4, 4H6-mHvKv-IgG1, and 7F10-mHvKv-IgG1-N297A are chimeric anti-hCD40 antibodies. The chimeric antibodies have the heavy chain variable domain and the light chain variable domain from the corresponding mouse anti-hCD40 antibodies, with the constant domains from human antibody (including, e.g., the CL, CH1, CH2, and CH3 domains). The term mHvKv indicates mouse heavy chain variable region and mouse light chain variable region.

The tested antibodies also include humanized antibodies. These tested humanized antibodies have human IgG4 antibody constant domains (including, e.g., the CL, CH1, CH2, and CH3 domains). The humanized variable domains of the heavy chain are numbered H1, H2, H3 etc.; and the humanized variable domains of the light chain are numbered K1, K2, K3 etc. The sequences of the humanized variable domains are summarized in FIGS. 19-21. For example, 7F10-H1K1-IgG4 is based on the mouse antibody 7F10 and has the humanized heavy chain variable domain H1 (SEQ ID NO: 30) and humanized light chain variable domain K1 (SEQ ID NO: 33). Similarly, 6A7-H3K2-IgG4 is based on mouse antibody 6A7 and has humanized heavy chain variable domain H3 (SEQ ID NO: 39) and humanized 6A7 light chain variable domain K2 (SEQ ID NO: 42).

The name and the sequences of the chimeric anti-CD40 antibodies and the humanized anti-CD40 antibodies are summarized in Table 1. A few tested antibodies have the N297A mutation (EU numbering) in the Fc region. The N297A mutation can lead to lack of glycosylation at N297 and thus loss of effector function.

Example 6. Binding Affinity of Anti-hCD40 Antibodies with mfCD40

The binding affinity of the anti-hCD40 antibodies with mfCD40 (*Macaca fascicularis*) were measured using surface plasmon resonance (SPR) using Biacore (Biacore, INC, Piscataway N.J.) T200 biosensor equipped with pre-immobilized Protein A sensor chips.

Anti-hCD40 antibodies were purified. The antibodies (0.5 µg/mL) were injected into Biacore T200 biosensor at 10 µL/min for about 18-26 seconds to achieve to a desired protein density (about 44-58 response units (RU)). Histidine-tagged mfCD40 proteins (mfCD40-His) (Acrobiosystems, Cat #: CD0-052H6) at the concentration of 200, 50, 12.5, 3.125 nM were then injected at 30 µL/min for 180 seconds. Dissociation was monitored for 300-600 seconds. The chip was regenerated after the last injection of each titration with Glycine (pH 2.0, 30 µL/min for 12 seconds).

Kinetic association rates (kon) and dissociation rates (koff) were obtained simultaneously by fitting the data globally to a 1:1 Langmuir binding model using Biacore T200 Evaluation Software 3.0. Affinities were deduced from the quotient of the kinetic rate constants (KD=koff/kon).

The results for the tested antibodies are summarized in the table below.

TABLE 3

| Anti-hCD40 antibodies | Association rate kon (1/Ms) | Dissociation rate koff (1/s) | Affinity KD (M) with mfCD40 |
|---|---|---|---|
| 4H6-H3K2-IgG4 | 5.700E+05 | 1.918E−02 | 3.365E−08 |
| 4H6-H4K2-IgG4 | 5.683E+05 | 1.688E−02 | 2.970E−08 |
| 6A7-H3K3-IgG4 | 2.308E+05 | 2.010E−04 | 8.705E−10 |
| 6A7-H4K2-IgG4 | 1.988E+05 | 7.874E−04 | 3.960E−09 |

Example 7. Thermal Stability of Anti-hCD40 Antibodies

Thermofluor assay was performed using the Protein Thermal Shift™ Dye Kit (Thermo Fisher Scientific) and QuantStudio™ 5 Real Time PCR Systems (Thermo Fisher Scientific). This assay measured thermostability using a fluorescent dye that binds to hydrophobic patches exposed as the protein unfolds.

The experiments were performed according to the manufacturer's protocol. In Step 1, samples were heated to 25° C. at 1.6° C./second. In Step 2, samples were heated to 99° C. at 0.05° C./second.

The table below summarizes the Tm for the tested humanized anti-hCD40 antibodies. The result for daceruzumab was also included for comparison purpose.

TABLE 4

| Antibody | Variable Domains | Type (constant domains) | Thermal stability (Tm ° C.) |
|---|---|---|---|
| 4H6-H3K2-IgG4 | 4H6 H3K2 | Human IgG4 | 75.03 |
| 4H6-H4K2-IgG4 | 4H6 H4K2 | Human IgG4 | 77.92 |
| 4H6-H3K3-IgG4 | 4H6 H3K3 | Human IgG4 | 75.21 |
| 4H6-H3K4-IgG4 | 4H6 H3K4 | Human IgG4 | 74.62 |
| 4H6-H4K3-IgG4 | 4H6 H4K3 | Human IgG4 | 76.91 |
| 4H6-H4K4-IgG4 | 4H6 H4K4 | Human IgG4 | 74.47 |
| 4H6-mHvKv-IgG1 | 4H6 mHvKv | Human IgG1 | 76.25 |
| 4H6-mHvKv-IgG4 | 4H6 mHvKv | Human IgG4 | 75.73 |
| 4H6-mHvKv-IgG1-N297A | 4H6 mHvKv | Human IgG1 with N297A mutation | 75.88 |
| 4H6-H3K2-IgG2 | 4H6 H3K2 | Human IgG2 | 75.22 |
| 4H6-H4K2-IgG2 | 4H6 H4K2 | Human IgG2 | 76.55 |
| 6A7-H3K2-IgG4 | 6A7 H3K2 | Human IgG4 | 77.77 |
| 6A7-H3K3-IgG4 | 6A7 H3K3 | Human IgG4 | 78.58 |
| 6A7-H4K2-IgG4 | 6A7 H4K2 | Human IgG4 | 76.66 |
| 6A7-H4K3-IgG4 | 6A7 H4K3 | Human IgG4 | 78.88 |
| 6A7-mHvKv-IgG1 | 6A7 mHvKv | Human IgG1 | 76.95 |
| 6A7-mHvKv-IgG2 | 6A7 mHvKv | Human IgG2 | 77.25 |
| 6A7-mHvKv-IgG4 | 6A7 mHvKv | Human IgG4 | 76.73 |
| 6A7-mHvKv-IgG1-LALA | 6A7 mHvKv | Human IgG1 with LALA mutation (L234A and L235A mutations in EU numbering) | 76.95 |
| 6A7-H3K3-IgG2 | 6A7 H3K3 | Human IgG2 | 79.07 |
| A7-H4K2-IgG2 | 6A7 H4K2 | Human IgG2 | 78.48 |
| 7F10-H1K1-IgG4 | 7F10 H1K1 | Human IgG4 | 74.36 |
| 7F10-H1K2-IgG4 | 7F10 H1K2 | Human IgG4 | 76.28 |
| 7F10-H1K3-IgG4 | 7F10 H1K3 | Human IgG4 | 75.10 |
| 7F10-H1K4-IgG4 | 7F10 H1K4 | Human IgG4 | 74.73 |
| 7F10-H2K1-IgG4 | 7F10 H2K1 | Human IgG4 | 73.99 |
| 7F10-H2K2-IgG4 | 7F10 H2K2 | Human IgG4 | 75.54 |
| 7F10-H2K3-IgG4 | 7F10 H2K3 | Human IgG4 | 74.36 |
| 7F10-H2K4-IgG4 | 7F10 H2K4 | Human IgG4 | 74.13 |
| 7F10-H3K1-IgG4 | 7F10 H3K1 | Human IgG4 | 73.62 |
| 7F10-H3K2-IgG4 | 7F10 H3K2 | Human IgG4 | 74.95 |
| 7F10-H3K3-IgG4 | 7F10 H3K3 | Human IgG4 | 74.65 |
| 7F10-H3K4-IgG4 | 7F10 H3K4 | Human IgG4 | 73.99 |
| 7F10-mHvKv-IgG1 | 7F10 mHvKv | Human IgG1 | 75.54 |
| 7F10-mHvKv-IgG1-N297A | 7F10 mHvKv | Human IgG1 with N297A mutation | 76.21 |
| 7F10-mHvKv-IgG2 | 7F10 mHvKv | Human IgG2 | 75.84 |
| 7F10-mHvKv-IgG4 | 7F10 mHvKv | Human IgG4 | 75.02 |
| Daceruzumab | NA | Human IgG1 | 77.46 |

Example 8. In Vivo Testing of Mouse and Chimeric Anti-hCD40 Antibodies

In order to test the anti-hCD40 antibodies in vivo and to predict the effects of these antibodies in human, a humanized CD40 mouse model was generated. The humanized CD40 mouse model was engineered to express a chimeric CD40 protein (SEQ ID NO: 29) wherein a part of the extracellular region of the mouse CD40 protein was replaced with the corresponding human CD40 extracellular region. The amino acid residues 20-192 of mouse CD40 (SEQ ID NO: 27) were replaced by amino acid residues 20-192 of human CD40 (SEQ ID NO: 26). The humanized mouse model (B-hCD40 mice) provides a new tool for testing new therapeutic treatments in a clinical setting by significantly decreasing the difference between clinical outcome in human and in ordinary mice expressing mouse CD40. A detailed description regarding humanized CD40 mouse model can be found in PCT/CN2018/091845, which is incorporated herein by reference in its entirety.

The anti-hCD40 antibodies were tested for their effect on tumor growth in vivo in a model of colon carcinoma. MC-38 cancer tumor cells (colon adenocarcinoma cell) were injected subcutaneously in B-hCD40 mice. When the tumors in the mice reached a volume of 100~150 mm$^3$, the mice were randomly placed into different groups based on the volume of the tumor (five mice in each group).

The mice were then injected with physiological saline (PS) and anti-hCD40 antibodies by intraperitoneal administration. The antibody was given on the first day and the fourth day of each week for 3 weeks (6 injections in total).

The injected amount was calculated based on the weight of the mouse at 3 mg/kg. The length of the long axis and the short axis of the tumor were measured and the volume of the tumor was calculated as 0.5×(long axis)×(short axis). The weight of the mice was also measured before the injection, when the mice were placed into different groups (before the first antibody injection), twice a week during the antibody injection period, and before euthanization.

The tumor growth inhibition percentage (TGI %) was calculated using the following formula: TGI (%)=[1−(Ti−T0)/(Vi−V0)]×100. Ti is the average tumor volume in the treatment group on day i. T0 is the average tumor volume in the treatment group on day zero. Vi is the average tumor volume in the control group on day i. V0 is the average tumor volume in the control group on day zero.

T-test was performed for statistical analysis. A TGI % higher than 60% indicates significant suppression of tumor growth. P<0.05 is a threshold to indicate significant difference.

In Vivo Results for Mouse Anti-hCD40 Antibodies

In each of the seven groups (G1-G7), B-hCD40 mice were injected with physiological saline (PS) as a control (G1), the mouse anti-hCD40 antibody 03-9D7 (G2; 3 mg/kg), the mouse anti-hCD40 antibody 03-2A7 (G3; 3 mg/kg), the mouse anti-hCD40 antibody 03-9E11 (G4; 3 mg/kg), the mouse anti-hCD40 antibody 06-6A7 (G5; 3 mg/kg), the mouse anti-hCD40 antibody 07-4H6 (G6; 3 mg/kg), or the mouse anti-hCD40 antibody 03-7F10 (G7; 3 mg/kg).

Figure 7:
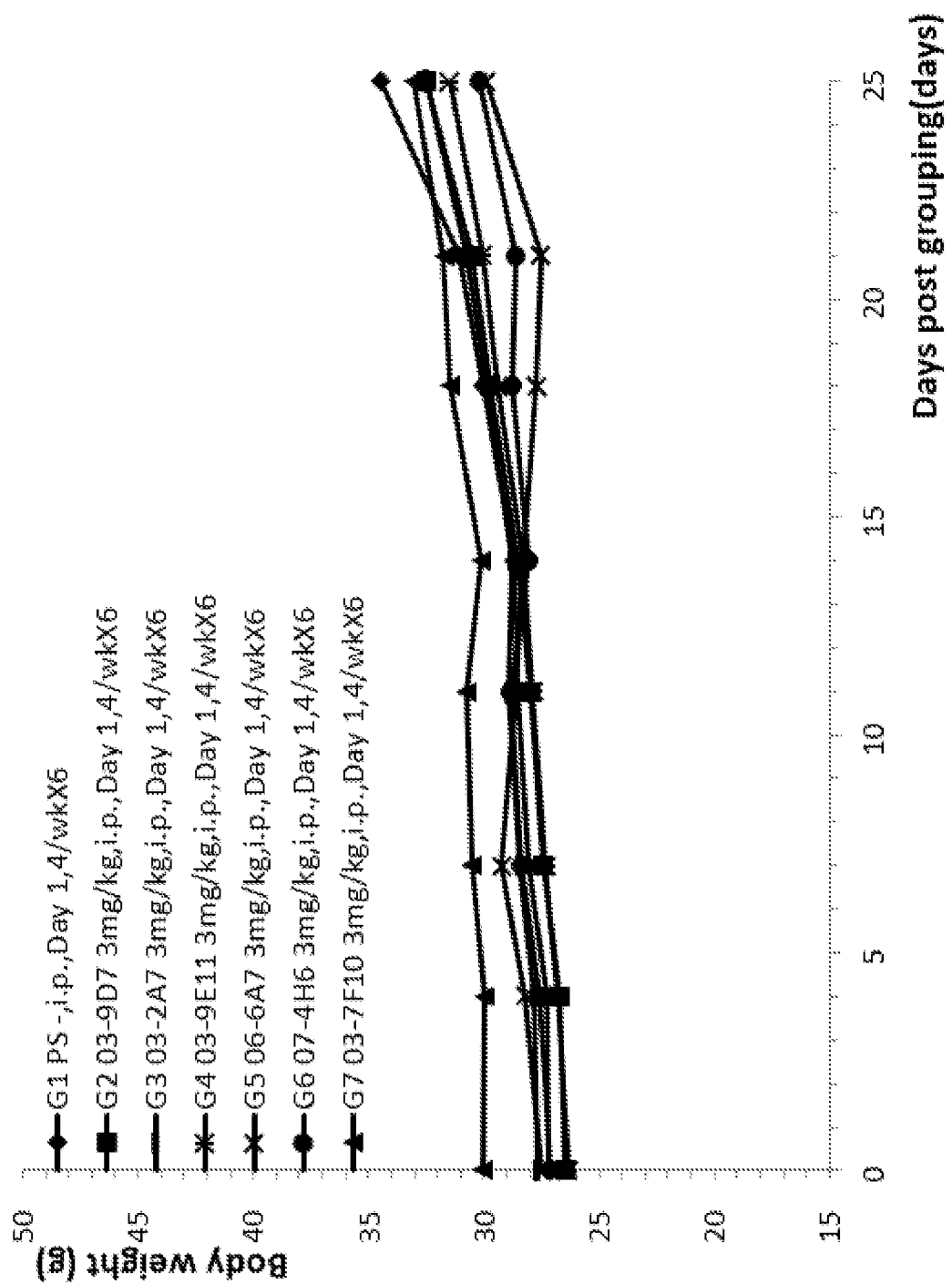
FIG. 7 is a graph showing body weight over time of humanized CD40 mice (B-hCD40) with MC-38 tumor cells treated with mouse anti-hCD40 antibodies. PS stands for physiological saline (control).
Figure 8:
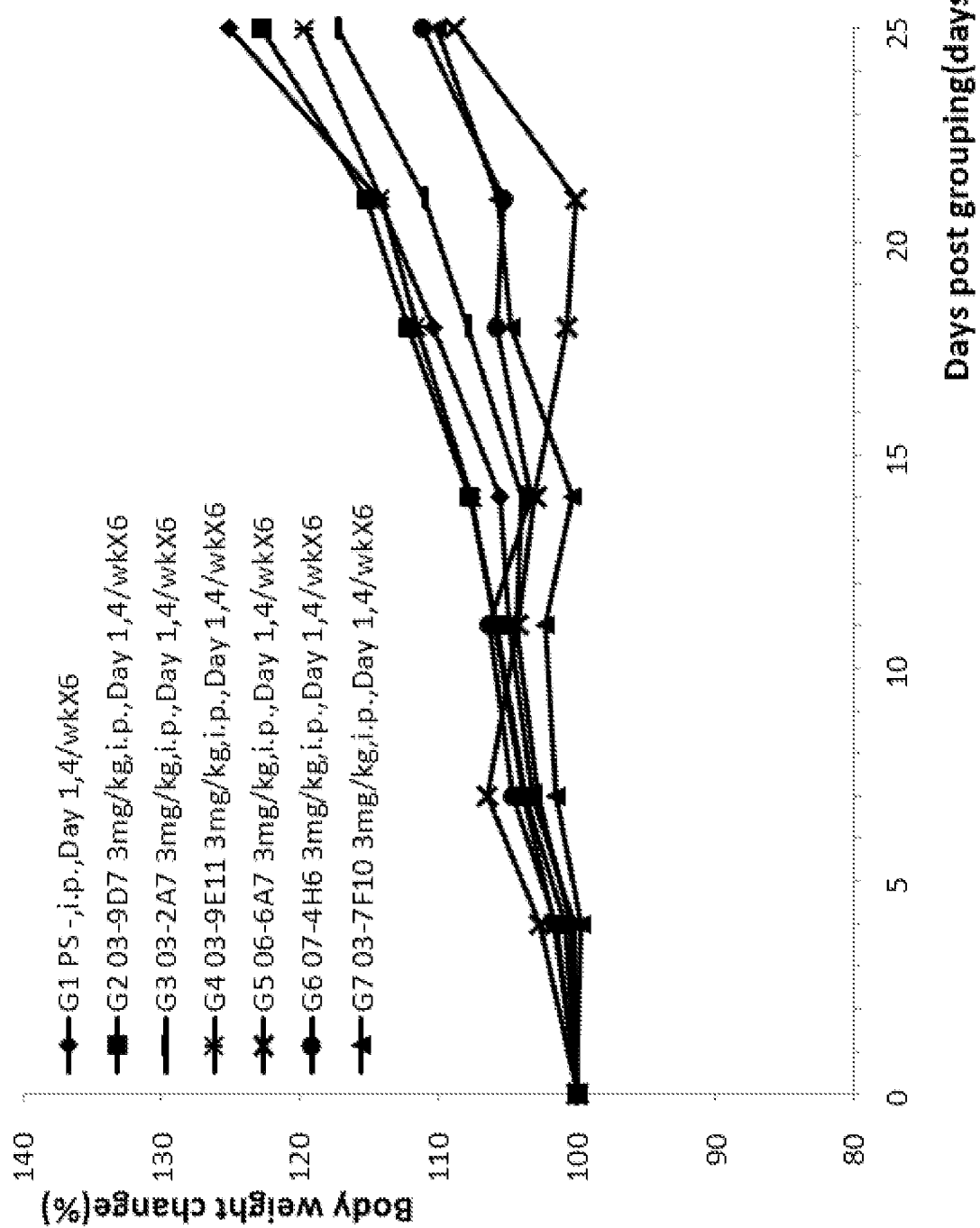
FIG. 8 is a graph showing percentage change of body weight over time of humanized CD40 mice (B-hCD40) with MC-38 tumor cells treated with mouse anti-hCD40 antibodies. PS stands for physiological saline (control).

The weight of the mice was monitored during the entire treatment period (FIG. 7, and FIG. 8). Not much difference in weight was observed among these groups. The results showed that 03-7F10, 06-6A7, and 07-4H6 were well tolerated and not toxic to the mice.

Figure 9:
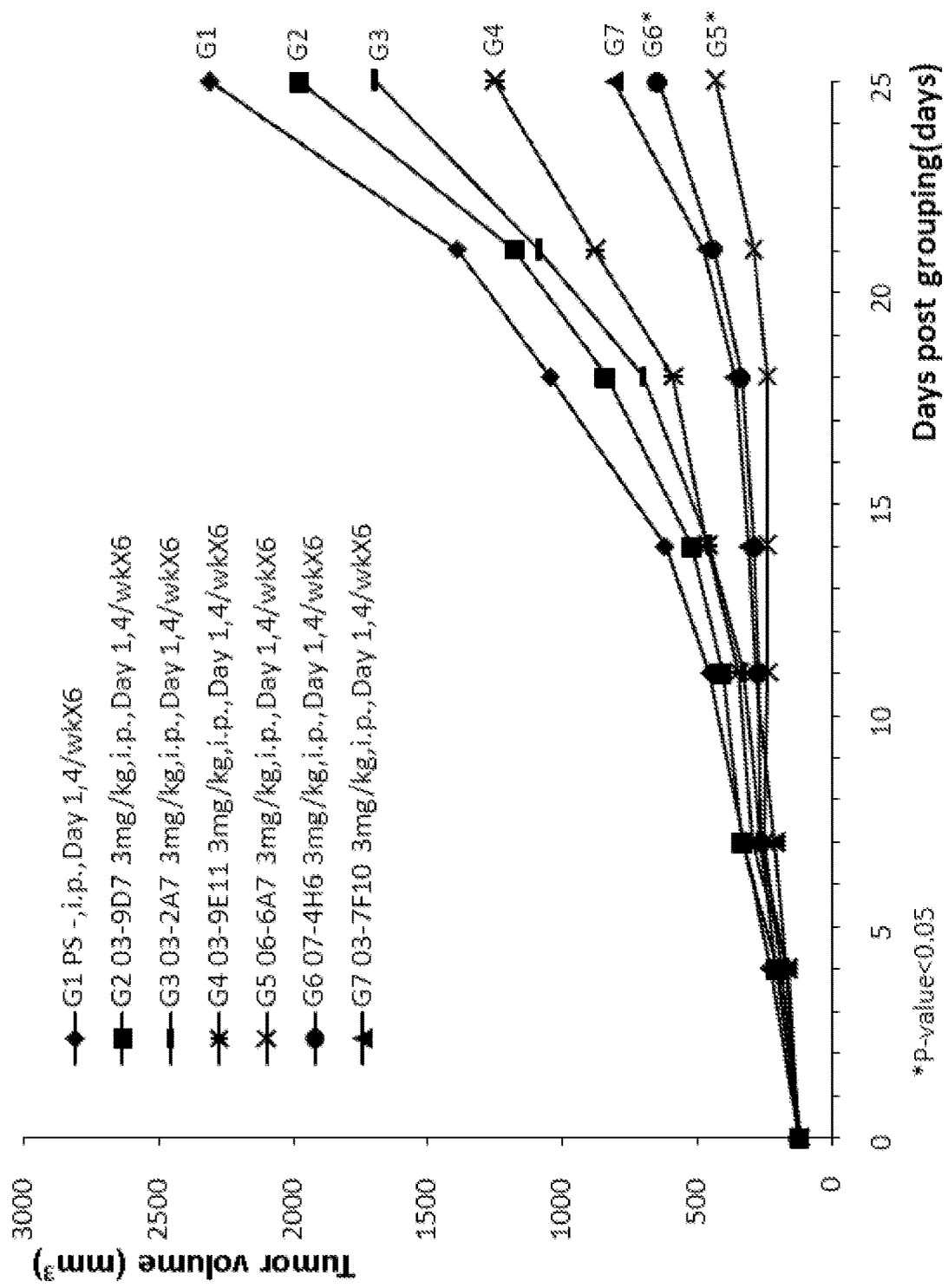
FIG. 9 is a graph showing tumor size over time in humanized CD40 mice (B-hCD40) with MC-38 tumor cells treated with mouse anti-hCD40 antibodies. PS stands for physiological saline (control).

The tumor size in groups treated with 03-7F10, 06-6A7, and 07-4H6 increased to a lesser extent compared to the control group (FIG. 9) and other antibody treatment groups.

The TGI % at day 25 (25 days after grouping) was also calculated as shown in the table below.

TABLE 5

|  |  | Tumor volume(mm$^3$) | | | | | P value | |
|---|---|---|---|---|---|---|---|---|
|  |  | Day 0 | Day 11 | Day 21 | Day 25 | Survival | TGI$_{TV}$% | Body weight | Tumor Volume |
| Control | G1 | 121 ± 7 | 457 ± 35 | 1391 ± 235 | 2311 ± 531 | 4/5 | n.a. | n.a. | n.a. |
| Treat | G2 03-9D7 | 124 ± 9 | 407 ± 79 | 1174 ± 300 | 1979 ± 488 | 5/5 | 15.29% | 0.456 | 0.660 |
|  | G3 03-2A7 | 121 ± 8 | 327 ± 34 | 1087 ± 125 | 1696 ± 129 | 5/5 | 28.13% | 0.256 | 0.248 |
|  | G4 03-9E11 | 121 ± 10 | 347 ± 64 | 880 ± 98 | 1254 ± 169 | 5/5 | 48.28% | 0.129 | 0.074 |
|  | G5 06-6A7 | 120 ± 8 | 238 ± 26 | 293 ± 43 | 434 ± 59 | 5/5 | 85.65% | 0.419 | 0.005 |
|  | G6 07-4H6 | 119 ± 8 | 274 ± 25 | 440 ± 120 | 647 ± 172 | 5/5 | 75.90% | 0.118 | 0.013 |
|  | G7 03-7F10 | 123 ± 10 | 286 ± 43 | 476 ± 108 | 809 ± 227 | 5/5 | 68.67% | 0.495 | 0.131 |

In Vivo Results for Chimeric Anti-hCD40 Antibodies

Chimeric anti-hCD40 antibodies 6A7-mHvKv-IgG1 (G2), 6A7-mHvKv-IgG2 (G3), 6A7-mHvKv-IgG4 (G4), 6A7-mHvKv-IgG1-N297A (G5) and 6A7-mHvKv-IgG1-LALA (G6) were administered into B-hCD40 mice (humanized CD40 mice) by intraperitoneal administration. Physiological saline was injected as a control (Group 1, G1). Dacetuzumab (humanized anti-CD40 monoclonal antibody, which is designed to treat hematological malignancies) was also included for comparison purpose (G7).

The injected amount of the antibodies was calculated based on the weight of the mouse at 3 mg/kg. The antibodies were given on the first day and the fourth day of each week (6 injections in total).

Figure 10:
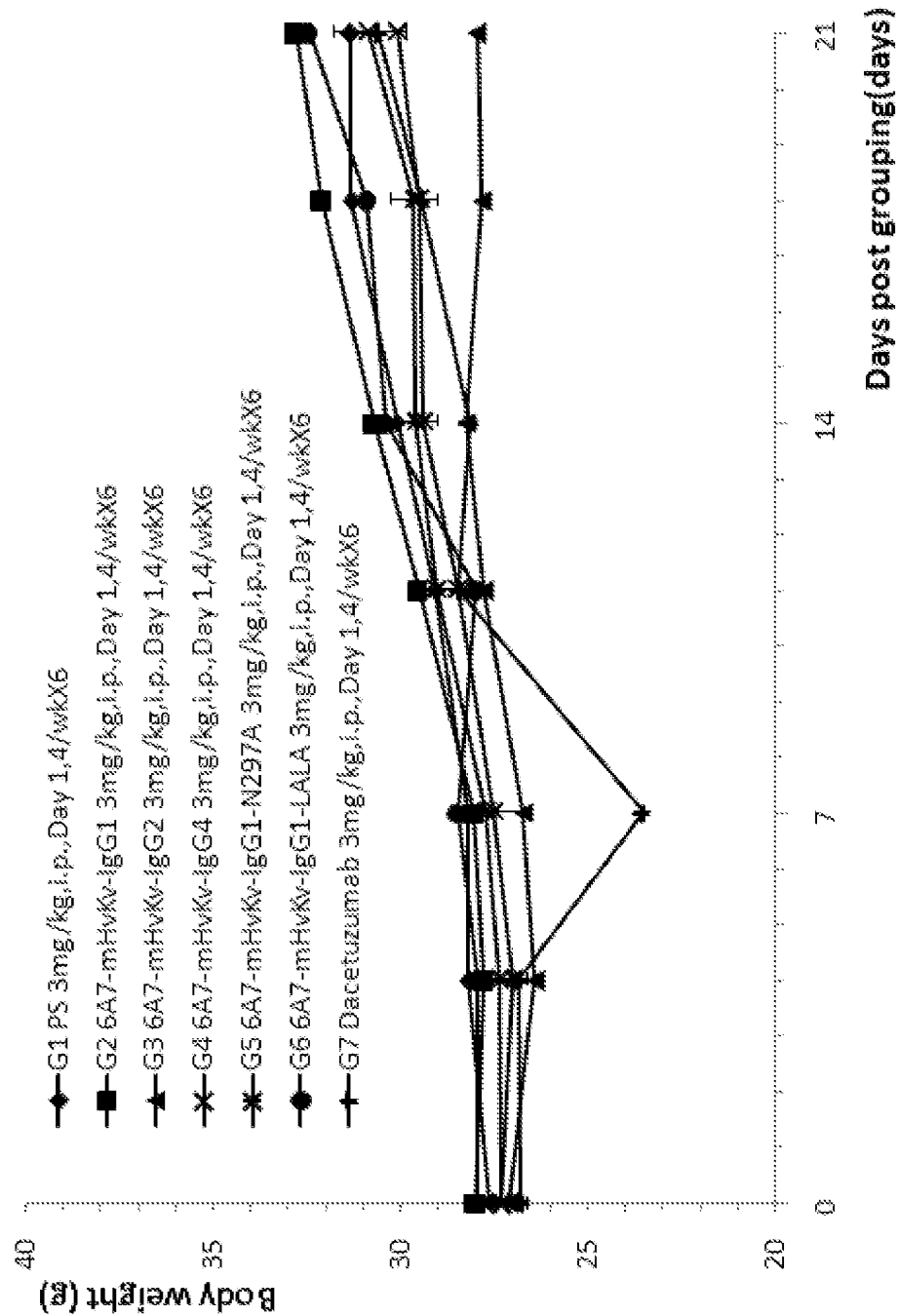
FIG. 10 is a graph showing body weight over time of humanized CD40 mice (B-hCD40) with MC-38 tumor cells treated with chimeric anti-hCD40 antibodies. PS stands for physiological saline (control).
Figure 11:
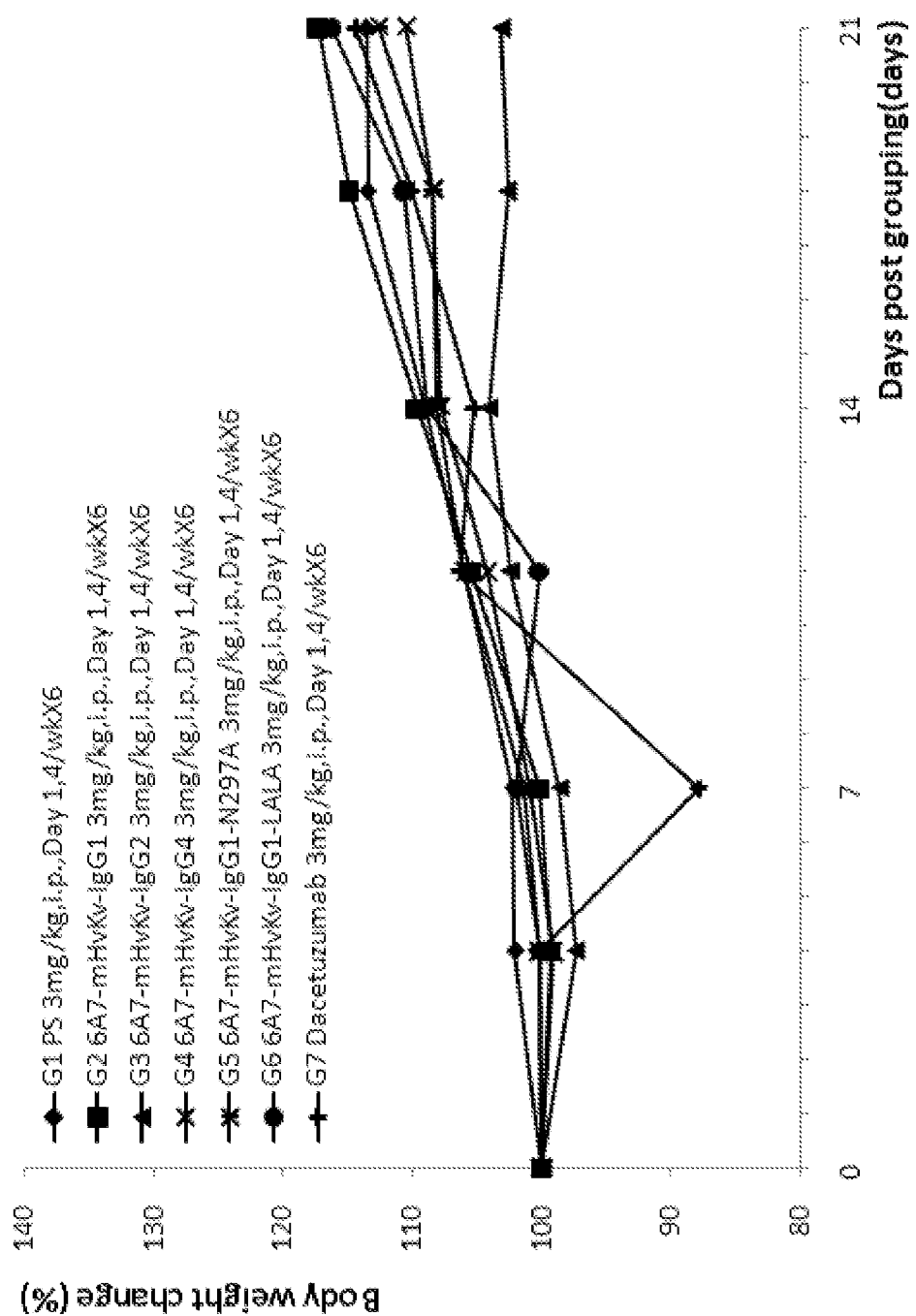
FIG. 11 is a graph showing percentage change of body weight over time of humanized CD40 mice (B-hCD40) with MC-38 tumor cells treated with chimeric anti-hCD40 antibodies. PS stands for physiological saline (control).

The weight of the mice was monitored during the entire treatment period. The weight of mice in different groups all increased (FIG. 10, and FIG. 11). No clear difference in weight was observed among the different groups. The results showed that the anti-hCD40 antibodies were well tolerated and not toxic to the mice.

Figure 12:
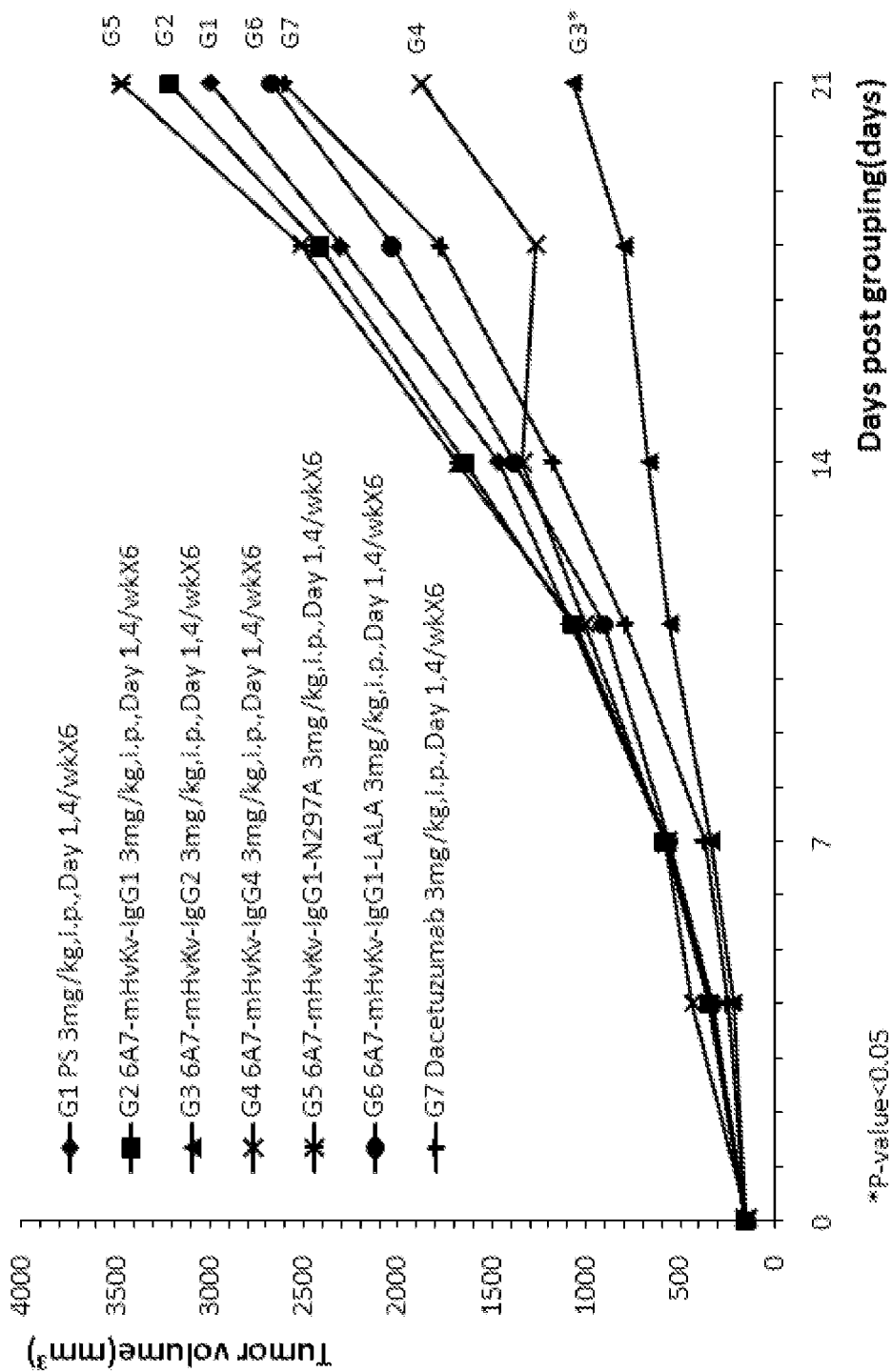
FIG. 12 is a graph showing tumor size over time in humanized CD40 mice (B-hCD40) with MC-38 tumor cells treated with chimeric anti-hCD40 antibodies. PS stands for physiological saline (control).

The tumor size showed significant difference in groups treated with certain chimeric antibodies compared to the control group (FIG. 12).

The TGI % at day 21 (21 days after grouping) for each treatment group was calculated as shown in the table below.

TABLE 6

|  |  | Tumor volume(mm$^3$) | | | | | | P value | |
|---|---|---|---|---|---|---|---|---|---|
|  |  | Day 0 | Day 7 | Day 14 | Day 21 | Survival | TGI$_{TV}$% | Body weight | Tumor Volume |
| Control | G1 | 153 ± 18 | 567 ± 98 | 1465 ± 275 | 2995 ± 714 | 5/5 | n.a. | n.a. | n.a. |
| Treat | G2 | 153 ± 19 | 585 ± 120 | 1646 ± 377 | 3214 ± 732 | 5/5 | -7.70% | 0.371 | 0.836 |
|  | G3 | 153 ± 22 | 341 ± 18 | 672 ± 114 | 1072 ± 238 | 5/5 | 67.67% | 0.042 | 0.034 |
|  | G4 | 151 ± 32 | 583 ± 109 | 1343 ± 484 | 1875 ± 164 | 4/5 | 39.32% | 0.415 | 0.215 |
|  | G5 | 152 ± 33 | 568 ± 61 | 1686 ± 308 | 3466 ± 719 | 5/5 | -16.59% | 0.772 | 0.655 |
|  | G6 | 151 ± 26 | 562 ± 50 | 1385 ± 104 | 2670 ± 242 | 5/5 | 11.37% | 0.390 | 0.678 |
|  | G7 | 154 ± 22 | 371 ± 62 | 1180 ± 164 | 2606 ± 395 | 5/5 | 13.73% | 0.585 | 0.646 |

The results showed that chimeric antibodies 6A7-mHvKv-IgG2 significantly inhibited tumor growth. Among these antibodies, 6A7-mHvKv-IgG4 (G4) and 6A7-mHvKv-IgG1-LALA (G6) also have tumor inhibiting effects.

Example 9. In Vivo Testing of Humanized Anti-hCD40 Antibodies

The humanized anti-hCD40 antibodies were tested in CD40 humanized mice (B-hCD40) to demonstrate their effect on tumor growth in vivo.

MC-38 cancer tumor cells (colon adenocarcinoma cell) were injected subcutaneously in B-hCD40 mice. When the tumors in the mice reached a volume of 150±50 mm$^3$, the mice were randomly placed into different groups based on the volume of the tumor (five mice in each group).

The mice were then injected with physiological saline as a control (G1), humanized anti-CD40 antibody 6A7-H3K3-IgG2 (G2), humanized anti-CD40 antibody 6A7-H4K2-IgG2 (G3), humanized anti-CD40 antibody 6A7-H3K3-IgG4 (G4), or humanized anti-CD40 antibody 6A7-H4K2-IgG4 (G5).

The antibodies were given on the second day and the fifth day of each week by intraperitoneal injection at 3 mg/kg for 3 weeks (6 injections in total).

Figure 13:
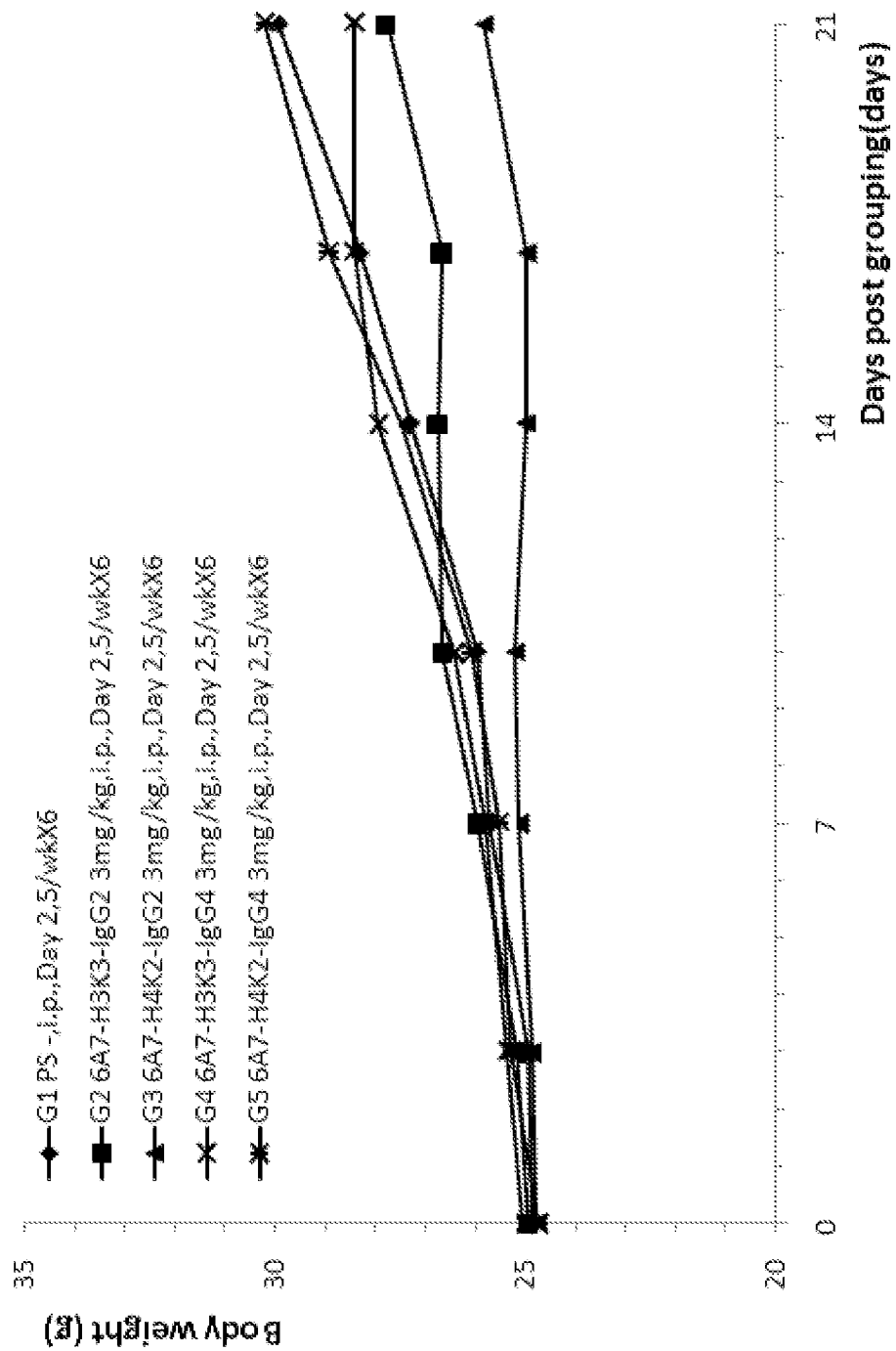
FIG. 13 is a graph showing body weight over time of humanized CD40 mice (B-hCD40) with MC-38 tumor cells treated with humanized anti-hCD40 antibodies. PS stands for physiological saline (control).
Figure 14:
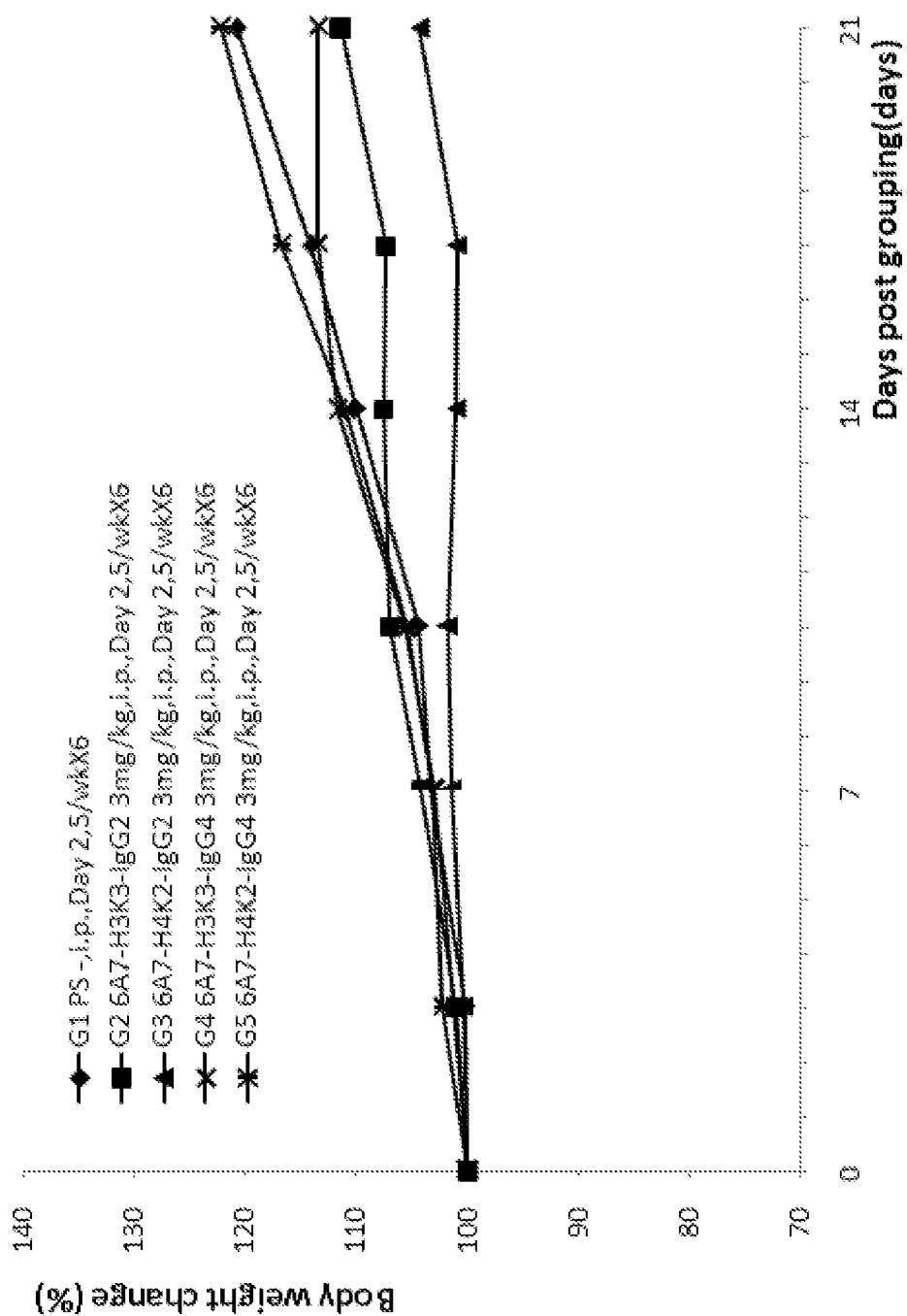
FIG. 14 is a graph showing percentage change of body weight over time of humanized CD40 mice (B-hCD40) with MC-38 tumor cells treated with humanized anti-hCD40 antibodies. PS stands for physiological saline (control).

The weight of the mice was monitored during the entire treatment period. The weight of mice in different groups all increased (FIG. 13, and FIG. 14). The results showed that the anti-hCD40 antibodies were well tolerated and not toxic to the mice.

Figure 15:
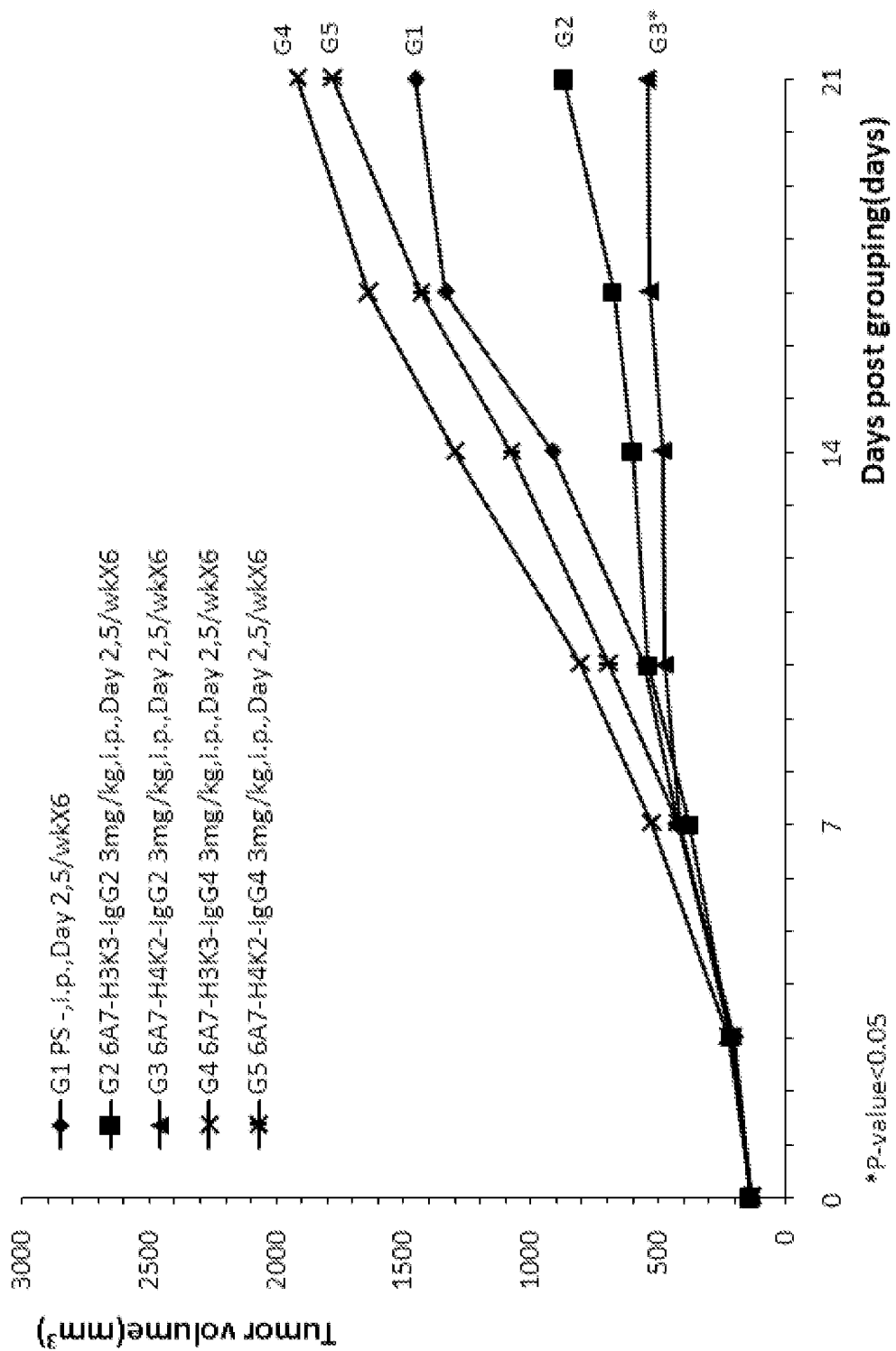
FIG. 15 is a graph showing tumor size over time in humanized CD40 mice (B-hCD40) with MC-38 tumor cells treated with humanized anti-hCD40 antibodies. PS stands for physiological saline (control).

The tumor size showed significant difference in groups treated with the anti-hCD40 antibodies (FIG. 15). Particularly, the tumor size in G3 is smaller than G1 (P=0.15).

The TGI % at Day 21 (21 days after grouping) for each treatment group was also calculated as shown in the table below.

TABLE 7

|  |  | Tumor volume(mm$^3$) | | | | | P value | |
|---|---|---|---|---|---|---|---|---|
|  |  | Day 0 | Day 7 | Day 14 | Day 21 | Survival | TGI$_{TV}$% | Body weight | Tumor Volume |
| Control | G1 | 137 ± 4 | 424 ± 45 | 916 ± 127 | 1453 ± 310 | 4/5 | n.a. | n.a. | n.a. |
| Treat | G2 | 137 ± 7 | 376 ± 22 | 602 ± 118 | 871 ± 276 | 5/5 | 44.26% | 0.105 | 0.203 |
|  | G3 | 137 ± 7 | 414 ± 26 | 484 ± 65 | 544 ± 67 | 5/5 | 69.10% | 0.002 | 0.015 |
|  | G4 | 137 ± 5 | 523 ± 28 | 1303 ± 158 | 1925 ± 198 | 5/5 | −35.88% | 0.177 | 0.223 |
|  | G5 | 137 ± 5 | 420 ± 32 | 1081 ± 99 | 1778 ± 121 | 5/5 | −24.72% | 0.720 | 0.321 |

The results above show that some of the humanized anti-hCD40 antibodies can inhibit tumor growth. Among them, 6A7-H4K2-IgG2 (G3) had the highest tumor growth inhibition percentage (TGI %).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that binds to CD40 (TNF Receptor Superfamily Member 5) comprising:
   a heavy chain variable region (VH) comprising complementarity determining regions (CDRs) 1, 2, and 3, wherein the VH CDR1 region comprises an amino acid sequence that is identical to a selected VH CDR1 amino acid sequence, the VH CDR2 region comprises an amino acid sequence that is identical to a selected VH CDR2 amino acid sequence, and the VH CDR3 region comprises an amino acid sequence that is identical to a selected VH CDR3 amino acid sequence; and
   a light chain variable region (VL) comprising CDRs 1, 2, and 3, wherein the VL CDR1 region comprises an amino acid sequence that is identical to a selected VL CDR1 amino acid sequence, the VL CDR2 region comprises an amino acid sequence that is identical to a selected VL CDR2 amino acid sequence, and the VL CDR3 region comprises an amino acid sequence that is identical to a selected VL CDR3 amino acid sequence, wherein the selected VH CDRs 1, 2, and 3 amino acid sequences and the selected VL CDRs, 1, 2, and 3 amino acid sequences are one of the following:
   (1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively;
   (2) the selected VH CDRs 1, 2, 3 amino acid sequences are set forth in SEQ ID NOs: 19, 20, 3, respectively, and the selected VL CDRs 1, 2, 3 amino acid sequences are set forth in SEQ ID NOs: 4, 21, 6, respectively;
   (3) the selected VH CDRs 1, 2, 3 amino acid sequences are set forth in SEQ ID NOs: 7, 8, 9, respectively, and the selected VL CDRs 1, 2, 3 amino acid sequences are set forth in SEQ ID NOs: 10, 11, 12, respectively;
   (4) the selected VH CDRs 1, 2, 3 amino acid sequences are set forth in SEQ ID NOs: 22, 23, 9, respectively, and the selected VL CDRs 1, 2, 3 amino acid sequences are set forth in SEQ ID NOs: 10, 11, 12, respectively;
   (5) the selected VH CDRs 1, 2, 3 amino acid sequences are set forth in SEQ ID NOs: 13, 14, 15, respectively, and the selected VL CDRs 1, 2, 3 amino acid sequences are set forth in SEQ ID NOs: 16, 17, 18, respectively; and
   (6) the selected VH CDRs 1, 2, 3 amino acid sequences are set forth in SEQ ID NOs: 24, 25, 15, respectively, and the selected VL CDRs 1, 2, 3 amino acid sequences are set forth in SEQ ID NOs: 16, 17, 18, respectively.

2. The antibody or antigen-binding fragment thereof of claim 1, wherein the VH comprises CDRs 1, 2, 3 with the amino acid sequences set forth in SEQ ID NOs: 7, 8, and 9, respectively, and the VL comprises CDRs 1, 2, 3 with the amino acid sequences set forth in SEQ ID NOs: 10, 11, and 12, respectively, according to Kabat numbering.

3. The antibody or antigen-binding fragment thereof of claim 1, wherein the antibody or antigen-binding fragment is a humanized antibody or antigen-binding fragment thereof.

4. The antibody or antigen-binding fragment thereof of claim 1, wherein the antibody or antigen-binding fragment is a single-chain variable fragment (scFV) or a bispecific antibody.

5. A method of producing an antibody or an antigen-binding fragment thereof, the method comprising culturing a cell comprising a nucleic acid encoding the antibody or the antigen-binding fragment thereof of claim 1 under conditions sufficient for the cell to produce the antibody or the antigen-binding fragment.

6. An antibody-drug conjugate comprising the antibody or antigen-binding fragment thereof of claim 1 covalently bound to a therapeutic agent.

7. A method of treating a subject having cancer, the method comprising administering a therapeutically effective amount of a composition comprising the antibody or antigen-binding fragment thereof of claim 1 to the subject.

8. The method of claim 7, wherein the subject has a solid tumor, melanoma, pancreatic carcinoma, mesothelioma, hematological malignancy, Non-Hodgkin's lymphoma, lymphoma, or chronic lymphocytic leukemia.

9. A pharmaceutical composition comprising the antibody or antigen-binding fragment thereof of claim 1, and a pharmaceutically acceptable carrier.

10. The antibody or antigen-binding fragment thereof of claim 1, wherein the VH comprises CDRs 1, 2, 3 with the amino acid sequences set forth in SEQ ID NOs: 22, 23, and respectively, and the VL comprises CDRs 1, 2, 3 with the amino acid sequences set forth in SEQ ID NOs: 10, 11, and 12, respectively, according to Chothia numbering.

11. The antibody or antigen-binding fragment thereof of claim 1, wherein the VH comprises CDRs 1, 2, 3 with the amino acid sequences set forth in SEQ ID NOs: 1, 2, and 3, respectively, and the VL comprises CDRs 1, 2, 3 with the amino acid sequences set forth in SEQ ID NOs: 4, 5, and 6, respectively, according to Kabat numbering.

12. The antibody or antigen-binding fragment thereof of claim 1, wherein the VH comprises CDRs 1, 2, 3 with the amino acid sequences set forth in SEQ ID NOs: 13, 14, and 15, respectively, and the VL comprises CDRs 1, 2, 3 with the amino acid sequences set forth in SEQ ID NOs: 16, 17, and 18, respectively, according to Kabat numbering.

13. The antibody or antigen-binding fragment thereof of claim 1, wherein the VH comprises CDRs 1, 2, 3 with the amino acid sequences set forth in SEQ ID NOs: 19, 20, and 3, respectively, and the VL comprises CDRs 1, 2, 3 with the amino acid sequences set forth in SEQ ID NOs: 4, 21, and 6, respectively, according to Chothia numbering.

14. The antibody or antigen-binding fragment thereof of claim 1, wherein the VH comprises CDRs 1, 2, 3 with the amino acid sequences set forth in SEQ ID NOs: 24, 25, and 15, respectively, and the VL comprises CDRs 1, 2, 3 with the amino acid sequences set forth in SEQ ID NOs: 16, 17, and 18, respectively, according to Chothia numbering.

* * * * *

UNITED STATES PATENT AND TRADEMARK OFFICE
CERTIFICATE OF CORRECTION

PATENT NO. : 11,142,582 B2  
APPLICATION NO. : 17/149209  
DATED : October 12, 2021  
INVENTOR(S) : Yi Yang et al.

Page 1 of 1

It is certified that error appears in the above-identified patent and that said Letters Patent is hereby corrected as shown below:

In the Claims

Claim 10: In Column 81, Lines 23-24, please delete "SEQ ID NOs: 22, 23, and respectively" and insert -- SEQ ID Nos: 22, 23, and 9, respectively --, therefor.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*